US009145555B2

(12) United States Patent
Smolke et al.

(10) Patent No.: US 9,145,555 B2
(45) Date of Patent: Sep. 29, 2015

(54) INTEGRATED—LIGAND-RESPONSIVE MICRORNAS

(75) Inventors: Christina D. Smolke, Stanford, CA (US); Chase L. Beisel, Bethesda, MD (US)

(73) Assignee: California Institute of Technology, Pasadena, CA (US)

( * ) Notice: Subject to any disclaimer, the term of this patent is extended or adjusted under 35 U.S.C. 154(b) by 589 days.

(21) Appl. No.: 12/753,778

(22) Filed: Apr. 2, 2010

(65) Prior Publication Data

US 2010/0255545 A1 Oct. 7, 2010

Related U.S. Application Data

(60) Provisional application No. 61/166,203, filed on Apr. 2, 2009.

(51) Int. Cl.
*C07H 21/04* (2006.01)
*C12N 15/11* (2006.01)

(52) U.S. Cl.
CPC ........ *C12N 15/111* (2013.01); *C12N 2310/141* (2013.01); *C12N 2310/16* (2013.01); *C12N 2310/3519* (2013.01); *C12N 2320/50* (2013.01)

(58) Field of Classification Search
CPC .................. C12N 2310/16; C12N 2310/3519; C12N 2320/50
See application file for complete search history.

(56) References Cited

U.S. PATENT DOCUMENTS

| | | |
|---|---|---|
| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen et al. |
| 4,897,355 A | 1/1990 | Eppstein et al. |
| 5,013,556 A | 5/1991 | Woodle |
| 5,013,830 A | 5/1991 | Ohtsuka et al. |
| 5,093,246 A | 3/1992 | Cech |
| 5,108,921 A | 4/1992 | Low |
| 5,176,996 A | 1/1993 | Hogan |
| 5,213,804 A | 5/1993 | Martin |
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa |
| 5,264,423 A | 11/1993 | Cohen et al. |
| 5,264,564 A | 11/1993 | Matteucci |
| 5,270,163 A | 12/1993 | Gold |
| 5,276,019 A | 1/1994 | Cohen et al. |
| 5,354,844 A | 10/1994 | Beug |
| 5,356,633 A | 10/1994 | Woodle |
| 5,395,619 A | 3/1995 | Zalipsky |
| 5,416,016 A | 5/1995 | Low |
| 5,417,978 A | 5/1995 | Tari |
| 5,459,127 A | 10/1995 | Felgner |
| 5,462,854 A | 10/1995 | Coassin |
| 5,469,854 A | 11/1995 | Unger |
| 5,512,295 A | 4/1996 | Kornberg |
| 5,521,291 A | 5/1996 | Curiel |
| 5,525,719 A | 6/1996 | Srivastava et al. |
| 5,527,528 A | 6/1996 | Allen |
| 5,534,259 A | 7/1996 | Zalipsky |
| 5,543,152 A | 8/1996 | Webb |
| 5,543,158 A | 8/1996 | Gref |
| 5,547,932 A | 8/1996 | Curiel |
| 5,556,948 A | 9/1996 | Tagawa |
| 5,580,575 A | 12/1996 | Unger |
| 5,582,981 A | 12/1996 | Toole |
| 5,583,020 A | 12/1996 | Sullivan |
| 5,591,721 A | 1/1997 | Agrawal |
| 5,595,756 A | 1/1997 | Bally |
| 5,736,392 A | 4/1998 | Hawley-Nelson et al. |
| 5,756,291 A | 5/1998 | Griffin |
| 5,767,099 A | 6/1998 | Harris et al. |
| 5,777,153 A | 7/1998 | Lin et al. |
| 5,780,053 A | 7/1998 | Ashley et al. |
| 5,830,430 A | 11/1998 | Unger et al. |
| 5,830,653 A | 11/1998 | Froehler et al. |
| 5,851,548 A | 12/1998 | Dattagupta et al. |
| 5,855,910 A | 1/1999 | Ashley et al. |
| 6,458,559 B1 | 10/2002 | Shi et al. |
| 2002/0106648 A1 | 8/2002 | Lizardi et al. |
| 2002/0150996 A1 | 10/2002 | Nilsen-Hamilton |
| 2002/0166132 A1 | 11/2002 | Scherman et al. |

(Continued)

FOREIGN PATENT DOCUMENTS

| | | |
|---|---|---|
| AU | 2004206255 B2 | 8/2008 |
| WO | WO 88/04300 | 6/1988 |

(Continued)

OTHER PUBLICATIONS

U.S. Appl. No. 12/218,628, filed Mar. 26, 2009, Christina D. Smolke.
Buskirk et al., "Engineering a Ligand-Dependent RNA Transcriptional Activator." 2004 Chemistry & Biology 11:1157-1163.
Buskirk et al., "In Vivo Evolution of an RNA-Based Transcriptional Activator." 2003 Chemistry & Biology 10:533-540.
Famulok, "Bringing Picomolar Protein Detection Into Proximity." 2002 Nature Biotechnology 20:448-449.
Fredriksson et al., "Protein Detection Using Proximity-Dependent DNA Litagation Assays." 2002 Nature Biotechnology 20:473-477.
Hesselberth et al., "Simultaneous Detection of Diverse Analytes with an Aptazyme Ligase Array." 2003 Analytical Biochemistry 312:106-112.
Luzi et al., "New Trends in Affinity Sensing: Aptamers for Ligand Binding." 2003 Trends in Analytical Chemistry 22:810-818.
Nutiu et al., "Structure-Switching Signaling Aptamers: Transducing Molecular Recognition Into Fluorescence Signaling." 2004 Chem. Eur. J. 10:1868-1876.
Nutiu et al., "Structure-Switching Signaling Aptamers." 2003 J. Am. Chem. Soc. 125:4771-4778.

(Continued)

*Primary Examiner* — J. E. Angell
(74) *Attorney, Agent, or Firm* — McCarter & English, LLP; Yu Lu; Jin Wang, Esq.

(57) ABSTRACT

The present application relates to nucleic acids that encode an miRNA and a sensor domain that can respond to a ligand. In some embodiments, the sensor domain is an RNA aptamer that modulates processing of the miRNA by an RNA processing enzyme, for example, Drosha.

28 Claims, 14 Drawing Sheets

(56) References Cited

U.S. PATENT DOCUMENTS

| | | | |
|---|---|---|---|
| 2003/0105051 | A1 | 6/2003 | McSwiggen |
| 2003/0124595 | A1 | 7/2003 | Lizardi |
| 2003/0157030 | A1 | 8/2003 | Davis et al. |
| 2004/0063654 | A1 | 4/2004 | Davis |
| 2004/0072785 | A1 | 4/2004 | Wolff et al. |
| 2004/0086884 | A1 | 5/2004 | Beach |
| 2004/0162235 | A1 | 8/2004 | Trubetskoy et al. |
| 2004/0204377 | A1 | 10/2004 | Rana et al. |
| 2005/0003362 | A1 | 1/2005 | Crylov et al. |
| 2005/0026286 | A1 | 2/2005 | Chi et al. |
| 2005/0037496 | A1 | 2/2005 | Rozema et al. |
| 2005/0042227 | A1 | 2/2005 | Zankel et al. |
| 2005/0048647 | A1 | 3/2005 | Taira et al. |
| 2005/0064595 | A1 | 3/2005 | MacLachlan et al. |
| 2005/0256071 | A1 | 11/2005 | Davis |
| 2005/0265957 | A1 | 12/2005 | Monahan et al. |
| 2006/0008910 | A1 | 1/2006 | MacLachlan et al. |
| 2006/0088864 | A1* | 4/2006 | Smolke et al. ............... 435/6 |
| 2006/0105975 | A1 | 5/2006 | Pendergrast et al. |
| 2006/0172925 | A1 | 8/2006 | Gorenstein et al. |
| 2006/0178327 | A1 | 8/2006 | Yeung et al. |
| 2006/0240093 | A1 | 10/2006 | MacLachlan et al. |
| 2007/0077571 | A1 | 4/2007 | Ellington |
| 2007/0083947 | A1 | 4/2007 | Huang et al. |
| 2007/0213293 | A1* | 9/2007 | McSwiggen et al. ........... 514/44 |
| 2007/0231392 | A1 | 10/2007 | Wagner et al. |
| 2008/0038296 | A1 | 2/2008 | Brahmbhatt et al. |
| 2008/0107694 | A1 | 5/2008 | Trogden et al. |
| 2008/0112916 | A1 | 5/2008 | Wagner et al. |
| 2008/0152661 | A1 | 6/2008 | Rozema et al. |

FOREIGN PATENT DOCUMENTS

| | | |
|---|---|---|
| WO | WO 88/09810 | 12/1988 |
| WO | WO 89/10134 | 11/1989 |
| WO | WO 90/11364 | 10/1990 |
| WO | WO 90/14074 A1 | 3/1991 |
| WO | WO 91/16024 A1 | 10/1991 |
| WO | WO 91/17424 A1 | 11/1991 |
| WO | WO 92/03568 A1 | 3/1992 |
| WO | WO 97/42317 | 11/1997 |
| WO | WO 98/13526 A1 | 4/1998 |
| WO | WO 9904800 | 2/1999 |
| WO | WO 99/27133 | 6/1999 |
| WO | WO 99/54506 | 10/1999 |
| WO | WO 00/20040 | 4/2000 |
| WO | WO 2004033653 A2 | 4/2004 |
| WO | WO 2004/048545 A2 | 6/2004 |
| WO | WO 2004/065601 A2 | 8/2004 |
| WO | WO 2005001039 A2 | 1/2005 |
| WO | WO 2005111238 A2 | 11/2005 |
| WO | WO 2006086669 | 8/2006 |
| WO | WO 2007/089607 A2 | 8/2007 |
| WO | WO 2008/036825 A2 | 3/2008 |

OTHER PUBLICATIONS

Silverman, "Rube Goldberg Goes (RIBO)Nuclear? Molecular Switches and Sensors Made From RNA." 2003 RNA 9:377-383.
Winkler et al., "An mRNA Structure That Controls Gene Expression by Binding FMN." 2002 PNAS 99:15908-15913.
Winkler et al., "Genetic Control by Metabolite-Binding Riboswitches." 2003 ChemBioChem 4:1024-1032.
Al-Douahji et al., "The cyclin kinase inhibitor p21WAF1/C1P1 is required for glomerular hypertrophy in experimental diabetic nephropathy." 1999 Kidnev Int 56:1691-1699.
Banerjee et al., "Control of developmental timing by small temporal RNAs: a paradigm for RNA-mediated reaulation of gene expression." 2002 Bioessays 24:119-129.
Barrick et al., "New RNAa motifs suggest an expanded scope for riboswitches in bacterial genetic control." 2004 Proc Natl Acad Sci USA 101:6421-6426.
Bartel, "MicroRNAs: genomics, biogenesis, mechanism, and function." 2004 Cell 116:281-297.

Batzer et al., "Enhanced evolutionary PCR using oligonucleotides with inosine at the 3'-terminus." 1991 Nucleic Acids Res 19:5081.
Bayer et al., "Programmable ligand-controlled riboregulators of eukaryotic gene expression." 2005 Nat Biotechnol 23:337-343.
Been and Cech, "One binding site determines sequence specificity of Tetrahymena pre-rRNA self-splicing, trans-splicing, and RNA enzyme activity." 1986 Cell 47:207-216.
Benoist et al., "In vivo sequence requirements of the SV40 early promotor region." 1981 Nature 290:304-310.
Berens et al., "A tetracycline-binding RNA aptamer." 2001 Bioorg Med Chem 9:2549-2556.
Blind et al., "Cytoplasmic RNA modulators of an inside-out signal-transduction cascade." 1999 Proc Natl Acad Sci USA 96:3606-3610.
Brennecke et al., "Towards a complete description of the microRNA complement of animal genomes." 2003 Genome Biol 4:228.1-228.3.
Brinster et al., "Regulation of metallothionein-thymidine kinase fusion plasmids injected into mouse eggs." 1982 Nature 296:39-42.
Brummelkamp et al., "A system for stable expression of short interfering RNAs in mammalian cells." 2002 Science 296:550-553.
Buskirk et al., "Engineering a ligand-dependent RNA transcriptional activator." 2004 Chem Biol 11:1157-1163.
Caplen et al., "Specific inhibition of gene expression by small double-stranded RNAs in invertebrate and vertebrate systems." 2001 Proc Natl Acad Sci USA 98:9742-9747.
Caponigro et al., "A small segment of the MATa1 transcript promotes mRNA decay in Saccharomyces cerevisiae: a stimulatory role for rare codons." 1993 Mol Cell Biol 13:5141-5148.
Chen et al., "Synthesis of oligodeoxyribonucleotide N3' -> P5' phosphoramidates". 1995 Nucleic Acids Res 23:2661-2668.
Cox et al., "Automated selection of aptamers against protein targets translated in vitro: from gene to aptamer." 2002 Nucleic Acids Res 30:e108.
Dragun et al., "Inhibition of intercellular adhesion molecule-1 with antisense deoxynucleotides prolonos renal isograft survival in the rat." 1998 Kidnev Int 54:2113-2122.
Dragun et al., "ICAM-1 antisense oligodesoxynucleotides prevent reperfusion injury and enhance immediate graft function in renal transplantation." 1998 Kidnev Int 54:590-602.
Egholm et al., "PNA hybridizes to complementary oligonucleotides obeying the Watson-Crick hydrogen-bonding rules." 1993 Nature 365:566-568.
Elbashir et al., "Duplexes of 21-nucleotide RNAs mediate RNA interference in cultured mammalian cells." 2001 Nature 411:494-498.
Ellington et al., "In vitro selection of RNA molecules that bind specific ligands." 1990 Nature 346:818-822.
Famulok, "Oligonucleotide aptamers that recognize small molecules." 1999 Curr Opin Struct Biol 9:324-329.
Gardner et al., "Inferring genetic networks and identifying compound mode of action via expression profiling." 2003 Science 301:102-105.
Gautier et al., "α-DNA. IV: α-anomeric and β-anomeric tetrathymidylates covalently linked to intercalating oxazolopyridocarbazole. Synthesis, physicochemical properties and poly (rA) Binding." 1987 Nucleic Acids Res 15:6625-6641.
Gil et al., "Induction of apoptosis by the dsRNA-dependent protein kinase (PKR): mechanism of action." 2000 Apoptosis 5:107-114.
Good, "Diverse antisense mechanisms and applications." 2003 Cell Mol Life Sci 60:823-824.
Good, "Translation repression by antisense sequences." 2003 Cell Mol Life Sci 60:854-861.
Gouda et al., "Free energy calculations for theophylline binding to an RNA aptamer: Comparison of MM-PBSA and thermodynamic integration methods." 2003 Biopolymers 68:16-34.
Haller et al., "Antisense oligonucleotides for ICAM-1 attenuate reperfusion injury and renal failure in the rat." 1996 Kidnev Int 50:473-480.
Hamm et al., "Anti-idiotype RNA selected with an anti-nuclear export signal antibody is actively transported in oocytes and inhibits Rev- and cap-dependent RNA export." 1997 Proc Natl Acad Sci USA 94:12839-12844.
Haseloff et al., "Simple RNA enzymes with new and highly specific endoribonuclease activities." 1988 Nature 334:585-591.

(56) References Cited

OTHER PUBLICATIONS

Heidenreich et al., "RNase H-independent antisense activity of oligonucleotide N3' -> P5' phosphoramidates." 1997 Nucleic Acids Res 25:776-780.
Hermann et al., "Adaptive recognition by nucleic acid aptamers." 2000 Science 287:820-825.
Hesselberth et al., "Simultaneous detection of diverse analytes with an aptazyme ligase array." 2003 Anal Biochem 312:106-112.
Hirschbein et al., "31P NMR spectroscopy in oligonucleotide research and development." 1997 Antisense Nucleic Acid Drug Dev 7:55-61.
Huizenga et al., "A DNA aptamer that binds adenosine and ATP." 1995 Biochemistry 34:656-665.
Inoue et al., "Sequence-dependent hydrolysis of RNA using modified oligonucleotide splints and RNase H." 1987 FEBS Lett 215:327-330.
Inoue et al., "Synthesis and hybridization studies on two complementary nona(2'-O-methyl) ribonucleotides." 1987 Nucleic Acids Res 15:6131-6148.
Isaacs et al., "Engineered riboregulators enable post-transcriptional control of gene expression." 2004 Nat Biotechnol 22:841-847.
Jhaveri et al., "In vitro selection of signaling aptamers." 2000 Nat Biotechnol 18:1293-1297.
Jose et al., "Cooperative binding of effectors by an allosteric ribozyme." 2001 Nucleic Acids Res 29:1631-1637.
Kertsburg et al., "A versatile communication module for controlling RNA folding and catalysis." 2002 Nucleic Acids Res 30:4599-4606.
Khosla et al., "Metabolic engineering for drug discovery and development." 2003 Nat Rev Drug Discov 2:1019-1025.
Kim, "Small RNAs: classification, biogenesis, and function." 2005 Mol Cells 19:1-15.
Kipshidze et al., "Local delivery of c-myc neutrally charged antisense oligonucleotides with transport catheter inhibits myointimal hyperplasia and positively affects vascular remodeling in the rabbit balloon injury model." 2001 Catheter Cardiovasc Interv 54:247-256.
Kipshidze et al., "Intramural coronary delivery of advanced antisense oligonucleotides reduces neointimal formation in the porcine stent restenosis model." 2002 J Am Coll Cardiol 39:1686-1691.
Kobayashi et al., "Programmable cells: interfacing natural and engineered gene networks." 2004 Proc Natl Acad Sci USA 101:8414-8419.
Koch, "The metabolism of methylpurines by *Escherichia coli*. I. Tracer studies." 1956 J Biol Chem 219:181-188.
Koizumi et al., "Allosteric selection of ribozymes that respond to the second messengers cGMP and cAMP." 1999 Nat Struct Biol 6:1062-1071.
Kramer et al., "Role for antisense RNA in regulating circadian clock function in *Neurospora crassa*." 2003 Nature 421:948-952.
Kutryk et al., "Local intracoronary administration of antisense oligonucleotide against c-myc for the prevention of in-stent restenosis: results of the randomized investigation by the Thoraxcenter of antisense DNA using local delivery and IVUS after coronary stenting (Italics) trial." 2002 J Am Coll Cardiol 39:281-287.
Kuwabara et al., "Allosterically controllable ribozymes with biosensor functions." 2000 Curr Opin Chem Biol 4:669-677.
Kuwabara et al., "Allosterically controllable maxizyme-mediated suppression of progression of leukemia in mice." 2001 Biomacromolecules 2:1220-1228.
Kuwabara et al., "Allosterically controlled single-chained maxizymes with extremely high and specific activity." 2001 Biomacromolecules 2:788-799.
Lavorana et al., "In search of antisense." 2004 Trends Biochem Sci 29:88-94.
Lemaitre et al., "Specific antiviral activity of a pOly(L-lysine)-conjugated oligodeoxyribonucleotide sequence complementary to vesicular stomatitis virus N protein mRNA initiation site." 1987 Proc Natl Acad Sci USA 84:648-652.

Letsinger et al., "Cholesteryl-conjugated oligonucleotides: synthesis, properties, and activity as inhibitors of replication of human immunodeficiency virus in cell culture." 1989 Proc Natl Acad Sci USA 86:6553-6556.
Lilley, "The origins of RNA catalysis in ribozymes." 2003 Trends Biochem Sci 28:495-501.
Lorsch et al., "In vitro selection of RNA aptamers specific for cyanocobalamin." 1994 Biochemistry 33:973-982.
Mandal et al., "Adenine riboswitches and gene activation by disruption of a transcription terminator." 2004 Nat Struct Mol Biol 11:29-35.
Mannironi et al., "In vitro selection of dopamine RNA ligands." 1997 Biochemistry 36:97269734.
Mateus et al., "Destabilized green fluorescent protein for monitoring dynamic changes in yeast gene expression with flow cytometry." 2000 Yeast 16:1313-1323.
Mathews et al., "Incorporating chemical modification constraints into a dynamic programming algorithm for prediction of RNA secondary structure." 2004 Proc Natl Acad Sci USA 101:7287-7292.
McCaffrey et al., "RNA interference in adult mice." 2002 Nature 418:38-39.
McManus et al., "Gene silencing using micro-RNA desianed hairpins." 2002 RNA 8:842-850.
Nagai et al., "A variant of yellow fluorescent protein with fast and efficient maturation for cellbiological applications." 2002 Nat Biotechnol 20:87-90.
Nutiu et al., "Structure-switching signaling aptamers." 2003 J Am Chem Soc 125:4771-4778.
Ohtsuka et al., "An alternative approach to deoxyoligonucleotides as hybridization probes by insertion of deoxyinosine at ambiauous codon positions." 1985 J Biol Chem 260:2605-2608.
Paddison et al., "Stable suppression of gene expression by RNAi in mammalian cells." 2002 Proc Natl Acad Sci USA 99:1443-1448.
Paddison et al., "Short hairpin RNAs (shRNAs) induce sequence-specific silencing in mammalian cells." 2002 Genes Dev 16:948-958.
Perry-O'Keefe et al., "Peptide nucleic acid pre-gel hybridization: an alternative to Southern hybridization." 1996 Proc Natl Acad Sci USA 93:14670-14675.
Piganeau et al., "In vitro selection of allosteric ribozymes: theory and experimental validation." 2001 J Mol Biol 312:1177-1190.
Robertson et al., "Design and optimization of effector-activated ribozyme ligases." 2000 Nucleic Acids Res 28:1751-1759.
Rossolini et al., "Use of deoxyinosine-containing primers vs degenerate primers for polymerase chain reaction based on ambiguous sequence information." 1994 Moll Cell Probes 8:91-98.
Roth et al., "Selection in vitro of allosteric ribozymes." 2004 Methods Mol Biol 252:145-164.
Samarsky et al., "A small nucleolar RNA:ribozyme hybrid cleaves a nucleolar RNA target in vivo with near-perfect efficiency." 1999 Proc Natl Acad Sci USA 96:6609-6614.
Sarver et al., "Ribozymes as potential anti-HIV-1 therapeutic agents." 1990 Science 247:1222-1225.
Scherer et al., "Recent applications of RNAi in mammalian systems." 2004 Curr Pharm Biotechnol 5:355-360.
Scherer et al., "Approaches for the sequence-specific knockdown of mRNA." 2003 Nat Biotechnol 21:1457-1465.
Smolke et al., "Coordinated, differential expression of two genes through directed mRNA cleavage and stabilization by secondary structures." 2000 Appl Environ Microbiol 66:5399-5405.
Soukup et al., "Altering molecular recognition of RNA aptamers by allosteric selection." 2000 J Mol Biol 298:623-632.
Soukup et al., "Generating new ligand-binding RNAs by affinity maturation and disintegration of allosteric ribozymes." 2001 RNA 7:524-536.
Soukup et al., "Design of allosteric hammerhead ribozymes activated by ligand-induced structure stabilization." 1999 Structure 7:783-791.
Stein et al., "Oligodeoxynucleotides as inhibitors of gene expression: a review." 1988 Cancer Res 48:2659-2668.
Stojanovic et al., "Modular aptameric sensors." 2004 J Am Chem Soc 126:9266-9270.
Sui et al., "A DNA vector-based RNAi technology to suppress gene expression in mammalian cells." 2002 Proc Natl Acad Sci USA 99:5515-5520.

(56) References Cited

OTHER PUBLICATIONS

Taira et al., "Construction of a novel RNA-transcript-trimming plasmid which can be used both in vitro in place of run-off and (G)-free transcriptions and in vivo as multi-sequences transcription vectors." 1991 Nucleic Acids Res 19:5125-5130.
Tang et al., "Rational design of allosteric ribozymes." 1997 Chem Biol 4:453-459.
Tuerk et al., "Systematic evolution of ligands by exponential enrichment: RNA ligands to bacteriophage T4 DNA polymerase." 1990 Science 249:505-510.
Vacek et al., "Antisense-mediated redirection of mRNA splicing." 2003 Cell Mol Life Sci 60:825-833.
van der Krol et al., "Modulation of eukaryotic gene expression by complementary RNA or DNA sequences." 1988 Biotechniques 6:958-976.
Wagner et al., "Nucleotide sequence of the thymidine kinase gene of *Herpes simplex virus* type 1." 1981 Proc Natl Acad Sci USA 78:1441-1445.
Wagner, "Gene inhibition using antisense oligodeoxynucleotides." 1994 Nature 372:333-335.
Wang et al., "A general approach for the use of oligonucleotide effectors to regulate the catalysis of RNA-cleaving ribozymes and DNAzymes." 2002 Nucleic Acids Res 30:1735-1742.
Wang et al., "A general strategy for effector-mediated control of RNA-cleaving ribozymes and DNA enzymes." 2002 J Mol Biol 318:33-43.
Watkins et al., "Metabolomics and biochemical profiling in drug discovery and development." 2002 Curr Opin Mol Ther 4:224-228.
Weiss et al., "Antisense RNA gene therapy for studying and modulating biological processes." 1999 Cell Mol Life Sci 55:334-358.
Werstuck et al., "Controlling gene expression in living cells through small molecule-RNA interactions." 1998 Science 282:296-298.
Wilda et al., "Killing of leukemic cells with a BCRIABL fusion gene by RNA interference I (RNAi)." 2002 Oncogene 21:5716-5724.
Wilson et al., "The interaction of intercalators and groove-binding agents with DNA triplehelical structures: the influence of ligand structure, DNA backbone modifications and sequence." 1994 J Mol Recognit 7:89-98.
Winkler et al., "Control of gene expression by a natural metabolite-responsive ribozyme." 2004 Nature 428:281-286.
Winkler et al., "Thiamine derivatives bind messenger RNAs directly to regulate bacterial gene expression." 2002 Nature 419:952-956.
Yamamoto et al., "Identification of a functional promoter in the long terminal repeat of *Rous sarcoma virus*." 1980 Cell 22:787-797.
Yelin et al., "Widespread occurrence of antisense transcription in the human genome." 2003 Nat Biotechnol 21:379-386.
Yen et al., "Exogenous control of mammalian gene expression through modulation of RNA self-cleavage." 2004 Nature 431:471-476.
Yu et al., "RNA interference by expression of short-interfering RNAs and hairpin RNAs in mammalian cells." 2002 Proc Natl Acad Sci USA 99:6047-6052.
Zaug et al., "A labile phosphodiester bond at the ligation junction in a circular intervening sequence RNA." 1984 Science 224:574-578.
Zaug et al., "The intervening sequence RNA of Tetrahymena is an enzyme." 1986 Science 231:470-475.
Zaug et al., "The Tetrahymena ribozyme acts like an RNA restriction endonuclease." 1986 Nature 324:429-433.
Zimmermann et al., "Interlocking structural motifs mediate molecular discrimination by a theophylline-binding RNA." 1997 Nat Struct Biol 4:644-649.
Zimmermann et al., "Molecular interactions and metal binding in the theophylline-binding core of an RNA aptamer." 2000 RNA 6:659-667.
Zon, "Oligonucleotide analogues as potential chemotherapeutic agents." 1988 Pharm Res 5:539-549.
Vuyisich et al., "Controlling protein activity with ligand-regulated RNA aptamers." 2002 Chemistry & Biology, 9:907-913.
Agrawal et al., "RNA interference: biology, mechanism, and applications." 2003 Microbiology and Molecular Biology Reviews, 67:657-685.
Soukup et al., "Nucleic acid molecular switches." 1999 Trends in Biotechnology 17:469-476.
Carmell et al., "RNase III enzymes and the initiation of gene silencing." 2004 Nature Structural & Molecular Biology, 11:214-218.
An et al., "Artificial control of gene expression in mammalian cells by modulating RNA interference through aptamer-small molecule interaction." 2006, RNA 12(5):710-716.
Bauer G. et al., "Engineered riboswitches as novel tools in molecular biology." 2006, Journal of Biotechnology 124(1):4-11.
Berezovski et al., "Nonequilibrium Capillary Electrophoresis of Equilibrium Mixtures: A Universal Tool for Development of Aptamers." 2005, J. Am. Chem. Soc. 127:3165-3171.
Davidson et al., "Synthetic RNA circuits." 2007, Nature Chemical Biology 3(1):23-28.
Desai et al., "Genetic screens and selections for small molecules based on a synthetic riboswitch that activates protein translation." 2004, Journal of the American Chemical Society 126:13247-13254.
Drabovich et al., "Selection of Smart Aptamers by Equilibrium Capillary Electrophoresis of Eauilibrium Mixtures (ECEEM)." 2005 J. Am. Chem. Soc. 127:11224-11225.
Isaacs et al., "RNA synthetic biology." 2006 Nature Biotechnology 24(5):545-554.
John J. Rossi, "Targeted cleavage: Tuneable cis-cleaving ribozymes." 2007 PNAS 104(38):14881-14882.
Mendonsa et al., "In Vito Evolution of Functional DNA Using Capillarv Electrophoresis." 2004 J. Am. Chem. Soc. 126:20-21.
Mendonsa et al., "In Vitro Selection of Aptamers with Affinity for Neuropeptide Y Using D Capillary Electrophoresis." 2005 J. Am. Chem. Soc. 127:9382-9383.
Mendonsa et al., "In Vitro Selection of High-Affinity DNA Ligands for Human IgE Using Capillary Electrophoresis." 2004 Anal. Chern. 76:5387-5392.
Smolke et al., "Molecular Switches for Cellular Sensors." 2005 Engineering & Science 67(4):28-37.
Sudarsan et al., "Tandem riboswitch architectures exhibit complex gene control functions." 2006 Science 314(5797):300-304.
Suess et al., "A theophylline responsive riboswitch based on helix slipping contois gene expression in vivo." 2004 Nucleic Acids Research. 32(4):1610-1614.
Yokobayashi et al., "Directed evolution of a genetic circuit." 2002 Proc Natl Acad Sci USA 99:16587-16591.
Basu et al., "Spatiotemporal control of gene expression with pulse-generatinq networks." 2004 Proc Natl Acad Sci USA 101:6355-6360.
Levine et al., "Quantitative Characteristics of Gene Regulation by Small RNA." 2007 PLoS Biol 5(e229):1998-2010.
Hebert et al., "Loss of microRNA cluster miR-29a/b-1 in sporadic Alzheimer's disease correlates with increased BACE1-β-secretase expression." 2008 Proc Natl Acad Sci USA 105:6415-6420.
Calin et al., "MiR-15a and miR-16-1 cluster functions in human leukemia." 2008 Proc Natl Acad Sci USA 105:5166-5171.
Ventura et al., "Targeted Deletion Reveals Essential and Overlapping Functions of the miR-17~92 Family of miRNA Clusters." 2008 Cell 132:875-886.
Welz et al., "Ligand binding and gene control characteristics of tandem riboswitches in *Bacillus anthracis*." 2007 RNA 13:573.
Rodionov et al., "Reconstruction of regulatory and metabolic pathways in metal-reducing δ-proteobacteria." 2004 Genome Biol 5:R90. 1-R90.27.
Rinaudo et al., "A universal RNAi-based logic evaluator that operates in mammalian cells." 2007 Nat Biotechnol 25:795-801.
Deans et al., "A Tunable Genetic Switch Based on RNAi and Repressor Proteins for Regulating Gene Expression in Mammalian Cells." 2007 Cell 130:363-372.
Berge et al., "Pharmaceutical Salts." 1977 J. of Pharm Sci. 66:1-19.
Guet et al., "Combinatorial synthesis of genetic networks." 2002 Science 296:1466-1470.
Kramer et al.," BioLogic gates enable logical transcription control in mammalian cells." 2004 Biotechnol Bioeng 87:478-484.
Cox et al., "Programming gene expression with combinatorial promoters." 2007 Mol Syst Biol 3:145.

(56) References Cited

OTHER PUBLICATIONS

Anderson et al., "Environmental signal integration by a modular AND gate." 2007 Mol Syst Biol 3:133.
Seelig et al.,"Enzyme-Free Nucleic Acid Logic Circuits." 2006 Science 314:1585-1588.
Benenson et al., "An autonomous molecular computer for logical control of gene expression." 2004 Nature 429:423-429.
Dirks et al., "Triggered amplification by hybridization chain reaction." 2004 Proc Natl Acad Sci USA 101:15275-15278.
Stojanovic et al., "A deoxyribozyme-based molecular automaton." 2003 Nat Biotechnol 21:1069-1074.
Penchovsky et al., "Computational design and experimental validation of oligonucleotide-sensing allosteric ribozymes." 2005 Nat Biotechnol 23:1424-1433.
Breaker, "Engineered allosteric ribozymes as biosensor components." 2002 Curr Opin Biotechnol 13:31-39.
Robertson et al., "In vitro selection of an allosteric ribozyme that transduces analytes to amplicons." 1999 Nat Biotechnol 17:62-66.
Suess et al., "Engineered riboswitches: overview, problems and trends." 2008 RNA Biol 5(1):1-6.
Brown et al., "Endogenous microRNA can be broadly exploited to regulate transgene expression according to tissue, lineage and differentiation state." 2007 Nat Biotechnol 25:1457-1467.
Parisien et al.,"The MC-Fold and MC-Sym pipeline infers RNA structure from sequence data." 2008 Nature 452:51-55.
Mathews et al., "Prediction of RNA secondary structure by free energy minimization." 2006 Curr Opin Struct Biol 16:270-278.
Khvorova et al., "Sequence elements outside the hammerhead ribozyme catalytic core enable intracellular activity." 2003 Nat Struct Biol 10:708-872.
Mandal et al., "A glycine-dependent riboswitch that uses cooperative binding to control gene expression." 2004 Science 306:275-279.
Woodside et al., "Nanomechanical measurements of the sequence-dependent folding landscapes of single nucleic acid hairpins." 2006 Proc Natl Acad Sci USA 103:6190-6195.
Stein et al., "Physicochemical properties of phosphorothioate oligodeoxynucleotides." 1988 Nucl. Acids Res. 16:3209-3221.
Sarin et al., "Inhibition of acquired immunodeficiency syndrome virus by oligodeoxynucleoside methylphosphonates." 1988 Proc. Natl. Acad. Sci. USA 85:7448-7451.
MacRae et al., "Structural Basis for Double-Stranded RNA Processing by Dicer." 2006 Science 311( 5758):195-198.
Zeng and Cullen, "Structural requirements for pre-microRNA binding and nuclear export by Exportin 5." 2004 Nucleic Acids Res. 32(16):4776-85.
Griffiths-Jones, "The microRNA Registry." 2004 Nucleic Acids Res. 32:D109-111.
Griffiths-Jones et al., "MiRBase: microRNA sequences, targets and gene nomenclature." 2006 Nucleic Acids Res. 34:D140-144.
Soukup and Breaker, "Relationship between internucleotide linkage geometry and the stability of RNA." 1999 RNA 5:1308-1325.
Abbas-Terki et al., "Lentiviral-mediated RNA interference." 2002 Hum Gene Ther 13: 2197-2201.
Hutvagner et al., "Sequence-specific inhibition of small RNA function." 2004 PLoS Biol 2: E98.
Meister, "Sequence-specific inhibition of microRNA- and siRNA-induced RNA silencing." 2004 RNA 10:544-550.
Bartlett and Davis, "Insights into the kinetics of siRNA-mediated gene silencing from live-cell and live-animal bioluminescent imaging." 2006 Nucleic Acids Res 34:322-333.
Malphettes and Fussenegger, "Impact of RNA interference on gene networks." 2006 Metab Eng 8:672-683.
Raab and Stephanopoulos, "Dynamics of gene silencing by RNA interference." 2004 Biotechnol Bioeng 88:121-132.
Kiga et al., "An RNA aptamer to the xanthine-guanine base with a distinctive mode of purine recognition." 1998 Nucleic Acids Res 26:1755-1760.
Thompson et al., "Group I aptazymes as genetic regulatory switches." 2002 BMC Biotechnol 2:21.

Suel et al., "Tunability and noise dependence in differentiation dynamics." 2007 Science 315:1716-1719.
Gardner et al., "Construction of a genetic toggle switch in *Escherichia coli*." 2000 Nature 403:339-342.
Yi et al., "Exportin-5 mediates the nuclear export of premicroRNAs and short hairpin RNAs." 2003 Genes Dev 17:3011-3016.
Ketting et al., "Dicer functions in RNA interference and in synthesis of small RNA involved in developmental timing in *C. elegans*." 2001 Genes Dev 15:2654-2659.
Gregory et al., "Human RISC couples microRNA biogenesis and posttranscriptional gene silencing." 2005 Cell 123:631-640.
Kok et al., "Human TRBP and PACT directly interact with each other and associate with dicer to facilitate the production of small interfering RNA." 2007 J Biol Chem 282:17649-17657.
Lee et al., "The role of PACT in the RNA silencing pathway." 2006 EMBO J 25:522-532.
Matranga et al., "Passenger-strand cleavage facilitates assembly of siRNA into Ag02-containing RNAi enzyme complexes." 2005 Cell 123:607-620.
Rand et al., "Argonaute2 cleaves the anti-guide strand of siRNA during RISC activation." 2005 Cell 123:621-629.
Westerhout and Berkhout, "A systematic analysis of the effect of target RNA structure on RNA interference." 2007 Nucleic Acids Res. 35(13):4322-4330.
Grimm et al., "Fatality in mice due to oversaturation of cellular microRNNshort hairpin RNA pathways." 2006 Nature 441:537-541.
Yi et al., "Overexpression of exportin 5 enhances RNA interference mediated by short hairpin RNAs and microRNAs." 2005 RNA 11:220-226.
Danilova et al., "RNAKinetics: a web server that models secondary structure kinetics of an elongating RNA." 2006 J Bioinform Comput Biol 4:589-596.
Croft et al., "Is prokaryotic complexity limited by accelerated growth in regulatory overhead?" 2003 Genome Biology 5:P2.
Dueber et al., "Engineering synthetic signaling proteins with ultrasensitive input-output control." 2007 Nat Biotechnol 25:660-662.
Elowitz and Leibler, "A synthetic oscillatory network of transcriptional regulators." 2000 Nature 403:335-338.
Flotte, "Size does matter: overcoming the adeno-associated virus packaging limit." 2000 Respir Res 1:16-18.
Grate and Wilson, "Inducible regulation of the *S. cerevisiae* cell cycle mediated by an RNA aptamer-ligand complex." 2001 Bioorg Med Chem 9:2565-2570.
Grieger and Samulski, "Packaging capacity of adeno-associated virus serotypes: impact of larger genomes on infectivity and postentry steps." 2005 J Virol 79:9933-9944.
Grundy and Henkin, "From ribosome to riboswitch: control of gene expression in bacteria by RNA structural rearrangements." 2006 Crit Rev Biochem Mol Biol 41:329-338.
Hall et al., "Computational selection of nucleic acid biosensors via a slip structure model." 2007 Biosens Bioelectron 22:1939-1947.
Hooshangi et al., "Ultrasensitivity and noise propagation in a synthetic transcriptional cascade." 2005 Proc Natl Acad Sci USA 102: 3581-3586.
Huang and Ferrell, "Ultrasensitivity in the mitogen-activated protein kinase cascade." 1996 Proc Natl Acad Sci USA 93: 10078-10083.
Jenison et al., "High-resolution molecular discrimination by RNA." 1994 Science 263:1425-1429.
Lee et al., "Aptamer database." 2004 Nucleic Acids Res 32:D95-100.
Lynch et al., "A high-throughput screen for synthetic riboswitches reveals mechanistic insights into their function." 2007 Chem Biol 14:173-184.
Ogawa and Maeda,"An artificial aptazyme-based riboswitch and its cascading system in *E. coli*." 2008 Chembiochem 9:206-209.
Shalgi et al., "Global and Local Architecture of the Mammalian microRNA-Transcription Factor Regulatory Network." 2007 PLoS Comput Biol 3:e131.
Sudarsan et al., "Metabolite-binding RNA domains are present in the genes of eukaryotes." 2003 RNA 9:644-647.
Suess et al.,"Conditional gene expression by controlling translation with tetracycline-binding aptamers." 2003 Nucleic Acids Res 31:1853-1858.

(56) References Cited

OTHER PUBLICATIONS

Weigand and Suess, "Tetracycline aptamer-controlled regulation of pre-mRNA splicing in yeast." 2007 Nucleic Acids Res 35:4179-4185.
Wieland and Hartig, "Improved aptazyme design and in vivo screening enable riboswitching in bacteria." 2008 Angew Chern Int Ed Eng147:2604-2607.
Javaherian et al., "Selection of aptamers for a protein target in cell lysate and their application to protein purification." 2009 Nucleic Acids Res. 37(8):e62.
Yunusov et al., "Kinetic capillary electrophoresis-based affinity screening of aptamer clones." 2009 Anal Chim Acta. 631(1):102-7.
Amarzguioui et. al., "Tolerance for mutations and chemical modifications in a siRNA." *Nucleic Acid Research* 31: 589-595, 2003.
Chiu & Rana, "RNAi in Human Cells: Basic Structural and Functional Features of Small Interfering RNA." Mol. Cell 10: 549-561,2002.
Chiu & Rana, "siRNA function in RNAi: A chemical modification analysis." RNA 9: 1034-1048,2003.
Geiger, Burgstaller et al., "RNA aptamers that bind L-arginine with sub-micromolar dissociation constants and high enantioselectivity." Nucleic Acids Research vol. 24, Issue 6, 1029-1036.
Hamada et al., "Effects on RNA Interference in Gene Expression (RNAi) in Cultured Mammalian Cells of Mismatches and the Introduction of Chemical Modifications at the 3'-Ends of siRNAs." *Antisense Nucleic Acid Drug Dev.* 12(5): 301-309,2002.
Harborth et al., "Sequence, Chemical, and Structural Variation of Small Interfering RNAs and Short Hairpin RNAs and the Effect on Mammalian Gene Silencing. "*Antisense Nucleic Acid Drug Dev.* 13(2): 83-105,2003.
Hwang et al.,"A Hexanucleotide Element Directs MicroRNA Nuclear Import." *Science* 315: 97-100, 2007.
Kim et al., "Synthetic dsRNA Dicer substrates enhance RNAi potency and efficacy."*Nature Biotech*. 23: 222-226, 2008.
Lescoute and Westhof, "Topology of three-way junctions in folded RNAs." *RNA* 12: 83-93, 2006.
Li and Breaker, "Kinetics of RNA Degradation by Specific Base Catalysis of Transesterification Involving the 2'-Hydroxyl Group." *J Am. Chem. Soc.* 121: 5364-5372, 1999.
McBride et al., "Artificial miRNAs mitigate shRNA-mediated toxicity in the brain: Implications for the therapeutic development of RNAi."*PNAS* 105: 5868, 2008.
Nickols et al., "Suppression of androgen receptor-mediated gene expression by a sequence-specific DNA-binding polyamide."*Proc. Natl. Acad. Sci. USA* 104: 10418-10423,2007.
Ohrt et al., "Fluorescence correlation spectroscopy and fluorescence cross-correlation spectroscopy reveal the cytoplasmic origination of loaded nuclear RISC in vivo in human cells."*Nucleic Acids Res.* 36(20): 6439-6449, 2008.
Schwarz et. al., "Evidence that siRNAs Function as Guides, Not Primers, in the *Drosophila* and Human RNAi Pathways." Mol. Cell 10: 537-548, 2002.
Soukup and Soukup, "Riboswitches exert genetic control through metabolite-induced conformational change." Current Opinions in Structural Biology 14: 344, 2004.
Zhou et al., "Novel Dual Inhibitory Function Aptamer—siRNA Delivery System for HIV-1 Therapy."*Molecular Therapy* 16: 1481-1489,2008.
Beisel et al., "Model-guided design of ligand-regulated RNAi for programmable control of gene expression." 2008, Molecular Systems Biology 4:224.
Win et al., "A modular and extensible RNA-based gene-regulartory platform for engineering cellular function." 2007 PNAS 104(36):14283-14288.
Win et al., "RNA as a Versatile and Powerful Platform for Engineering Genetic Regulartory Tools." 2007 Biotechnoloay and Genetic Engineering Reviews 24:311-346.
Berens et al., "Synthetic riboregulators—an alternative means to control gene expression" 2005 Gene Therapy and Molecular Biology 9:417-422.

Chen et al., "Genetic control of mammalian T-cell proliferation with synthetic RNA regulatory systems." 2010 Proc. Natl. Acad. Sci. USA. 107: 8531-6.
Culler et al., "Functional selection and systematic analysis of intronic splicing elements identifies active sequence motifs and associated splicing factors." 2010 Nuc. Acids Res. 38: 5152-65.
Hoff et al., "In vivo fluorescent detection of Fe—S clusters coordinated by human GRX2." 2009 Chem. Biol. 16: 1299-308.
Smolke, "Building outside of the box: iGEM and the BioBricks Foundation." 2009 Nat. Biotech. 27:1099-102.
Smolke, "It's the DNA that counts." 2009 Science. 324: 1156-7.
Beisel et al., "Design principles for riboswitch function." 2009 PLoS Comp. Biol. 5: e1000363.
Win et al., "Frameworks for programming biological function through RNA parts and devices." 2009 Chem. Biol. 16: 298-310.
Bayer et al., "Synthetic control of a fitness tradeoff in yeast nitrogen metabolism." 2009 J. Biol. Eng. 3: 1.
Hoff et al., "Fluorescence detection of a protein-bound 2Fe2S cluster." 2009 Chembiochem. 10: 667-70.
Hawkins et al., "Production of benzylisoquinoline alkaloids in *Saccharomyces cerevisiae*." 2008 Nat. Chem. Biol. 4: 564-73.
Benenson, "Small hairpin RNA as a small molecule sensor." 2008 Mol. Sys. Biol. 4: 227.
Keasling, "From yeast to alkaloids." 2008 Nat. Chem. Biol. 4: 524-5.
Win et al., "Higher-order cellular information processing with synthetic RNA devices." 2008 Science. 322: 456-60.
Shapiro et al., "RNA computing in a living cell." 2008 Science. 322: 387-8.
Baker et al., "Engineering life: building a Fab for biology." 2006 Scientific American. 294: 44-51.
Win et al., "Codeine-binding RNA aptamers and rapid determination of their binding constants using a direct coupling surface plasmon resonance assay." 2006 Nuc. Acids Res. 34: 5670-82.
Pfleger et al., "Combinatorial engineering of intergenic regions in operons tunes expression of multiple genes." 2006 Nat. Biotech. 24: 1027-32.
Hawkins et al., "The regulatory roles of the galactose permease and kinase in the induction response of the GAL network in *Saccharomyces cerevisiae*." 2006 J. Biol. Chem. 281: 13485-92.
Isaacs et al., "Plug and play with RNA." 2005 Nat. Biotech. 23: 306-7.
Martin et al., "Redesigning cells for the production of complex organic molecules." 2002 ASM News 68: 336-43.
Smolke et al., "Effect of gene location, mRNA secondary structures, and Rnase sites on expression of two genes in an engineered operon." 2002 Biotech. Bioeng. 80: 762-76.
Smolke et al., "Effect of copy number and mRNA processing and stabilization on transcript and protein levels from an engineered dual-gene operon." 2002 Biotech. Bioeng. 78: 412-24.
Smolke et al., "Effects of transcription induction homogeneity and transcript stability on expression of two genes in a constructed operon." 2001 Appl. Micro. Biotech. 57: 689-96.
Smolke et al., "Controlling the metabolic flux through the carotenoid pathway using directed mRNA processing and stabilization." 2001 Met. Eng. 3: 313-21.
Duconge and Toulme, "In vitro selection identifies key determinants for loop-loop interactions: RNA aptamers selective for the TAR RNA element of HIV-1." 1999 RNA 5: 1605-1614.
Aagaard et al., "Engineering and optimization of the miR-1 06b cluster for ectopic expression of multiplexed anti-HIV RNAs." Gene Ther (2008); 15: 1536-1549.
Bauer et al., "Prevention of interferon-stimulated gene expression using microRNA-designed hairpins." Gene Ther. (2009); 16: 142-147.
Baulcombe, "Diced defence." Nature. Jan. 18, 2001; 409(6818):295-6.
Biesecker et al, "Derivation of RNA aptamer inhibitors of human complement C5." Immunopharmacology (1999) vol. 42, Issue 1-3, pp. 219-30.
Boiziau et al. "DNA Aptamers Selected Against the HIV-1 trans-Activationresponsive RNA Element Form RNA-DNA Kissing Complexes." Journal of biological chemistry (1999); 274(18): 12730-12737.

(56) References Cited

OTHER PUBLICATIONS

Boiziau et al., "Identification of Aptamers Against the DNA Template for In Vitro Transcription of the HIV-1 TAR Element." Antisense Nucleic Acid Drug Dev. (1997); 7(4): 369-80.
Boudreau et al., "Artificial microRNAs as siRNA shuttles: improved safety as compared to shRNAs in vitro and in vivo." Mol. Ther. (2009); 17(1): 169-175.
Brockstedt et al., "In vitro evolution of rna aptamers recognizing carcinogenic aromatic amines." Biochem. Biophys. Res. Commun. (2004) vol. 313, Issue 4, pp. 1004-1008.
Burke et al., "RNA aptamers to the adenosine moiety of S-adenosyl methionine: structural inferences from variations on a theme and the reproducibility of SELEX." Nucleic Acids Research (1997); 25(10): 2020-2024.
Cai et aal., "Human microRNAs are processed from capped, polyadenylated transcripts that can also function as mRNAs." RNA (2004); 10: 1957-1966.
Daniels, "A tenascin-C aptamer identified by tumor cell SELEX: Systematic evolution of ligands by exponential enrichment." PNAS (2003); 100(26): 15416-15421.
Eulberg et al., "Development of an automated in vitro selection protocol to obtain RNA-based aptamers: identification of a biostable substance P antagonist." Nucleic Acids Res. (2005); 33(4): e45.
Flinders et al., "Recognition of planar and nonplanar ligands in the malachite green-rna aptamer complex." Chembiochem (2004) vol. 5, Issue I, pp. 62-72.
Friedman et al., "Most mammalian mRNAs are conserved targets of microRNAs." Genome Res. (2009); 19: 92-105.
Fukusaki et al., "DNA aptamers that bind to chitin." Bioorg. Med. Chem. Lett. (2000) vol. 10, Issue 5, pp. 423-425.
Gebhardt, "RNA aptamers to s-adenosylhomocysteine: kinetic properties, divalent cation dependency, and comparison with anti-s-adenosylhomocysteine antibody." Biochemistry (2000) vol. 39, Issue 24, pp. 7255-7265.
Gilbert et al. "RNA aptamers that specifically bind to a k ras-derived farnesylated peptide." Bioorg. Med. Chem. (1997) vol. 5, Issue 6, pp. 1115-1122.
Gopinath et al., "An efficient rna aptamer against human influenza b virus hemagglutinin." J Biochem (Tokyo) (2006) vol. 139, Issue 5, pp. 837-846.
Gregory et al., "The Microprocessor complex mediates the genesis of microRNAs." Nature (2004). 432,235-240.
Guil et al., "The multifunctional RNA-binding protein hnRNP Al is required for processing of miR-18a." Nat Struct Mol Biol (2007). 14: 591-596.
Haller et al., "In vitro selection of a 7-methyl-guanosine binding RNA that inhibits translation of capped mRNA molecules." PNAS (1997); 94: 8521-8526.
Hammond et al., "Argonaute2, a Link Between Genetic and Biochemical Analyses of RNAi." Science. Aug. 10, 2001; 293(5532): 1146-1150.
Han et al., "Molecular basis for the recognition of primary microRNAs by the Drosha-DGCR8 complex." Cell (2006); 125: 887-901.
Han et al., "The Drosha-DGCR8 complex in primary microRNA processing." Genes Dev (2004); 18: 3016-3027.
Han et al., "Posttranscriptional crossregulation between Drosha and DGCR8." Cell (2009); 136: 75-84.
Hesselberth et al., "In Vitro Selection of RNA Molecules That Inhibit the Activity of Ricin A-chain." Journal of Biological Chemistry (2000); 275(7): 4937-4942.
Hicke et al., "Tenascin-C Aptamers Are Generated Using Tumor Cells and Purified Protein." J. Biol. Chem. (2001); 276(52): 48644-4854.
Hirao et al., "RNA Aptamers That Bind to and Inhibit the Ribosome-inactivating Protein, Pepocin." Journal of Biological Chemistry (2000); 275(7): 4943-4948.
Hornung et al., "In vitro selected rna molecules that bind to elongation factor tu." Biochemistry (1998) vol. 37, Issue, pp. 7260-7267.
Jeong et al., "In vitro selection of the rna aptamer against the sialyl lewis x and its inhibition of the cell adhesion." Biochemical and Biophysical Research Communications (2001) vol. 281, Issue I, pp. 237-243.
Kato et al., "In vitro selection of dna aptamers which bind to cholic acid." Biochim. Biophys. Acta (2000) vol. 1493, Issue 1-2, pp. 12-18.
Kedde et al., "RNA-binding protein Dndl inhibits microRNA access to target mRNA." Cell (2007); 131: 1273-1286.
Kimoto et al., "Anti-(Raf-1) RNA aptamers that inhibit Ras-induced Raf-1 activation." Eur. J. Biochem. (2002); 269(2): 697-704.
Kimoto et al., "RNA aptamers that specifically bind to the Ras-binding domain of Raf-1." FEBS Lett. (1998); 441(2): 322-326.
Koizumi et al., "Molecular recognition of cAMP by an RNA aptamer." Biochemistry (2000) vol. 39, Issue 30, pp. 8983-8992.
Zeng et al., "Recognition and cleavage of primary microRNA precursors by the nuclear processing enzyme Drosha." EMBO J. (2005); 24: 138-148.
Kraus et al, "Cutting Edge: Novel RNA Ligands Able to Bind CD4 Antigen and Inhibit CD41 T Lymphocyte Function." J. Immunol. (1998); 160(II): 5209-5212.
Lee et al., "The nuclear RNase III Drosha initiates microRNA processing." Nature (2003) 425:415-419.
Lee et al., "In vitro and in vivo assays for the activity of Drosha complex." Methods Enzymol (2007).427: 89-106.
Lee et al., "MicroRNA maturation: stepwise processing and subcellular localization." EMBO J. (2002); 21(17): 4663-4670.
Legiewicz et al., "A More Complex Isoleucine Aptamer with a Cognate Triplet." J. Biol. Chem. (2005); 280(20): 19815-19822.
Liu, et al., "RNA aptamers specific for bovine thrombin." Journal of Molecular Recognition (2003) vol. 16, Issue 1, pp. 23-27.
Lozupone et al., "Selection of the simplest RNA that binds isoleucine." RNA (2003); 9(II): 1315-22.
Misono et al. "Selection of RNA aptamers against human influenza virus hemagglutinin using surface plasmon resonance." Anal. Biochem. (2005) vol. 342, Issue 2, pp. 312-317.
Muller et al., "Thermodynamic characterization of an engineered tetracycline-binding riboswitch." Nucleic Acids Res (2006); 34(9): 2607-2617.
Osborne et al., "Nucleic Acid Selection and the Challenge of Combinatorial Chemistry." Chern. Rev (1997). 97: 349-370.
Roychowdhury-Saha et al., "Flavin recognition by an RNA aptamer targeted toward FAD." Biochemistry (2002) vol. 41, Issue 8, pp. 2492-2499.
Ruckman, et al., "2'-Fluoropyrimidine RNA-based Aptamers to the 165-Amino Acid Form of Vascular Endothelial Growth Factor (VEGF165)." J. Biol. Chem. (1998); 273(32): 20556-20567.
Saran et al., "The tyranny of adenosine recognition among RNA aptamers to coenzyme A." BMC Evol. Biol. (2003); 3(I): 26.
Schneider et al, "Selective enrichment of RNA species for tight binding to Escherichia coli rho factor." FASEB J. (1993) 7(I): 201-207.
Sontheimer, "Assembly and Function of RNA Silencing Complexes." Nat Rev Mol Cell Biol. Feb. 2005; 6(2):127-38.
Stern et al., "A system for Cre regulated RNA interference in vivo." Proc Natl Acad Sci USA (2008); 105, 13895-13900.
Sun et al., "Multi-miRNA hairpin method that improves gene knockdown efficiency and provides coupled multi-gene knockdown." Biotechniques (2006); 41: 59-63.
Tahiri-Alaoui et al., "High affinity nucleic acid aptamers for strptavidin incorporated into bi-specific capture ligands." Nucleic Acids Res. (2002); 30(10): e45.
Takeno et al., "Selection of an RNA Molecual That Specifically Inhibits the Protease Activity of Subtilisin." Journal of Biochemistry (1999); 125(6): 1115-1119.
Tao et al., "Arginine-binding rnas resembling tar identified by in vitro selection." Biochemistry (1996) vol. 35, Issue 7, pp. 2229-2238.
Ruscono et al., "Blocking the initiation of coagulation by rna aptamers to factor viia." Thromb Haemost. (2000) vol. 84, Issue 5, pp. 841-848.
Tuerk et al., "RNA pseudoknots that inhibit human immunodeficiency virus type 1 reverse transcriptase." Proc Natl Acad Sci USA (1992); 89:6988-6992.

(56) References Cited

OTHER PUBLICATIONS

Tuleuova et al., "Modulating endogenous gene expression of mammalian cells via RNA-small molecule interaction." Biochem Biophys Res Commun (2008); 376: 169-173.

Ulrich et al., "In vitro selection of RNA molecules that displace cocaine from the membrane-bound nicotinic acetylcholine receptor." Proc. Natl. Acad. Sci. USA (1998); 95(24): 14051-14056.

Urvil et al., "Selection of RNA aptamers that bind specifically to the NS3 protease of hepatitis C virus." European Journal of Biochemistry (1997); 248(I): 130-138.

Vaish et al., "A novel, modification-dependent ATP-binding aptamer selected from an rna library incorporating a cationic functionality." Biochemistry (2003) vol. 42, Issue 29, pp. 8842-8851.

Wallace et al., "In vitro selection and characterization of streptomycin-binding RNAs: Recognition discrimination between antibiotics." RNA (1998); 4(I): 112-123.

Wang et al., "RNA molecules that specifically and stoichiometrically bind aminoglycoside anitibiotics with high affinities." Biochemistry (1996) vol. 35, Issue 38, pp. 12338-12346.

Wang et al., "Recent patents on the identification and clinical application of microRNAs and target genes." Recent Pat DNA Gene Seq (2007). 1: 116-124.

Wang et al., "MicroRNA-based therapeutics for cancer." BioDrugs (2009). 23:15-23.

Weigand et al., "Screening for engineered neomycin riboswitches that control translation initiation." RNA (2008); 14: 89-97.

Wieland et al., "Artificial ribozyme switches containing natural riboswitch aptamer domains." Angew Chern Int Ed Eng (2009). 148: 2715-2718.

Wilson et al., "Functional requirements for specific ligand recognition by a biotin-binding RNA pseudoknot." Biochemistry (1998); 37: 14410-14419.

Xia et al., "Multiple shRNAs expressed by an inducible pol II promoter can knock down the expression of multiple target genes." Biotechniques (2006); 41: 64-68.

Yang et al., "DNA ligands that bind tightly and selectively to cellobiose." PNAS (1998); 95(10): 5462-5467.

Yeom et al., "Characterization of DGCR8/Pasha, the essential cofactor for Drosha in primary miRNA processing." Nucleic Acids Res. 2006; 34(16):4622-4629. Epub Sep. 8, 2006.

Zeng et al., "Sequence requirements for micro RNA processing and function in human cells." RNA (2003); 9: 112-123.

Zeng et al., "Efficient processing of primary microRNA hairpins by Drosha requires flanking nonstructured RNA sequences." J Biol Chern (2005); 280: 27595-27603.

Zeng et al., "Both natural and designed micro RNAs can inhibit the expression of cognate mRNAs when expressed in human cells." Mol Cell (2002); 9: 1327-1333.

* cited by examiner

SEQUENCE LISTING

```
<160> NUMBER OF SEQ ID NOS: 34

<210> SEQ ID NO 1
<211> LENGTH: 22
<212> TYPE: RNA
<213> ORGANISM: Artificial Sequence
<220> FEATURE:
<223> OTHER INFORMATION: GFP Sequence

<400> SEQUENCE: 1
uaguuguacu ccagcuugug cc                                              22

<210> SEQ ID NO 2
<211> LENGTH: 7
<212> TYPE: DNA
<213> ORGANISM: Artificial Sequence
<220> FEATURE:
<223> OTHER INFORMATION: Primer

<400> SEQUENCE: 2 cgccacc                                                                7

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gttcctgtag acggctctc                                                  19

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
aatacctagg ctgatcagcg ggttt                                           25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
aatacctagg agggcaaac aacag                                            25

<210> SEQ ID NO 6
<211> LENGTH: 27
<212> TYPE: DNA
<213> ORGANISM: Artificial Sequence
```

```
<220> FEATURE:
<223> OTHER INFORMATION: Primer

<400> SEQUENCE: 6
aatacctagg aaaggacagt gggagtg                                    27

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ggttgaaccg tctaacaaca g                                          21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
atgtcatcaa gagttgcatc ag                                         22

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gaaggtgaag gtcggagtc                                             19

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gaagatggtg atgggatttc                                            20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aagaagacta tgggctggga                                            20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cgatggtgta gtcctcgttg                                            20
```

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
accttgctcc tgccgagaaa gtat                                          24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
atgtttcgct tggtggtcga atgg                                          24

<210> SEQ ID NO 15
<211> LENGTH: 22
<212> TYPE: DNA
<213> ORGANISM: Artificial Sequence
<220> FEATURE:
<223> OTHER INFORMATION: GFP Sequence

<400> SEQUENCE: 15
ggcacaagct ggagtacaac ta                                            22

<210> SEQ ID NO 16
<211> LENGTH: 22
<212> TYPE: DNA
<213> ORGANISM: Artificial Sequence
<220> FEATURE:
<223> OTHER INFORMATION: GFP Sequence

<400> SEQUENCE: 16
tccaggagcg caccatcttc tt                                            22

<210> SEQ ID NO 17
<211> LENGTH: 22
<212> TYPE: DNA
<213> ORGANISM: Artificial Sequence
<220> FEATURE:
<223> OTHER INFORMATION: GFP Sequence

<400> SEQUENCE: 17
atggaaatca gtgaagataa aa                                            22

<210> SEQ ID NO 18
<211> LENGTH: 116
<212> TYPE: DNA
<213> ORGANISM: Artificial Sequence
<220> FEATURE:
<223> OTHER INFORMATION: miRNA

<400> SEQUENCE: 18
tctagagttt gacagtgagc gagcacaagc tggagtacaa ctatagtgaa gccacagatg   60
tatagttgta ctccagcttg tgcctgccta ctgcctcgga ctgaattcat agggcc      116

<210> SEQ ID NO 19
<211> LENGTH: 114
<212> TYPE: DNA
<213> ORGANISM: Artificial Sequence
```

```
<220> FEATURE:
<223> OTHER INFORMATION: miRNA

<400> SEQUENCE: 19
tctagaacgg gaagtaatta cagtgagcga gcacaagctg gagtacaact atagtgaagc    60
cacagatgta tagttgtact ccagcttgtg cctgcctact gccacatagg gccc          114

<210> SEQ ID NO 20
<211> LENGTH: 107
<212> TYPE: DNA
<213> ORGANISM: Artificial Sequence
<220> FEATURE:
<223> OTHER INFORMATION: miRNA

<400> SEQUENCE: 20
tctagaacgg gaaacacagt gagcgagcac aagctggagt acaactatag tgaagccaca    60
gatgtatagt tgtactccag cttgtgcctg cctactgcct cgggccc                   107

<210> SEQ ID NO 21
<211> LENGTH: 105
<212> TYPE: DNA
<213> ORGANISM: Artificial Sequence
<220> FEATURE:
<223> OTHER INFORMATION: miRNA

<400> SEQUENCE: 21
tctagaacgg gaaacacagt gagcgagcac aagctggagt acaactatag tgaagccaca    60
gatgtatagt tgtactccag cttgtgcctg cctactgccg ggccc                     105

<210> SEQ ID NO 22
<211> LENGTH: 102
<212> TYPE: DNA
<213> ORGANISM: Artificial Sequence
<220> FEATURE:
<223> OTHER INFORMATION: miRNA

<400> SEQUENCE: 22
tctagaacgg gaaacacagt gagcgagcac aagctggagt acaactatag tgaagccaca    60
gatgtatagt tgtactccag cttgtgcctg cctactgggg cc                        102

<210> SEQ ID NO 23
<211> LENGTH: 120
<212> TYPE: DNA
<213> ORGANISM: Artificial Sequence
<220> FEATURE:
<223> OTHER INFORMATION: miRNA

<400> SEQUENCE: 23
tctagaacgg gtcctgatac cagcgtgagc gagcacaagc tggagtacaa ctatagtgaa    60
gccacagatg tatagttgta ctccagcttg tgcccgccta cgcccttggc agcagggccc    120

<210> SEQ ID NO 24
<211> LENGTH: 120
<212> TYPE: DNA
<213> ORGANISM: Artificial Sequence
<220> FEATURE:
<223> OTHER INFORMATION: miRNA

<400> SEQUENCE: 24
tctagaacgg gtcctgatac cagcgtgagc gagcacaagc tatcaacatg aggtagtgaa    60
gccacagatg tacctcatgt tgatagcttg tgcccgccta cgcccttggc agcagggccc    120
```

```
<210> SEQ ID NO 25
<211> LENGTH: 120
<212> TYPE: DNA
<213> ORGANISM: Artificial Sequence
<220> FEATURE:
<223> OTHER INFORMATION: miRNA

<400> SEQUENCE: 25
tctagaacgg gtcctgatac cagcgtgagc gccaagaaga tggtgcgctc ctggagtgaa      60
gccacagatg tccaggagcg caccatcttc ttgtcgccta cgcccttggc agcagggccc     120

<210> SEQ ID NO 26
<211> LENGTH: 242
<212> TYPE: DNA
<213> ORGANISM: Artificial Sequence
<220> FEATURE:
<223> OTHER INFORMATION: miRNA

<400> SEQUENCE: 26
tctagacgcc agaatgatac cagcgtgagc gagcacaagc tggagtacaa ctatagtgaa      60
gccacagatg tatagttgta ctccagcttg tgcccgccta cgcccttggc agcattctgg     120
cgcctagaac gggtcctgat accagcgtga gcgagcacaa gctggagtac aactatagtg     180
aagccacaga tgtatagttg tactccagct tgtgcccgcc tacgcccttg gcagcagggc     240
cc                                                                    242

<210> SEQ ID NO 27
<211> LENGTH: 259
<212> TYPE: DNA
<213> ORGANISM: Artificial Sequence
<220> FEATURE:
<223> OTHER INFORMATION: miRNA

<400> SEQUENCE: 27
tctagaacgg gtcctgatac cagcgtgagc gagcacaagc tggagtacaa ctatagtgaa      60
gccacagatg tatagttgta ctccagcttg tgcccgccta cgcccttggc agcagggccc     120
gtttaaaccc gctgatcagc ctagaacggg tcctgatacc agcgtgagcg agcacaagct     180
ggagtacaac tatagtgaag ccacagatgt atagttgtac tccagcttgt gcccgcctac     240
gcccttggca gcagggccc                                                 259

<210> SEQ ID NO 28
<211> LENGTH: 296
<212> TYPE: DNA
<213> ORGANISM: Artificial Sequence
<220> FEATURE:
<223> OTHER INFORMATION: miRNA

<400> SEQUENCE: 28
tctagaacgg gtccgtgtat tacctgagcg agcacaagct ggagtacaac tatagtgaag      60
ccacagatgt atagttgtac tccagcttgt gcccgcctag tcgacgggc ccgtttaaac      120 ccgctgatca gcctcgactg tgccttctag ttgccagcca tctgttgttt gcccctccta     180
gaacgggtcc tgataccagc gtgagcgagc acaagctgga gtacaactat agtgaagcca     240
cagatgtata gttgtactcc agcttgtgcc cgcctacgcc cttggcagca gggccc         296

<210> SEQ ID NO 29
<211> LENGTH: 350
<212> TYPE: DNA
<213> ORGANISM: Artificial Sequence
```

```
<220> FEATURE:
<223> OTHER INFORMATION: miRNA

<400> SEQUENCE: 29
tctagaacgg gtccgaggtc gacgtgagcg agcacaagct ggagtacaac tatagtgaag      60
ccacagatgt atagttgtac tccagcttgt gcccgcctac gtgtattacc cagggcccgt    120
ttaaacccgc tgatcagcct cgactgtgcc ttctagttgc cagccatctg ttgtttgccc    180
ctcccccgtg ccttccttga ccctggaagg tgccactccc actgtccttt cctagaacgg    240
gtcctgatac cagcgtgagc gagcacaagc tggagtacaa ctatagtgaa gccacagatg    300
tatagttgta ctccagcttg tgcccgccta cgcccttggc agcagggccc                350

<210> SEQ ID NO 30
<211> LENGTH: 134
<212> TYPE: DNA
<213> ORGANISM: Artificial Sequence
<220> FEATURE:
<223> OTHER INFORMATION: miRNA

<400> SEQUENCE: 30
tctagaacgg gtcctaaaac ataccgtgag cgagcacaag ctggagtaca actatagtga     60
agccacagat gtatagttgt actccagctt gtgcctgcct acggagaggt gaagaatacg    120
accacctagg gccc                                                      134

<210> SEQ ID NO 31
<211> LENGTH: 112
<212> TYPE: DNA
<213> ORGANISM: Artificial Sequence
<220> FEATURE:
<223> OTHER INFORMATION: miRNA

<400> SEQUENCE: 31
tctagaacgg gtccgtgtat tacctgagcg agcacaagct ggagtacaac tatagtgaag     60
ccacagatgt atagttgtac tccagcttgt gcccgcctag gtcgacgggc cc            112

<210> SEQ ID NO 32
<211> LENGTH: 118
<212> TYPE: DNA
<213> ORGANISM: Artificial Sequence
<220> FEATURE:
<223> OTHER INFORMATION: miRNA

<400> SEQUENCE: 32
tctagaacgg gtccgaggtc gacgtgagcg agcacaagct ggagtacaac tatagtgaag     60
ccacagatgt atagttgtac tccagcttgt gcccgcctac gtgtattacc cagggccc     118

<210> SEQ ID NO 33
<211> LENGTH: 117
<212> TYPE: DNA
<213> ORGANISM: Artificial Sequence
<220> FEATURE:
<223> OTHER INFORMATION: miRNA

<400> SEQUENCE: 33
tctagagttt gacagtgagc gctggaaatc agtgaagata aaatagtgaa gccacagatg     60
tattttatct tcactgattt ccattgccta ctgcctcgga ctgaattcat agggccc      117

<210> SEQ ID NO 34
<211> LENGTH: 120
<212> TYPE: DNA
```

```
<213> ORGANISM: Artificial Sequence
<220> FEATURE:
<223> OTHER INFORMATION: miRNA

<400> SEQUENCE: 34
tctagaacgg gtcctgatac cagcgtgagc gctggaaatc agtgaagata aaatagtgaa      60
gccacagatg tattttatct tcactgattt ccatcgccta cgcccttggc agcagggccc    120
```

INTEGRATED—LIGAND-RESPONSIVE MICRORNAS

CROSS-REFERENCE TO RELATED APPLICATIONS

This application claims priority from U.S. Provisional No. 61/166,203, filed Apr. 2, 2009, the contents of which application is incorporated herein by reference in its entirety.

STATEMENT REGARDING FEDERALLY SPONSORED R&D

The U.S. Government has certain rights in this invention pursuant to Grant No. W81XWH-06-1-0250 awarded by ARO.

REFERENCE TO SEQUENCE LISTING, TABLE, OR COMPUTER PROGRAM LISTING

The present application is being filed along with a Sequence Listing in electronic format. The Sequence Listing is provided as a file entitled 2010-04-01_SEQ_LIST_CALTE-061A.txt, created Apr. 1, 2010, which is 8192 bytes in size. The information in the electronic format of the Sequence Listing is incorporated herein by reference in its entirety.

BACKGROUND OF THE INVENTION

1. Field of the Invention

The invention relates to the field of regulation of microRNA activity and expression.

2. Description of the Related Art

MicroRNAs are small RNAs that mediate gene silencing in metazoans and can regulate diverse cellular processes.

MicroRNAs (miRNAs) comprise a conserved class of small noncoding RNAs that direct targeted gene silencing through the RNA interference (RNAi) pathway in humans and other eukaryotes. Most miRNAs are encoded within long transcripts transcribed from Pol II promoters (Cai et al., 2004; Lee et al., 2002). The primary (pri-)miRNA is initially processed to an ~65 nucleotide (nt) precursor (pre-)miRNA by the Microprocessor (Gregory et al., 2004; Han et al., 2004; Lee et al., 2003) composed of the cleaving enzyme Drosha and the RNA binding protein DGCR8. Following pri-miRNA cleavage and export from the nucleus, the pre-miRNA is processed by Dicer to a 22-25 nt miRNA duplex. One of the duplex strands termed the mature miRNA is incorporated into the RNA-induced silencing complex (RISC), which subsequently cleaves or translationally represses the target transcript depending on the degree of complementarity between the guide sequence of the miRNA and the target. miRNA-mediated gene regulation has been implicated in diverse biological processes ranging from development to angiogenesis and may be involved in the regulation of a majority of the human genome (Friedman et al., 2009).

Recently, researchers have designed synthetic RNA-based regulatory systems that integrate sensing and gene-regulatory functions, where the former are encoded in RNA aptamer sequences that recognize small molecule ligands (Suess and Weigand, 2008). Such integrated ligand-responsive RNA-based control systems offer several advantages over more traditional protein-based regulatory systems in avoiding potential immunogenicity of heterologous protein components and providing a more tunable, compact control system. In addition, as aptamers can be selected against a wide range of biomolecules (Osborne and Ellington, 1997), such integrated RNA systems provide platforms for gene expression control in response to potentially any molecular input.

Recently, integrated RNA-based control systems that mediate gene silencing through the RNAi pathway in response to small molecule ligands have been demonstrated (An et al., 2006; Beisel et al., 2008; Tuleuova et al., 2008). These systems were built from gene regulatory functions encoded by intermediate substrates in the processing pathway, small hairpin RNAs (shRNAs). Both designs linked small molecule RNA aptamers to the loop region of shRNA elements to modulate the extent of Dicer processing and subsequent gene silencing through ligand binding events based on known structural requirements for efficient Dicer processing (An et al., 2006; Beisel et al., 2008). However, the adopted mode of ligand control inherently reduced silencing (Beisel et al., 2008) and ligand regulation through Dicer processing restricts molecular sensing to cytoplasmic ligands. In addition, the expression architecture of shRNAs requires additional promoter-shRNA constructs to expand the number of ligand-responsive shRNAs, which represents a challenge for therapeutic applications. Finally, sequence restrictions and in vivo toxicity of shRNAs (Boudreau et al., 2009; Grimm et al., 2006; McBride et al., 2008) establish significant hurdles toward broader implementation of shRNA-based control systems. Other researchers have used artificial miRNAs rather than shRNAs (Bauer et al., 2009; Boudreau et al., 2009; McBride et al., 2008).

Engineered genetic systems that display ligand control of miRNA-mediated gene silencing will provide a powerful and versatile means to control transgene and endogenous gene expression.

SUMMARY OF THE INVENTION

In some embodiments, a system comprising a nucleic acid comprising: a miRNA nucleic acid domain, wherein the miRNA nucleic acid domain has a basal segment region, and a RNA sensor domain configured to bind to a ligand, wherein the RNA sensor domain is in the basal segment region, is provided. In some embodiments, binding of the ligand to the sensor domain modulates processing of the miRNA nucleic acid domain by an RNA binding protein or RNA processing enzyme.

In some embodiments, the miRNA nucleic acid domain can have a portion that is complementary to a target RNA transcript.

In some embodiments, the nucleic acid comprises more than one RNA sensor domain, and wherein the sensor domains bind to the ligand.

In some embodiments, the nucleic acid further comprises a second miRNA nucleic acid domain and a second RNA sensor domain, configured to bind to a ligand. In such embodiments, the RNA sensor domain is located within the basal segment region of the second miRNA nucleic acid domain.

In some embodiments, the nucleic acid has more than one RNA sensor domain, and at least one sensor domain binds to the ligand, and further comprising at least one additional ligand, wherein at least one sensor domain binds to the additional ligand.

In some embodiments, binding of the ligand to the sensor domain inhibits processing by the RNA processing enzyme or RNA binding protein, and in some embodiments, binding of the ligand to the sensor domain enhances processing by the RNA processing enzyme or RNA binding protein.

In some embodiments, the RNA processing enzyme or RNA binding protein is Drosha or DGCR8.

In some embodiments, the ligand is endogenous to a cell. In some embodiments, the ligand is exogenous to a cell. In some embodiments, the ligand is cell permeable. In some embodiments, the ligand is selected from the group consisting of polypeptides, peptides, nucleic acids, carbohydrates, fatty acids, lipids, non-peptide hormones, and metabolic precursors or products thereof. In some embodiments, the ligand has a molecular weight less than about 2.5 kDa, less than about 1 kDa, or less than about 0.5 kDa.

In some embodiments, the ligand is theophylline, tetracycline, phenobarbital, tamoxifen, folinic acid, vitamin B12, biotin, Rev, Tat, dopamine, p50, p65, B-catenin, SAM, SAH, TPP, vitamin B1, adenine, or guanosine.

In some embodiments, the miRNA down regulates expression of a target RNA. In other embodiments, the miRNA activates expression of a target RNA.

In some embodiments, a cell comprising one or more nucleic acids comprising: a miRNA nucleic acid domain, wherein the miRNA nucleic acid domain has a basal segment region, and a RNA sensor domain configured to bind to a ligand, wherein the RNA sensor domain is in the basal segment region, is provided. In some embodiments, binding of the ligand to the sensor domain modulates processing of the miRNA nucleic acid domain by an RNA binding protein or RNA processing enzyme.

In some embodiments, the cell is a prokaryotic cell or a eukaryotic cell. In some embodiments, the cell is a mammalian cell. In some embodiments, the cell is a plant cell. In some embodiments, a method of affecting processing of an miRNA nucleic acid is provided. In such embodiments, the method comprises: providing to the cell, a nucleic acid system comprising: a miRNA nucleic acid domain, wherein at least one guide sequence region of the miRNA nucleic acid domain is complementary a target RNA transcript; and a RNA sensor domain that can bind to a ligand, wherein binding of the ligand to the sensor domain modulates processing of the miRNA nucleic acid domain by an RNA processing enzyme or RNA binding protein. In some embodiments, the method includes contacting the cell with the ligand.

DETAILED DESCRIPTION

Figure 1:
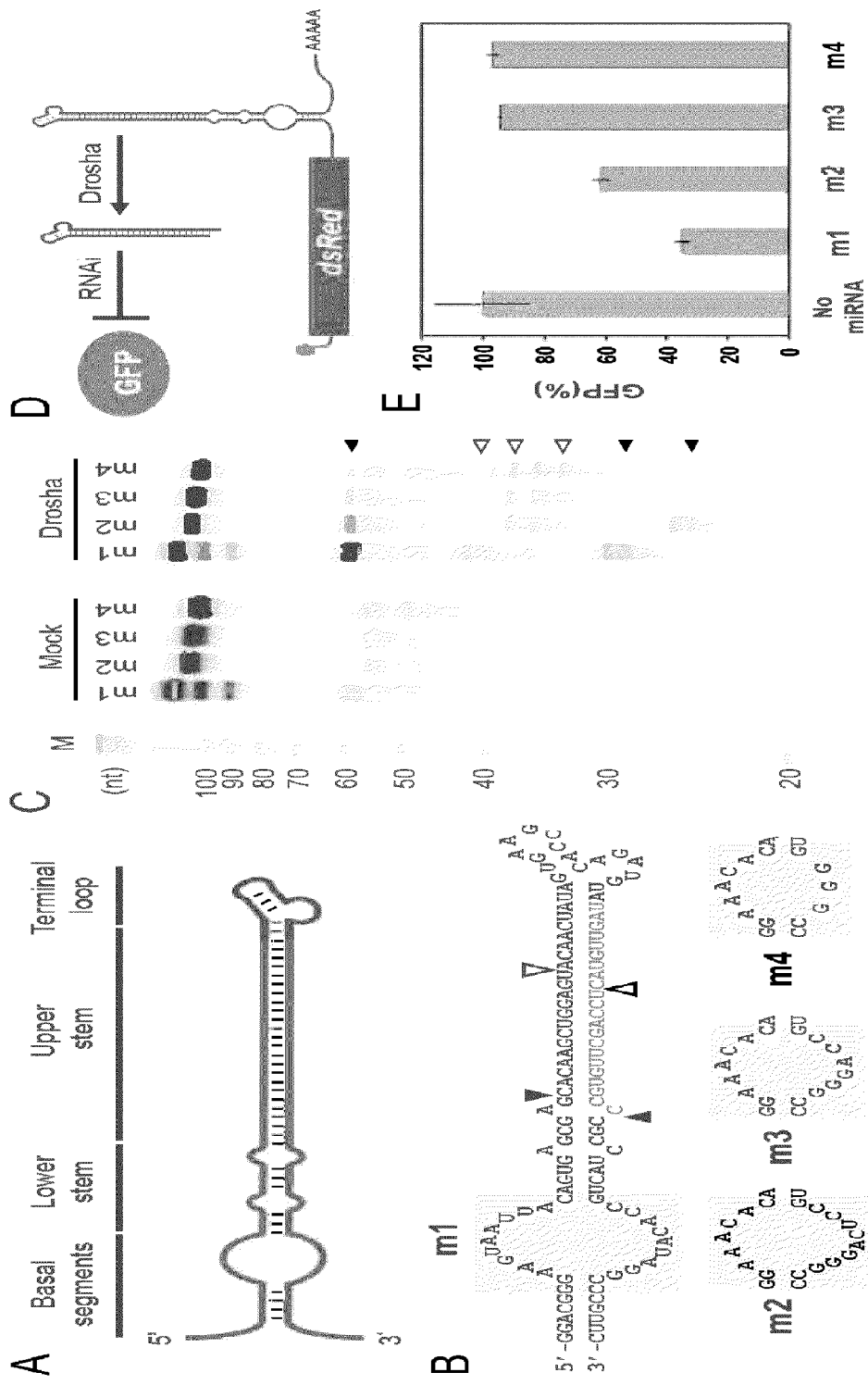
FIG. 1 illustrates that the extent of structure in the basal segments dictates miRNA processing and target gene silencing. (A) General domains of a pri-miRNA. (B) Sequence and secondary structure of minimal pri-miRNAs with different bulge sizes in the basal segments. Mature miRNA sequence targeting GFP is shaded (SEQ ID NO. 1: 5'-UAGUU-GUACUCCAGCUUGUGCC-3'). The bulge sequences are marketed by boxes, m1, m2, m3, and m4. Black and white arrows indicate the putative cleavage sites for productive and abortive processing, respectively, based on data from the cleavage assay. (C) PAGE analysis of the minimal pri-miRNAs subjected to the Drosha cleavage assay. Black and white arrows mark the presumed productive and abortive cleavage products as indicated in B. (D) Schematic of the miRNA regulatory system in the cell culture assay. GFP-targeting miRNAs were placed within the 3' UTR of the transcript encoding DsRed-Express. 293-GFP cells transiently transfected with each construct was subjected to flow cytometry analysis. (E) Relative GFP levels obtained from the cell culture assay for constructs harboring miRNAs with varying bulge sizes. Error bars represent the standard deviation of two independent transfections.

In some embodiments, miRNAs with a sensor domain within the basal segment region are provided. The sensor domain can be an aptamer that can bind a ligand. Ligand binding to the aptamer sequence can modulate processing of the miRNA by RNA processing enzymes. When the miRNA has a guide sequence that is complementary to a target RNA sequence, the ligand can modulate expression of the target RNA sequence. The ligands can be endogenous or exogenous. In some embodiments, ligand binding to the sensor domain disrupts processing of the miRNA by an RNA processing enzyme or RNA binding protein, for example, Microprocessor. Inhibition of such processing results in a failure to process the miRNA to give a mature miRNA. In such an embodiment, the ligand binding will generally up regulate the target RNA sequence.

DEFINITIONS

As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a stem may comprise more than one bulge. In certain embodiments, one or both strands of the stem contain a bulge.

"Complementary" refers to a nucleotide or nucleotide sequence that hybridizes to a given nucleotide or nucleotide sequence. For instance, for DNA, the nucleotide A is complementary to T, and vice versa, and the nucleotide C is complementary to G, and vice versa. For instance, in RNA, the nucleotide A is complementary to the nucleotide U, and vice versa, and the nucleotide C is complementary to the nucleotide G, and vice versa. Complementary nucleotides include those that undergo Watson and Crick base pairing and those that base pair in alternative modes. For instance, as used herein for RNA, the nucleotide G is complementary to the nucleotide U and vice versa, and the nucleotide A is complementary to the nucleotide G and vice versa. Therefore, in an RNA molecule, the complementary base pairs are A and U, G and C, G and U, and A and G. Other combinations, e.g., A and C, A and A, G and G, or C and U, are considered to be non-complementary base pairs.

Due to the binding energy differences between different base pairs, the "quality of complementarity" also varies, and may be explored to fine tune the free energy differences between different conformations of the subject regulated polynucleotides. For example, the G-C base pair exhibits the highest binding affinity, and thus is said to have a higher quality of binding than that of an A-T or A-U pair, or a G-U pair, etc. Depending on specific needs, a Watson-Crick base pair may be replace by another (stronger or weaker) Watson-Crick base pair, or a wobble base pair to alter the quality of complementarity of any region in the subject regulated nucleic acid.

"Component" is a part of a system that encodes a distinct activity or function.

"Do/does not bind" as used herein to describe aptamer-ligand binding, does not mean that there is absolutely no binding at all. Compared to an aptamer that does bind the ligand (a "binding aptamer"), the KApt (association constant for binding between ligand and aptamer) for the aptamer that "does not bind" the ligand is at least about 10-fold, 100-fold, 1000-fold or more larger than that of the binding aptamer, and thus its binding affinity for the ligand is at least about 10-fold, 100-fold, 1000-fold or more weaker than that of the binding aptamer.

"DGCR8" refers to DiGeorge syndrome critical region gene 8 (Accession # AAF2263). DGCR8—called Pasha in *C. elegans* and *D. melangaster*—is a cofactor in miRNA processing by Drosha and has been implicated in miRNA binding (Yeom et al., Nucleic Acids Res. 2006; 34(16):4622-9. Epub 2006 Sep. 8).

"Dicer" refers to the cytoplasmic RNase-III like enzyme responsible for the double-stranded cleavage of pre-miRNAs (Accession # NP 803187) (Bernstein et al., Nature. 2001 Jan. 18; 409(6818):295-6). Cleaved miRNAs are then loaded into RNA-induced silencing complex.

"Drosha" refers to the nuclear RNase-III enzyme in the Microprocessor complex responsible for double-stranded cleavage of pri-miRNAs (Accession # NP_037367) (Lee et al., Nature. 2003 Sep. 25; 425(6956):415-9). Drosha homologues are found in many different organisms, including humans, mice, *C. elegans*, and *D. melangaster*.

"Guide sequence" as used herein, means a sequence within an miRNA that is complementary to a target RNA transcript. In some embodiments, the guide sequence is between about 19 and 27 nucleotides, and more preferably from 22 to about 25 nucleotides, and can be incorporated in the RNA-induced silencing complex to cleave or repress the target RNA transcript.

"Loop" refers to a sequence of nucleotides that is not paired with another strand. In certain embodiments, a loop is between 1 to 20 nucleotides long, 2-10 nucleotides long, or 3-8 nucleotides long.

"Microprocessor" is a molecular complex comprising DGCR8 and Drosha.

"miRNA" refers to an RNA polynucleotide that has regulatory activity within a cell, or can have regulatory activity in a cell after processing. The miRNA can be encoded in DNA, and transcribed as a long transcript, for example from a Pol II promoter (Cai et al., 2004; Lee et al., 2002). The primary (pri-)miRNA is initially processed to an approximately 65 nucleotide (nt) precursor (pre-)miRNA by the Microprocessor (Gregory et al., 2004; Han et al., 2004; Lee et al., 2003) composed of the cleaving enzyme Drosha and the RNA binding protein DGCR8. Following pri-miRNA cleavage and export from the nucleus, the pre-miRNA is processed by Dicer to a 22-25 nt miRNA duplex. One of the duplex strands termed the mature miRNA is incorporated into the RNA-induced silencing complex (RISC), which subsequently cleaves or translationally represses the target transcript depending on the degree of complementarity between the guide sequence of the miRNA and the target. miRNA-mediated gene regulation has been implicated in diverse biological processes ranging from development to angiogenesis and may be involved in the regulation of a majority of the human genome (Friedman et al., 2009). In other embodiments, the miRNA can be an RNA polynucleotide that is either chemically or enzymatically synthesized, for example, by template directed transcription. Such an miRNA can be introduced to a cell using any techniques known to one of skill in the art, including, for example, the use of liposomes or nanoparticles. In particular, techniques developed for the delivery of siRNA molecules can be used for the delivery of miRNAs.

"Modular" refers to a property of a system composed of modules that indicates whether the modules can by interchanged as parts without changing the interface between modules or the modules themselves.

"Module" refers to a self-contained system component that has a well defined interface with other system components.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N-6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

"Nucleic acid," "nucleic acid sequence," "nucleic acid molecule," and "polynucleotide" refer to a DNA sequence or analog thereof, or an RNA sequence or analog thereof, or combinations thereof, including chimeric molecules. Nucleic acids are formed from nucleotides, including, but not limited to, the nucleotides listed above. A polynucleotide may include analogs of DNA or RNA having modifications to either the bases or the backbone. For example, polynucleotides, as used herein, includes the use of peptide nucleic acids (PNA), phosphorothioates, phosphoramides, phosphorodithioates, O-methylphosphoroamidites, and any other modifications to the backbone.

"pre-miRNA" means an miRNA that can serve as a substrate for Dicer.

"pri-miRNA" means an miRNA that can serve as a substrate for the Microprocessor or Drosha.

"Polynucleotide" has the meaning set forth above.

"RNA-induced silencing complex" or "RISC" refers to a protein complex involved in RNA interference (Sontheimer, Nat Rev Mol Cell Biol. 2005 February; 6(2):127-38). RISC carries out targeted gene silencing in many different organisms using the mature miRNA as a template to recognize complementary RNA sequences. In humans, RISC is often composed of various proteins, including Argonaute2 (Accession # NP_036286) (Hammond et al., Science. 2001 Aug. 10; 293(5532):1146-50).

A "stem" is a double-stranded nucleic acid motif formed by inter- or intra-molecular base pairing, which may or may not include mismatched base pairs or "bulges." In certain embodiments, a stem comprises 2 to about 40, or 2 to about 20 complementary base pairs. In certain embodiments, a stem comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 complementary base pairs.

In certain embodiments, at least 30% of the nucleotides in a stem are part of a complementary base pair. The remaining base pairs may be mismatched, non-complementary base pairs, or may be part of a bulge. In certain embodiments, at least 40%, 50%, 60%, 70%, 80%, 90%, 95%, 99%, or 100% of the nucleotides in the stem are part of a complementary base pair.

"Sensor domain" refers to a nucleic acid sequence or polynucleotide that comprises a ligand-binding function. In certain embodiments, the sensor domain comprises an RNA aptamer sequence.

Other terms used herein and in the claims adopt their plain meanings as would have been understood by one of skill in the relevant art, that are not inconsistent with the usages in the instant specification.

Nucleic Acid Systems

In some embodiment, the invention provides nucleic acid systems. In such embodiments, a nucleic acid is a polynucleotide that comprises at least two regions: an miRNA nucleic acid domain and an RNA sensor domain. Such nucleic acids may comprise DNA or RNA, analogs there of, or a combination of the foregoing. The nucleic acids may also be single-stranded or double-stranded. The single-stranded polynucleotide may comprise one or more double-stranded regions (or stems) due to intramolecular interaction (e.g., RNA secondary structure). If one or more phosophodiester linkage between the nucleotides are broken, the folded polynucleotide may in fact be double-stranded while maintaining substantially the same secondary structure. In some embodiments, the nucleic acid system is substantially an miRNA nucleic acid domain. In some embodiments, the nucleic acid system also may comprise additional components such as promoters, reporter genes, marker sequences, and other sequences known to one of skill in the art.

miRNA Nucleic Acid Domains miRNA nucleic acid domains are generally stem-loop structures including one or more bulge regions. In some embodiments, the miRNA nucleic acid domain is about 40 to about 200 nucleotides in length. In some embodiments, the miRNA nucleic acid domain is a stem loop structure having about 40 to about 100 nucleotides in length. As used herein, the miRNA nucleic acid domain includes both the pri-miRNA and pre-miRNA nucleotide sequences before cleavage by Drosha, or by Dicer respectively. An miRNA nucleic acid domain can serve as a substrate for Drosha or Dicer.

In some embodiments, the miRNA has a guide sequence region that, after cleavage by Dicer, can form a double stranded RNA that can act through the RNA interference pathway, through interaction with RISC, to modulate the activity of a target RNA transcript. In some embodiments, the guide sequence is from about 22 to about 25 nucleotides in length. In some embodiments, the guide sequence is substantially complementary to a target RNA sequence, having a sequence complementarity of at least about 50%, 60%, 70%, 80%, 90% or 95% to the target RNA transcript.

Basal Segment Regions

In some embodiments, an miRNA suitable for use with the invention will have a basal segment region. miRNAs can be partitioned into four domains (FIG. 1A) that exhibit unique structural requirements for efficient Drosha processing and RISC activation (Han et al., 2006; Zeng and Cullen, 2003, 2005; Zeng et al., 2005). The miRNA with a basal segment region can be a substrate for the RNA processing enzyme Drosha. Drosha cleaves double stranded RNA strands in the stem of the pri-miRNA stem loop structure, making a double stranded cut. The basal segment region is distal from the terminal loop of the miRNA and the guide sequence (if any) in the miRNA. If such an miRNA were cleaved by Drosha, cleavage separates the basal segments from the pri-miRNA, leave a pre-miRNA that can be processed by Dicer or similar enzyme. In some embodiments, the basal segment region is: a) that region of the miRNA that extends to the 5' (up to and including the 5' end of the miRNA) of: i) a 5' Drosha cleavage site or ii) the 3' or 5' end of a guide sequence region; and b) that region of the miRNA that extends to the 3' (up to and including the 3' end of the miRNA) of: i) a 3' Drosha cleavage site or ii) the 3' or 5' end of a guide sequence region. In some embodiments, the basal segment region extends to about 500, 400, 300, 200, 100 or 50 nucleotides to the 5' of a 5' Drosha cleavage site or the 3' or 5' end of a guide sequence region and to about 500, 400, 300, 200, 100 or 50 nucleotides to the 3' of a 3' Drosha cleavage site. Referring to FIG. 1A, a basal segment region can encompass both the "lower stem" and "basal segments". In some embodiments, the basal segment region forms a bulge of between about 3 to about 20 nucleotides. In some other embodiments, the basal segment region is a single stranded region.

Sensor Domains

A sensor domain binds to a ligand. The sensor domain modulates the activity of Drosha processing of the miRNA nucleic acid. Sensor domains are integrated into the basal segment region of the miRNA, forming all or a portion of a basal segment region.

In some embodiments, the sensor domain has less than about a 100-fold, less than about 10-fold, or less than about 5-fold effect on the Drosha processing of the pri-miRNA in the absence of the ligand, or when the ligand is not bound, relative to a basal segment region that is not a sensor domain, for example, a naturally occurring basal segment region. Binding of the ligand to the sensor domain will modulate activity of Microprocessor processing of the miRNA. Such modulation can occur, for example, through interaction of a ligand bound sensor domain with DGCR8 or Drosha. The binding of a ligand to a sensor domain, in some embodiments, an aptamer, alters the ability of the miRNA to interact with the miRNA processing machinery. Therefore, ligand binding affects the ability of the miRNA to mediate gene inactivation, transcription, translation, or otherwise interfere with the normal activity of the target gene or mRNA, for example.

Sensor domains, for example, aptamers, can be selected to work in a basal segment domain based on certain design criteria, and by confirmation of activity in a miRNA system. As described herein, we have designed ligand-responsive miRNAs and demonstrated that the bulge size in the miRNA basal segments dictates the extent of Drosha processing and in vivo silencing. By integrating an aptamer into the miRNA basal segments, we demonstrated that aptamer-ligand binding interactions can be used to sufficiently increase the local structure in the miRNA basal segment region, such that Drosha processing and subsequent gene silencing were inhibited with increasing ligand concentration. The sequence flexibility of the basal segments allows for the introduction of different aptamer sequences in this region, resulting in a modular design framework that allows modification of the detected ligand or target gene.

An "aptamer" may be a nucleic acid molecule, such as RNA or DNA that is capable of binding to a specific molecule with high affinity and specificity (Ellington et al., Nature 346, 818-22 (1990); and Tuerk et al., Science 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. In some embodiments, aptamers that are suitable for use with the miRNA framework have a bulge-loop structure that can be integrated in the basal segment region without significant reengineering of the miRNA. In some embodiments, aptamers can be selected using procedures that preferentially select bulge-loop structures. In some embodiments, aptamers are screened using in vivo screening strategies for RNA-based regulatory systems that identify sequences that function as integrated sensing components (see, for example, Weigand et al., 2008). In some embodiments, one or more loop regions from an aptamer are integrated into, or in place of, basal segment regions of miRNA. The aptamer can be entirely contiguous, or can be formed from sequences separated by one or more nucleotides. For example, an aptamer can be a single loop on one side of the miRNA structure. In one embodiment, the aptamer is formed by two or more sequences that are separated by the guide sequence and the loop of the miRNA.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_D$) of the aptamer for its ligand as compared to the dissociation constant of the aptamer for other materials in the environment or unrelated molecules in general. A ligand is one which binds to the aptamer with greater affinity than to unrelated material. Typically, the $K_D$ for the aptamer with respect to its ligand will be at least about 10-fold less than the $K_D$ for the aptamer with unrelated material or accompanying material in the environment. Even more preferably, the $K_D$ will be at least about 50-fold less, more preferably at least about 100-fold less, and most preferably at least about 200-fold less. An aptamer will typically be between about 3 and about 300 nucleotides in length. In some embodiments, an aptamer will be between about 5 to 100 nucleotides in length. In some embodiments, the aptamer is between about 5 and about 25 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

Aptamers are readily made that bind to a wide variety of molecules. Each of these molecules can be used as a modulator of gene expression using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green, Science 282:296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, Science 9:324-9 (1999).

Beyond in vitro selected aptamers, aptamers present in natural riboswitches have also been rationally integrated into RNA-based ligand control systems (Wieland et al., 2009). While most aptamers conform to a standard bulge-loop structure, many adopt alternative structures, such as pseudoknots (Tuerk et al., 1992; Wilson et al., 1998) or dangling ends (Koizumi and Breaker, 2000), that may be incompatible with the ligand-responsive miRNA framework. Such aptamers can be tested for their ability to introduce ligand regulation of gene expression, and can be modified according to the principles herein to work with the miRNA framework, or a new aptamer can be selected for the desired ligand.

Ligands

Any ligand that can bind to a sensor domain can be used. In some embodiments, the ligand is selected from the group consisting of polypeptides, peptides, nucleic acids, carbohydrates, fatty acids, lipids, non-peptide hormones, and metabolic precursors or products thereof. In some embodiments, the ligand of the aptamer is endogenous to a cell. Such endogenous ligands include products produced by a cell or organism that are found within a cell. In some embodiments, production of, release of, or uptake of an endogenous ligand can be stimulated or controlled by another external stimulus or ligand.

In some embodiments, the ligand is exogenous to a cell. In some embodiments, the ligand is cell permeable. In some embodiments, the cell permeable ligand is a small organic molecule. In some embodiments, the ligand has a molecular weight less than about 2.5 kDa, less than about 1 kDa, or less than about 500 kDa.

Any ligand can be used in combination with an appropriate RNA sensor domain, including those for which aptamers are known. In some embodiments, the ligand is theophylline, tetracycline, phenobarbital, tamoxifen, folinic acid, vitamin B12, biotin, Rev, Tat, dopamine, p50, p65, B-catenin, SAM, SAH, TPP, vitamin B1, adenine, or guanosine.

In certain embodiments, the ligand of the aptamer of an aptamer-regulated nucleic acid of the invention is a cell-permeable, small organic molecule. Small organic molecules which do not have a general inhibitory effect on cell viability are preferred as ligands. The small molecule preferably also exhibits in vivo persistence sufficient for achieving the desired level of inhibition of translation. The molecules also can be screened to identify those that are bioavailable after, for example, oral administration. In certain embodiments of the invention, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to theophylline.

Aptamers are known that bind to a variety of molecules. Such aptamers can be used. For example, aptamers are known that bind: isoleucine (Lozupone et al., RNA (2003) Vol. 9, Issue 11, pages 1315-22); Coenzyme A (Saran et al. BMC Evol. Biol. (2003) Vol. 3, Issue 1, pages 26); dopamine (Mannironi et al. Biochemistry (1997) Vol. 36, Issue 32, pages 9726-34); HIV-1 RRE (Boiziau et al. Journal of biological chemistry (1999) Vol. 274, Issue 18, pages 12730-37); ATP (Vaish et al., Biochemistry (2003) Vol. 42, Issue 29, pages 8842-8851); codeine (Win et al., RNA (2006) Vol. 34, Issue 19, pages 5670-82); FAD (Roychowdhury-Saha et al., Biochemistry (2002) Vol. 41, Issue 8, pages 2492-9); Vascular Endothelial Growth Factor (VEGF165) (Ruckman, et al. J. Biol. Chem. (1998) Vol. 273, Issue 32, pages 20556-67); arginine (Tao et al., Biochemistry (1996) Vol. 35, Issue 7, pages 2229-38); S-adenosyle methionine (Burke et al. Nucleic Acids Research (1997) Vol. 25, Issue 10, pages 2020-4); neuroeptide Y (Mendonsa et al., J. Am. Chem. Soc. (2005) Vol. 127, Issue 26, pages 9382-3); human complement C5 (Biesecker et al, Immunopharmacology (1999) Vol. 42, Issue 1-3, pages 219-30); K Ras-Derived Farnesylated Peptide (Gilbert et al. Bioorg. Med. Chem. (1997) Vol. 5, Issue 6, pages 1115-22); Escherichia coli rho factor (Schneider et al, FASEB J. (1993) Vol. 7, Issue 1, pages 201-7); Pepocin (Hirao et al., Journal of Biological Chemistry (2000) Vol. 275, Issue 7, pages 4943-8); Ras-binding domain of Raf-1 (Kimotoa et al., FEBS Lett. (1998) Vol. 441, Issue 2, pages 322-6); cellobiose (Yang et al., PNAS (1998) Vol. 95, Issue 10, pages 5462-7); L-arginine (Geiger et al, Nucleic Acids Research (1996) Vol. 24, Issue 6, pages 2755-8); streptavidin (Tahiri-Alaoui et al., Nucleic Acids Res. (2002) Vol. 30, Issue 10, pages e45); cholic acid (Kato et al., Biochim. Biophys. Acta (2000) Vol. 1493, Issue 1-2, pages 12-8); Cyanocobalamin (Lorsch et al., Biochemistry (1994) Vol. 33, Issue 4, pages 973-82); HIV-1 Tar element (Boiziau et al., Antisense Nucleic Acid Drug Dev. (1997) Vol. 7, Issue 4, pages 369-80; Duconge et al., RNA (1999) Vol. 5, Issue 12, pages 1605-14); Tenascin-C (Hicke et al., J. Biol. Chem. (2001) Vol. 276, Issue 52, pages 48644-54); cocaine (Ulrich et al., Proc. Natl. Acad. Sci. USA (1998) Vol. 95, Issue 24, pages 14051-6); S-Adenosylhomocysteine (Gebhardt, Biochemistry (2000) Vol. 39, Issue 24, pages 7255-65); Isoleucine (Legiewicz et al., J. Biol.

Chem. (2005)); Sialyl Lewis (Jeong et al., Biochemical and Biophysical Research Communications (2001) Vol. 281, Issue 1, pages 237-43); CD4 (Kraus et al, J. Immunol. (1998) Vol. 160, Issue 11, pages 5209-12); carcinogenic aromatic amines (Brockstedt et al., Biochem. Biophys. Res. Commun. (2004) Vol. 313, Issue 4, pages 1004-8); chitin (Fukusaki et al., Bioorg. Med. Chem. Lett. (2000) Vol. 10, Issue 5, pages 423-5); HCV NS3 protease (Urvil et al., European Journal of Biochemistry (1997) Vol. 248, Issue 1, pages 130-8); streptomycin (Wallace et al., RNA (1998) Vol. 4, Issue 1, pages 112-23); substance P (Eulberg et al., Nucleic Acids Res. (2005) Vol. 33, Issue 4, pages e45); Elongation Factor Tu (Hornung et al., Biochemistry (1998) Vol. 37, Issue, pages 7260-7); camp (Koizumi et al., Biochemistry (2000) Vol. 39, Issue 30, pages 8983-92); Hemagglutinin (Gopinath et al., J Biochem (Tokyo) (2006) Vol. 139, Issue 5, pages 837-46; Misono et al. Anal. Biochem. (2005) Vol. 342, Issue 2, pages 312-7); Raf-1 (Kimoto et al., Eur. J. Biochem. (2002) Vol. 269, Issue 2, pages 697-704); aminoglycoside antibiotics (Wang et al., Biochemistry (1996) Vol. 35, Issue 38, pages 12338-46); Subtilisin (Takeno et al., Journal of Biochemistry (1999) Vol. 125, Issue 6, pages 1115-9); factor VIIa (Thromb. Haemost. (2000) Vol. 84, Issue 5, pages 841-8); thrombin (Liu, et al., Journal of Molecular Recognition (2003) Vol. 16, Issue 1, pages 23-27); 7-methyl-guanosine binding RNA (Haller et al., PNAS (1997) Vol. 94, Issue 16, pages 8521-6); malachite green (Flinders et al., Chembiochem (2004) Vol. 5, Issue 1, pages 62-72); tenascin-C (Daniels, PNAS (2003) Vol. 100, Issue 26, pages 15416-21); Ricin A-chain (Hesselberth et al., Journal of Biological Chemistry (2000) Vol. 275, Issue 7, pages 4937-42).

Aptamers are typically developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

An improved aptamer selection scheme is described in the co-owned and co-pending U.S. application Ser. No. 12/218, 628, filed on Jul. 16, 2008, the entire content of which is incorporated herein by reference.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to switch an aptamer-regulated nucleic acid of the invention between "on" and "off" states of an aptamer-regulated nucleic acid.

The association constant for the aptamer and associated ligand is preferably such that the ligand functions to bind to the aptamer and has the desired effect at the concentration of ligand obtained upon administration of the ligand. For in vivo use, for example, the association constant should be such that binding occurs well below the concentration of ligand that can be achieved in the serum or other tissue, preferably well below the concentration of ligand that can be achieved intracellularly since cellular membranes may not be sufficiently permeable to allow the intracellular ligand concentration to approach the level in the serum or extracellular environment. Preferably, the required ligand concentration for in vivo use is also below that which could have undesired effects on the organism.

Vectors

The nucleic acid systems described herein can be part of any larger nucleic acid vector. One of skill in the art will recognize that a particular vector can be selected for its ability to be propagated or the ability to deliver a nucleic acid to a desired cell.

The vectors can be propagated in cells extrachromosomally or can be integrated into chromosomes of a cell. For example, certain viral vectors can integrate a vector containing a nucleic acid system of the invention into a cell.

In some embodiments, the nucleic acid systems of the invention are part of plasmid. In some embodiments, the nucleic acid systems are in viral vectors, such a lentiviral vectors. In some embodiments, the vector can direct integration of the nucleic acid system into the chromosomal DNA of a cell.

Vectors can include promoters, enhancers and other sequences that can facilitate transcription of the miRNA.

Target RNA Transcripts

In some embodiments, the miRNA sequence will have at least one guide sequence region that is complementary to a target RNA transcript. In some embodiments, the guide sequence region is at least, great than or between 10, 11, 12, 13, 14, 15, 16, 17, 18, 19, 20, 21, 22, 23, 24, 25 and 26 nucleotides in length. The target RNA transcript can be any RNA transcript expressed in a cell, including, for example, mRNAs and naturally-occurring miRNAs. Natural miRNAs are key players in diverse cellular processes and help enact global changes in gene expression by simultaneously targeting hundreds of genes. Therefore, ligand-responsive miRNAs can be directly interfaced with the regulatory architecture controlling complex cellular processes. By implementing ligand responsive miRNAs that respond to endogenously-expressed molecules, these regulatory molecules will provide a platform for reprogramming cellular state according to the intracellular environment, supporting autonomous approaches to tissue engineering and disease treatment.

In some embodiments, the target mRNA transcript is down regulated when a ligand is applied to a cell having a nucleic acid system. In some embodiments, the target RNA transcript is up regulated. In some embodiments, the target RNA transcripts are regulated through an RNA interference pathway. Target RNA transcripts can be cleaved or repressed by the RNA interference pathway, depending, in part on the degree of complementarity between the guide sequence region and the target RNA sequence.

Clusters

In some embodiments, the systems of the invention can include multiple miRNA sequences within the nucleic acid system.

In some embodiments, a nucleic acid system has more than one miRNA nucleic acid, and more than one sensor domain. In some embodiments, the nucleic acid system has multiple copies of the same miRNA nucleic acid, each with a RNA sensor domain, separated by an appropriate number of nucleotides. The RNA sensor domains for each of the repeated miRNA nucleic acids can be identical or can be unique. For example, a cluster of miRNAs with sensor domains sensitive to multiple ligands can be used. In such an embodiment, the regulation of the miRNA can be accomplished through multiple ligands. In some embodiments, multiple copies of the same miRNA-sensor domain combination can be used to increase the dynamic range of response to the same ligand. Our results also indicate that the variable spacing and secondary structure within intervening sequences of natural-occurring miRNA clusters may be a key factor in miRNA processability and an evolutionary factor to tune miRNA processing and subsequent gene silencing activity. miRNA processability generally increases with longer intervening sequences. The intervening sequence length should be at least 10 nucleotides. More preferably, the intervening sequence length should be at least 50 nucleotides and more preferably at least 100 nucleotides.

In some embodiments, the nucleic acid system has more than one miRNA nucleic acids, with each having a sensor domain. The sensor domains for each miRNA can be unique or can be the same.

Cells

In some embodiments, cells including nucleic acid systems are provided. Any cell type can be used, regardless of whether the miRNA has activity in that cell type. For example, a bacterial cell can be used to propagate or manipulate a nucleic acid system. Since natural bacterial cells do not have an RNA interference pathway, the miRNA will generally not have activity against a target RNA sequence in a bacterial cell. However, if such a cell were to express components of the RNA interference pathway, the miRNA may be active.

In some embodiments, the cells include any eukaryotic cell. In some embodiments, the cells are plant cells. In some embodiments, the cells are mammalian cells. In one embodiment, cells are cultured human HEK 293 cells.

Kits

In some embodiments, kits are provided that include a nucleic acid system of the invention. In some embodiments, the kit includes a nucleic acid with an miRNA sequence with an appropriate restriction site or restriction sites into which a guide sequence for an RNA target sequence can be inserted. In some embodiments, the nucleic acid in the kit will include a sensor domain that binds to a ligand. In some embodiments, the kit also includes a sample of the ligand. In some embodiments, the nucleic acid of the kit also includes a reporter gene, the expression of which can be monitored. In such an embodiment, a nucleic acid in the kit will include a guide sequence in the miRNA that is complementary to the reporter gene. In some embodiments, the reporter gene is a fluorescent protein, such as GFP.

EXAMPLES

Example 1

Extent of Structure in the Basal Segments Dictates Drosha Processing and Gene Silencing miRNAs can be partitioned into four domains (FIG. 1A) that exhibit unique structural requirements for efficient Drosha processing and RISC activation (Han et al., 2006; Zeng and Cullen, 2003, 2005; Zeng et al., 2005). In vitro studies have shown that mutating the sequence of the basal segments to form extensive base pairing interactions abolishes Drosha processing (Han et al., 2006; Zeng and Cullen, 2005), suggesting a mechanism for regulating Drosha processing by regulating the structure of the basal segments. To utilize this potential mechanism as a design strategy, we needed to develop a more thorough understanding of how structure in the basal segments, and in particular extents of structure, affect Drosha processing and RNAi-mediated gene silencing in vivo. Therefore, we systematically examined the relationship between bulge size in the miRNA basal segments, in vitro Drosha processing, and in vivo gene silencing.

We performed in vitro Drosha cleavage assays that mimic the first step in miRNA biogenesis to examine the relationship between bulge size and Drosha processing. RNAs with varying bulge sizes in the basal segments (FIG. 1B) were transcribed in vitro, incubated with immunopurified Drosha, and resolved by PAGE (FIG. 1C). Decreasing the size of the loop from 18 to 8 nts greatly reduced the appearance of the 61 nt pre-miRNA (FIG. 1B, black arrows) and increased abortive processing (FIG. 1B, gray arrows) in a manner that correlated with bulge size. Such abortive processing has been previously observed in vitro and attributed to DGCR8 recognition of the terminal loop instead of the miRNA basal segments (Han et al., 2006).

To examine the relationship between bulge size in the basal segments and gene silencing, we developed a general cell culture assay for miRNA activity (FIG. 1D). miRNAs designed to target a transcript encoding the green fluorescent protein (GFP) were inserted into the 3' untranslated region (UTR) of a constitutively-expressed transcript encoding the fluorescent protein DsRed-Express. Plasmid DNA encoding the DsRed-Express construct was transfected into HEK 293 cells stably expressing GFP. The level of miRNA-mediated gene silencing was determined by flow cytometry analysis, where DsRed-Express levels were used to distinguish between transfected and untransfected cells. Using the cell culture assay, miRNAs with the same bulges as in the in vitro experiments were tested for silencing efficiency. Flow cytometry results supported the data from the in vitro Drosha cleavage assays, as smaller bulge sizes showed reduced GFP silencing (FIG. 1E). Therefore, proper Drosha processing and gene silencing correlate with the size of the bulge in the miRNA basal segments.

Example 2

Figure 2:
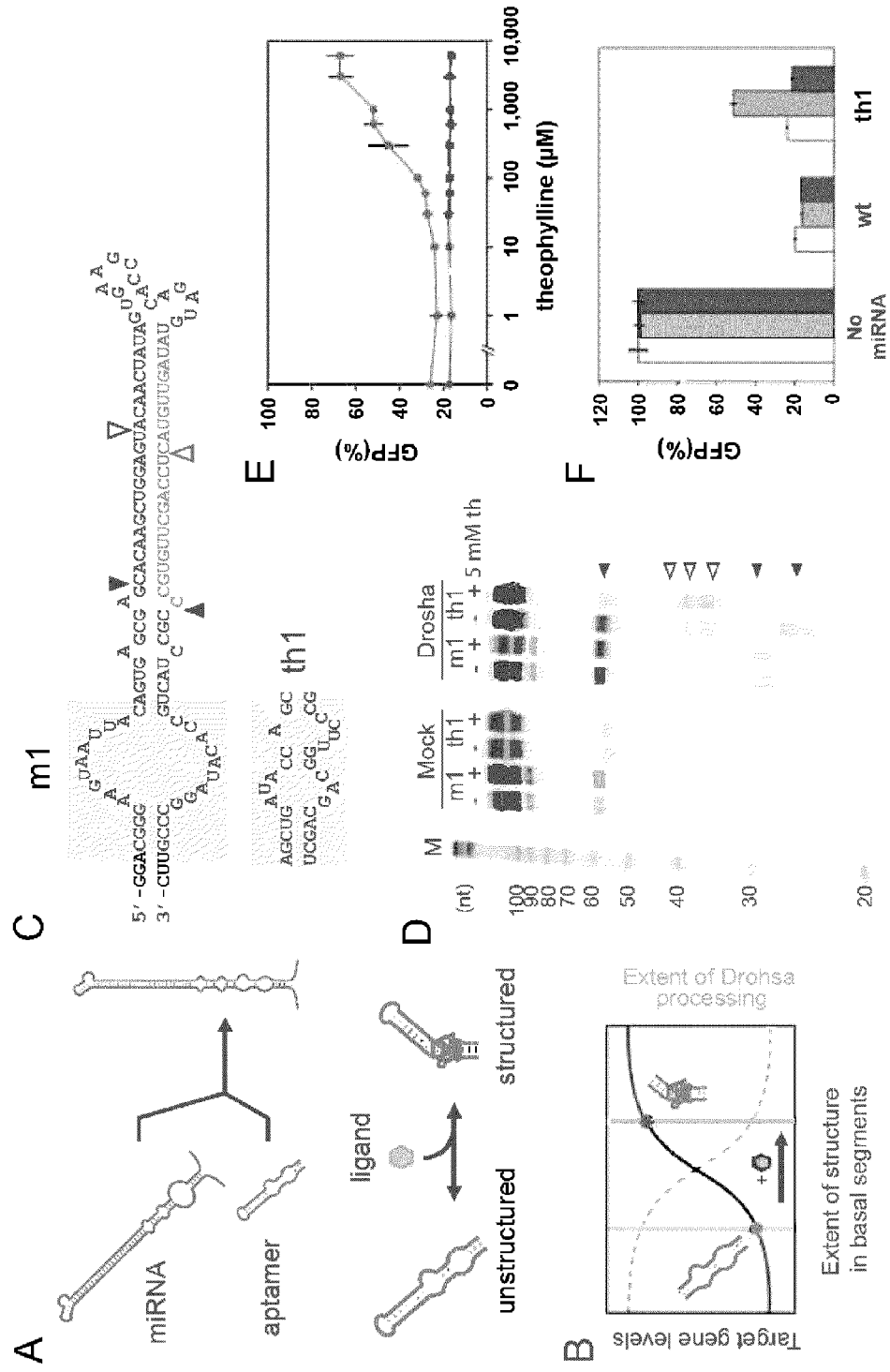
FIG. 2 shows ligand-responsive miRNAs enable ligand control of Drosha processing and gene silencing. (A) Design framework for ligand-responsive miRNAs. The aptamer binding core is integrated into the miRNA basal segments adjacent to the lower stem. Ligand binding increases the structured nature of the aptamer. (B) Relationship between Drosha processing (dashed gray line), target gene expression levels (black line), miRNA basal segments structure, and ligand addition mediated by a ligand-responsive miRNA. Unstructured basal segments lead to efficient processing and gene silencing. Structured basal segments resulting from ligand binding inhibit Drosha processing. (C) Sequence and secondary structures of minimal pri-miRNAs with a large bulge (m1) or the theophylline aptamer (th1) inserted in the basal segments. See FIG. 1B for notation. (D) PAGE analysis of m1 and th1 subjected to the Drosha cleavage assay in the presence or absence of 5 mM theophylline. See FIG. 1C for notation. (E) Relative GFP levels obtained from the cell culture assay for constructs harboring th1 (blue) or a miRNA with basal segments similar to miR-30a (wt, gray). See FIGS. 1D,E for description of the assay. Transient transfections were conducted in the presence of varying theophylline concentrations. (F) Relative GFP levels obtained from the cell culture assay for constructs transiently transfected in the absence (white) or presence of 1 mM theophylline (gray) or 1 mM caffeine (black). Error bars represent the standard deviation of two independent transfections.

Aptamer Integration Renders miRNA Processing Sensitive to a Small Molecule Ligand Aptamers often undergo transitions from relatively unstructured to structured conformations upon ligand binding, a phenomenon termed adaptive recognition (Hermann and Patel, 2000). We developed a design strategy based on this phenomenon and the elucidated dependence of Drosha processing on the structure of the basal segments to introduce ligand control of miRNA-mediated gene silencing (FIG. 2A). Through integration of an aptamer into the basal segments of a miRNA, we hypothesized that the aptamer-ligand binding interactions would be able to sufficiently decrease the unstructured nature of that region to result in inhibition of proper processing and subsequent gene silencing (FIG. 2B).

Figure 7:
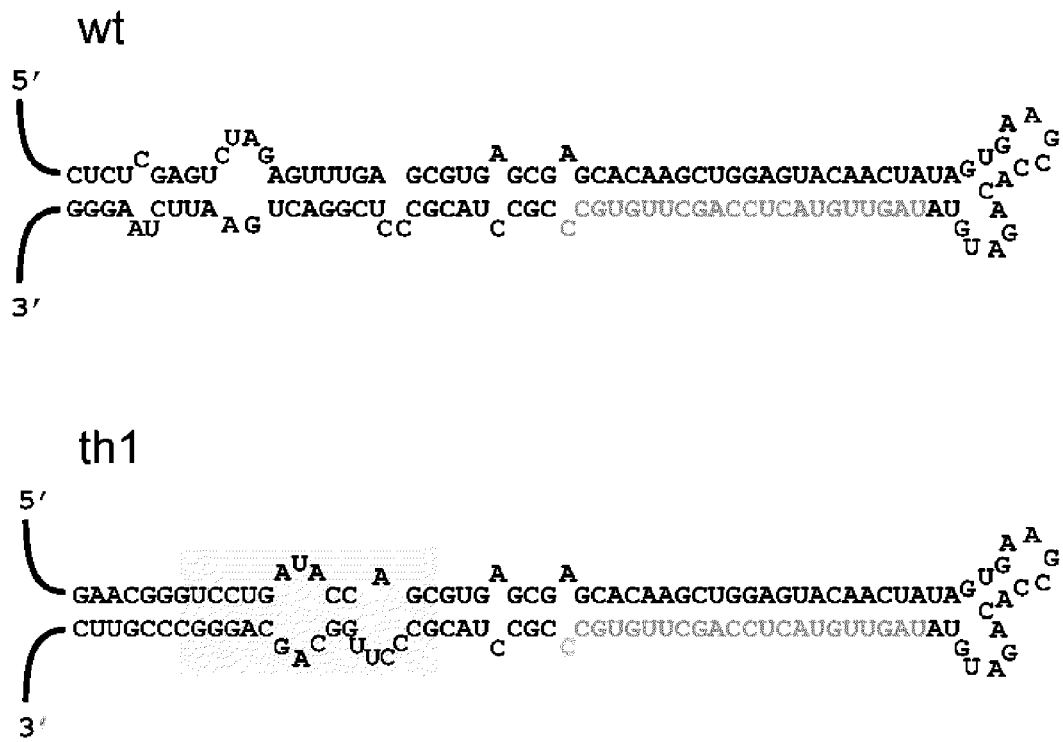
FIG. 7 shows sequence and secondary structure of miRNAs targeting GFP. Basal segments contain sequences that are similar to miR-30a (wt) or the theophylline aptamer (th1). The aptamer insertion site is indicated by the yellow box according to FIG. 3A and the mature miRNA sequence complementary to the GFP transcript is indicated in green text.

We first examined the ability of an aptamer to mediate ligand control of Drosha processing. The theophylline aptamer (Denison et al., 1994) was inserted in the basal segments domain directly adjacent to the miRNA lower stem (FIG. 2C). The resulting miRNA (th1) was transcribed in vitro and subjected to the Drosha cleavage assay in the presence or absence of theophylline. The primary products of Drosha processing for th1 and a control miRNA were both ~61 nts, the expected size for the pre-miRNA (Han et al., 2006; Lee et al., 2003) (FIG. 2D). In addition, the presence of theophylline inhibited proper processing of the aptamer-containing miRNA, resulting in an alternative cleavage pattern similar to that observed from miRNAs with smaller bulges (FIG. 1C). The control miRNA exhibited negligible theophylline dependence, suggesting that ligand binding to an aptamer located within the basal segments can control Drosha processing. We next examined whether theophylline regulation of Drosha processing resulted in ligand-mediated control of gene silencing. Using the cell culture assay, we tested the silencing efficiency of a GFP-targeting miRNA with a theophylline aptamer in the basal segments (th1). Extensive base pairing below the bulge encoded in the aptamer sequence was incorporated to ensure proper aptamer folding. We also included a GFP-targeting miRNA with basal segments similar to the natural miRNA miR-30a as a control (wt, FIG. 7). Transient transfections were conducted in the presence of varying concentrations of theophylline. Results show that both miRNA constructs silence GFP with comparable strength in the absence of theophylline (FIG. 2E). However, the miRNA with the theophylline aptamer mediated a theophylline dose-dependent increase in GFP expression levels, whereas silencing by the miRNA lacking the aptamer was insensitive to theophylline. In addition, silencing by both miRNAs was insensitive to the presence of caffeine (FIG. 2F), a molecule that differs from theophylline by a single methyl group and binds the theophylline aptamer with a 10,000-fold lower affinity (Denison et al., 1994). A caffeine concentration of 1 mM was used to avoid the pronounced toxicity observed at higher concentrations (An et al., 2006). The results demonstrate that the observed effect of theophylline on miRNA-mediated gene silencing is specific to the incorporation of the theophylline aptamer in the basal segments of the miRNA.

Example 3

Framework Modularity Supports the Integration of Different Aptamer and miRNA Targeting Sequences Ligand-responsive regulatory systems that display modularity can be readily modified to change the targeted gene or recognized ligand without complete redesign. Such systems are useful in facilitating the rapid implementation of base designs in diverse applications with varying regulatory needs. While most ligand-responsive RNA regulator designs can be readily modified to target different genes, only a fraction of the developed designs have been shown to support direct insertion of different aptamer sequences (Bayer and Smolke, 2005; Beisel et al., 2008; Win and Smolke, 2007).

Figure 8:
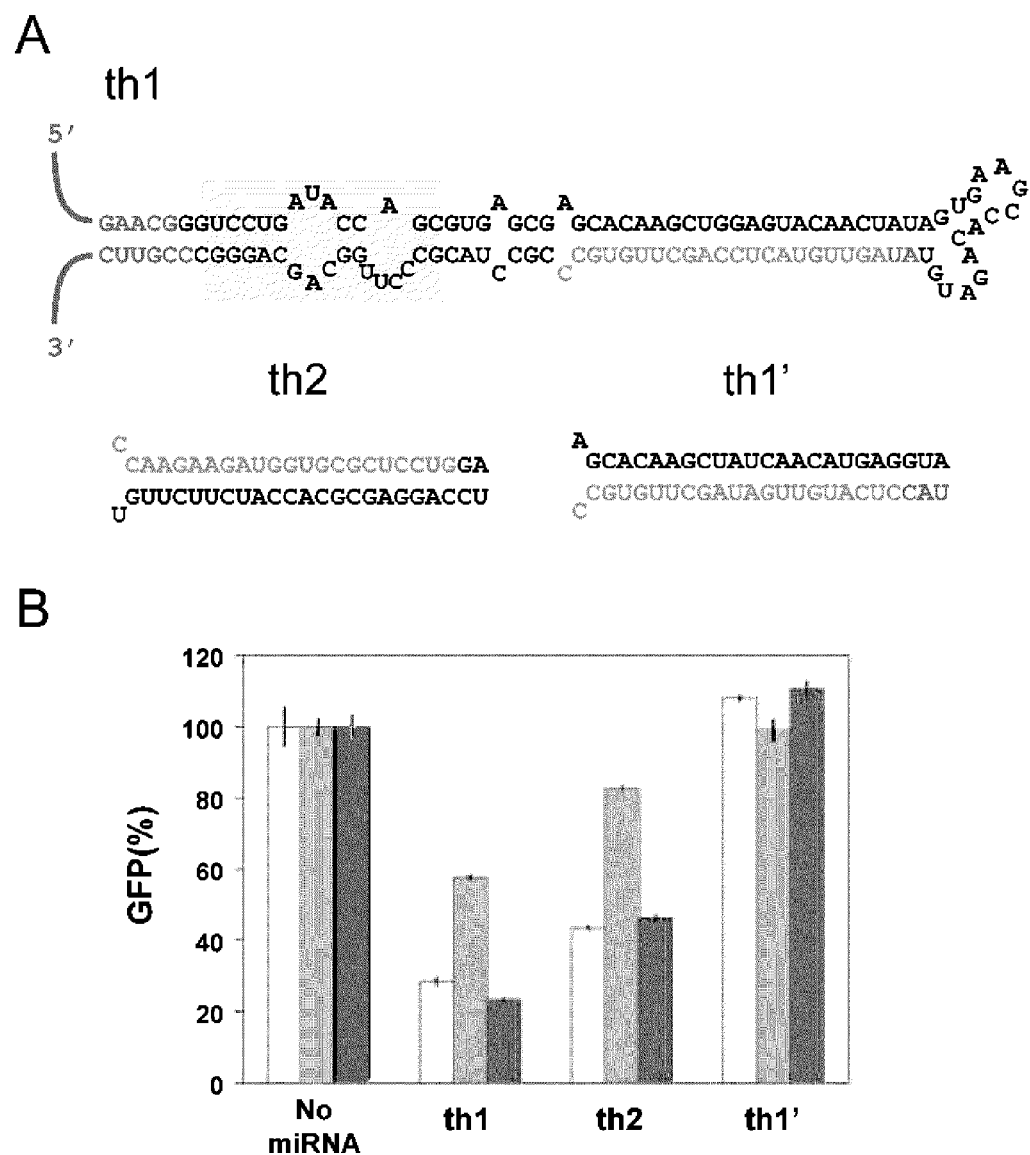
FIG. 8 shows ligand-responsive miRNAs can accommodate different mature miRNA sequences to tailor the gene silencing output of the regulatory system. (A) The mature miRNA sequence contained within the upper stem of th1 was modified to target a different sequence within the GFP mRNA (th2) or abolish targeting (th1'). All miRNAs contain the theophylline aptamer in the basal segments. The aptamer insertion site is indicated by the yellow box according to FIG. 3A, and mature miRNA sequences are indicated in green text. The GFP-targeting miRNAs were cloned into the plasmid constructs and characterized through the cell culture assay described in FIGS. 1D,E. (B) GFP silencing results for theophylline-responsive miRNA constructs (th1, th2, or th1') transiently transfected in the absence (white) or presence of either 5 mM theophylline (gray) or 1 mM caffeine (black). See Materials and Methods for a description of data normalization. Error bars represent the standard deviation of two independent transfections.

The targeted gene is specified by the mature miRNA sequence in a miRNA regulatory element. Previous work has shown that modifying the mature miRNA sequence in natural miRNAs is sufficient to target different genes (Zeng et al., 2002). We demonstrated that altering th1 to target a different location in the GFP transcript (th2) preserved silencing and the theophylline response in the cell culture assay, while scrambling the mature miRNA sequence (th1') abolished silencing (FIG. 8). Therefore, the mature miRNA sequence can be modified in our ligand-responsive miRNA framework without compromising the ligand control function encoded within the aptamer sequence. To examine the modularity of the aptamer sequence and therefore the generality of our design strategy, we tested two aptamers that display different lengths and secondary structures: the tetracycline aptamer (Berens et al., 2001) and the xanthine aptamer (Kiga et al., 1998). The binding core of each aptamer was initially integrated adjacent to the lower stem in place of the bulge (FIG. 3A), and the resulting miRNAs were tested using the cell culture assay in the presence or absence of the cognate ligand.

Figure 3:
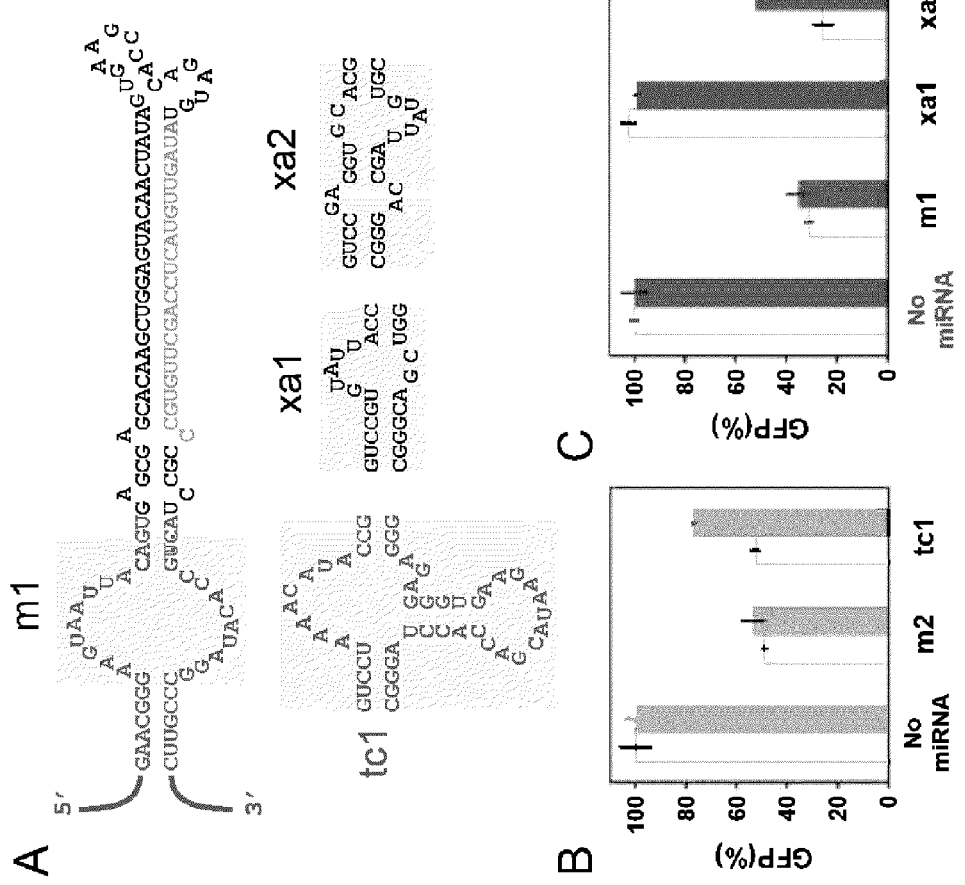
FIG. 3 shows ligand-responsive miRNAs can accommodate different aptamers to tailor the input-responsiveness of the regulatory system. (A) Sequence and secondary structure of GFP-targeting miRNAs with the tetracycline (tc1) or hypoxanthine (xa1, xa2) aptamers inserted in the basal segments. tc1 and xa1 contain the aptamer binding core, xa2 contains the aptamer binding core and loop. See FIG. 1B for notation. (B,C) Relative GFP levels obtained from the cell culture assay for constructs transiently transfected in the absence white) or presence of either 100 μM tetracycline (gray) or 5 mM hypoxanthine (black). See FIGS. 1D,E for description of the assay. m1 and m2 were used as negative controls as they result in similar levels of GFP silencing as xa2 and tc1, respectively, in the absence of ligand. Error bars represent the standard deviation of two independent transfections.

Hypoxanthine was used as a soluble alternative to xanthine that binds the aptamer with comparable affinity (Kiga et al., 1998). Control miRNAs that resulted in similar levels of gene silencing as the ligand-responsive miRNAs in the absence of ligand were also tested to determine any non-specific impacts of ligand addition on GFP levels. The miRNA harboring the tetracycline aptamer (tc1) down-regulated GFP and mediated a tetracycline-dependent increase in GFP levels (FIG. 3B). The control miRNA (m2) delivered a similar extent of silencing with negligible tetracycline dependence, indicating that insertion of the tetracycline aptamer rendered gene silencing sensitive to tetracycline. However, compared to the theophylline aptamer, insertion of the tetracycline aptamer imparted reduced silencing and ligand sensitivity. The altered silencing in the absence of ligand may be attributed to the nature of the unbound aptamer structure, where the tetracycline aptamer folds into a preformed pocket (Muller et al., 2006). The altered regulatory response may be attributed to aptamer affinity, the relative membrane permeability of each small molecule, and the extent to which each aptamer adopts a more structured conformation upon ligand binding.

In contrast, insertion of the binding core of the xanthine aptamer (xa1) completely abolished silencing (FIG. 3C). The size of the bulge in the basal segments of xa1 was similar to m4, the miRNA with the smallest bulge tested (FIG. 1B), such that the small size of the xanthine binding core may similarly prevent proper Drosha processing. We hypothesized that an aptamer with a small binding core bulge can be made more unstructured by including additional bulges, thereby restoring proper processing. Most aptamers selected in vitro contain loops that are separate from the binding core. To decrease the structure of the basal segments without compromising binding activity, we included the loop of the original xanthine aptamer and inverted the aptamer sequence to ensure hypoxanthine binding was proximal to the lower stem (xa2). Results from the cell culture assay showed substantial GFP silencing and a hypoxanthine-dependent increase in GFP levels (FIG. 3C), whereas hypoxanthine had no effect on a control miRNA with a similar silencing strength (m1). Therefore, these studies supported the generality of our design strategy based on the demonstrated ability of aptamer-ligand binding interactions to modulate miRNA structure sufficiently between processable and unprocessable conformations.

Example 4

Engineering Ligand-Responsive miRNA Clusters for Tunable Genetic Control

Multiple miRNAs can be naturally found in clusters within a single transcript (Zhang et al., 2009), allowing cells to efficiently regulate multiple miRNAs from a single promoter. By integrating multiple miRNAs into the same transcript, researchers have exploited this architecture to target multiple genes or tune gene silencing (Aagaard et al., 2008; Sun et al., 2006; Xia et al., 2006). Integrating ligand-responsive miRNAs into clusters would allow tuning of the regulatory response, simultaneous regulation of different targets, and multi-input control.

Figure 4:
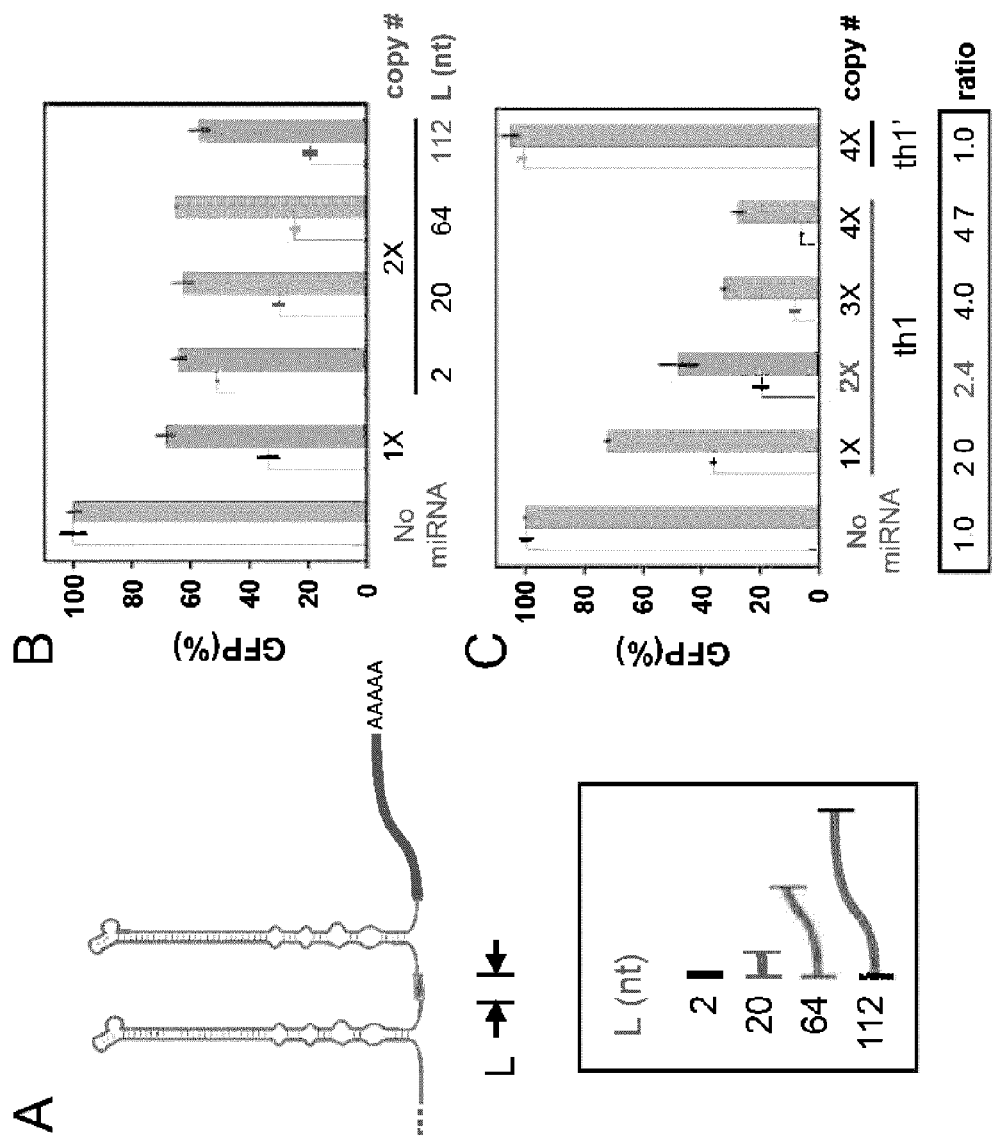
FIG. 4 shows that synthetic ligand-responsive miRNA clusters allow tuning of the regulatory response. (A) Schematic of a synthetic miRNA cluster in which multiple ligand responsive miRNAs are placed in the 3' UTR of a transgene encoding transcript. The spacer sequence downstream of each miRNA (indicated as a thicker line) was kept consistent, and the spacer length (L) was varied between 2 and 112 nts. Multiple copies (from 1 to 4) of a single miRNA were sequentially inserted. (B) The impact of spacer length between two theophylline-responsive GFP-targeting miRNAs (2X, th1) on gene silencing in the presence (gray) or absence (white) of 5 mM theophylline. The GFP-targeting miRNAs were cloned into the plasmid constructs and characterized through the cell culture assays described in FIG. 1D. GFP levels are reported as described in FIG. 2F. The GFP silencing from a single-copy theophylline-responsive miRNA construct (1X, th1) is shown for comparison. (C) The impact of ligand-responsive miRNA copy number on gene silencing and dynamic range. Multiple copies (#X) of the GFP-targeting (th1) or non-targeting (th1', FIG. 8) theophylline-responsive miRNAs were cloned into the plasmid constructs described in FIG. 1D using the largest spacer length tested (112 nt). GFP levels were characterized and reported as described in B, and the dynamic range is reported as the ratio of GFP levels in the presence and absence of theophylline.

To begin constructing ligand-responsive miRNA clusters, we first examined how the spacer length between miRNAs affects gene silencing and ligand. Spacing length may be important in Drosha processing and gene silencing for both natural and synthetic miRNA clusters. We inserted a second copy of the theophylline-responsive, GFP-targeting miRNA (th1) upstream from the first copy in the 3' UTR of the transcript encoding DsRed-Express with different spacer lengths ranging from 2 to 112 nt (FIG. 4A) and performed the cell culture assay with theophylline. To keep the local sequence around each miRNA consistent, the spacer sequences were identical to the sequence downstream of the first miRNA up to the poly(A) signal. Adjacent placement of the miRNAs compromised both silencing and the response to theophylline potentially due to miRNA misfolding or steric hindrance of Drosha processing, whereas increased spacer length restored and even exceeded the silencing activity and theophylline-dependence from a single copy (FIG. 4B). The results suggest that separating the identical miRNAs a minimal distance improves processing and gene silencing.

Gene silencing and the dynamic range increased when two copies of a ligand-responsive miRNA were separated by the longest spacer tested (112 nt). As miRNAs in natural clusters are individually processed, we expected that inserting additional copies separated by appropriate spacer lengths would further improve silencing and the theophylline response. Constructs harboring up to four copies of the theophylline-responsive, GFP-targeting miRNA (th1) or four copies of the non-targeting variant (th1') separated by the longest spacer sequence were subjected to the cell culture assay. GFP silencing increased with each additional copy of th1, whereas four copies of th1' had no effect on GFP levels (FIG. 4C). The addition of each miRNA copy increased silencing and the dynamic range (measured as the ratio of GFP levels in the presence or absence of theophylline) by providing more miRNAs for Drosha recognition and more opportunities to inhibit processing. Therefore, changing the copy number of ligand-responsive miRNAs provides one approach to coordinately tune gene silencing and the dynamic range. The diminished GFP levels in the presence of theophylline may be attributed to the inability to access higher theophylline concentrations due to cytotoxicity (Beisel and Smolke, 2009) and incomplete inhibition of Drosha processing when theophylline is bound to the aptamer.

Example 5

Ligand-Responsive miRNA Clusters can Regulate Endogenous Genes

Figure 9:
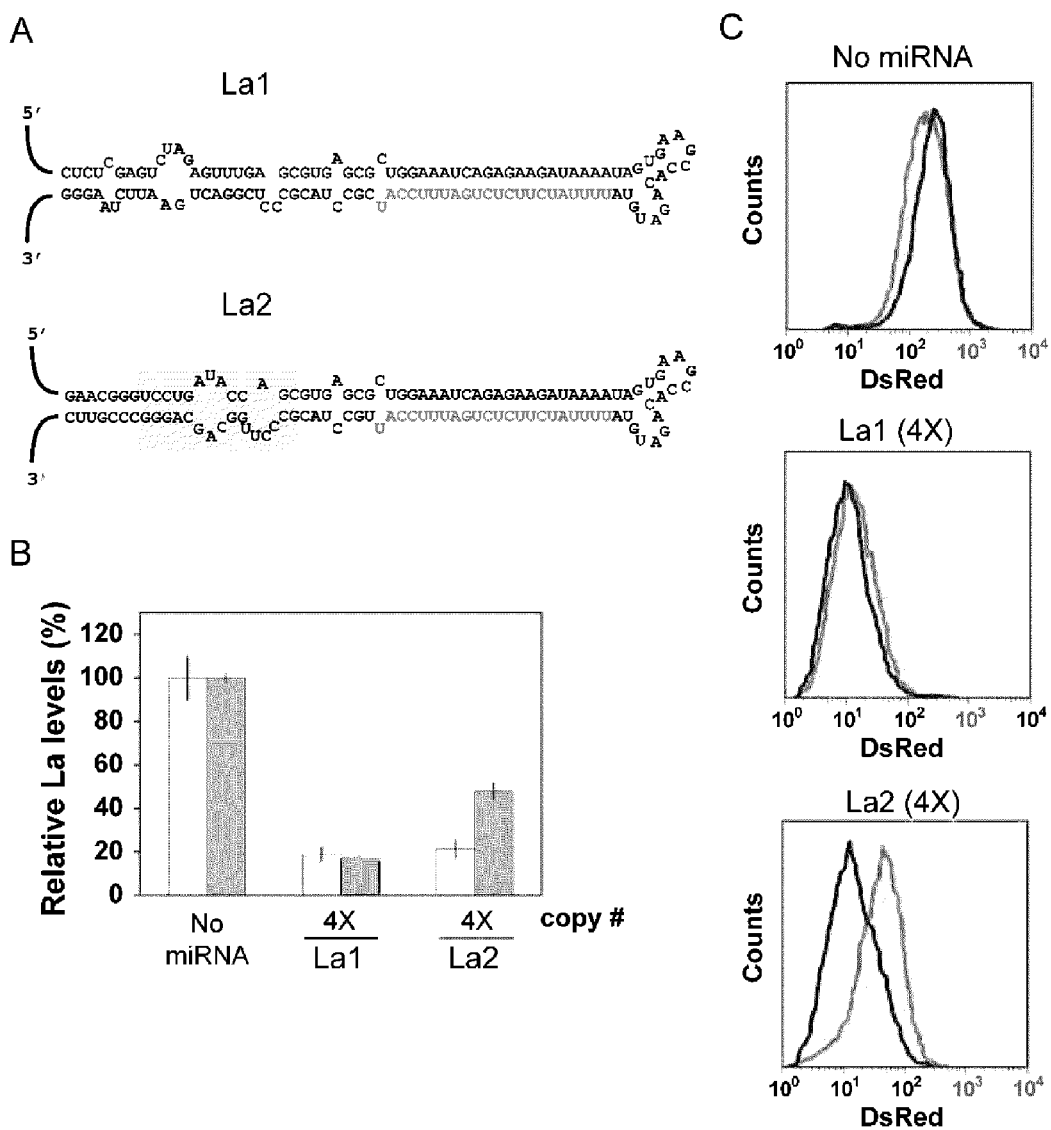
FIG. 9 shows ligand-responsive miRNA clusters can effectively control expression of endogenous gene targets. (A) Sequence and secondary structures of miRNAs that target the endogenous La gene. Color schemes are identical to FIG. 1B, except that the mature miRNA sequence complementary to the La transcript is indicated in red. Sequences similar to miR-30a (La1) or the theophylline aptamer (La2) were inserted into the miRNA basal segments. miRNAs were cloned into the plasmid constructs described in FIG. 1D at the indicated copy numbers using the largest spacer length tested (112 nt). The resulting constructs were stably transfected into HEK 293-Flp-In cells. (B) Relative La transcript levels for stable cell lines expressing the La-targeting miRNA constructs in the presence (gray) or absence (white) of 1.5 mM theophylline. La transcript levels were measured through qRT-PCR and normalized to GAPDH encoding transcript levels as an internal control. Relative levels are normalized to that of cells stably transfected with the construct lacking a miRNA (No miRNA) grown under the same conditions. Error bars represent the calculated error of quadruplicate qRT-PCR wells of each sample. (C) Flow cytometry histograms for DsRed levels from the La-targeting miRNAs. The stable cell lines tested in B were grown in the presence (lighter line) or absence (black) of 1.5 mM theophylline for over a week prior to flow cytometry analysis. Histograms are representative of two independent experiments.

Most of the synthetic ligand-responsive RNA-based regulatory systems are encoded in the target transcript, providing regulation in cis (Suess and Weigand, 2008). However, the regulation of endogenous genes through cis regulatory strategies is currently limiting due to the lack of directed recombination technologies. To test whether ligand-responsive miRNAs provide a trans regulatory strategy for the effective regulation of endogenous genes, we incorporated a mature miRNA sequence against the endogenous La gene into wt (La1) and th1 (La2) (FIG. 9). Four copies of each miRNA separated by the longest spacer sequence were cloned into the 3' UTR of the transcript encoding DsRed-Express, and the resulting constructs were stably integrated into a single site in 293-Flp-In cells. Stable cell lines were grown in the presence or absence of 1.5 mM theophylline for over one week and assayed for relative La transcript levels by qRT-PCR. The lower theophylline concentration was used for all stable expression studies to maintain 293 growth for extended periods of time (data not shown). Four copies of either La1 or La2 resulted in relatively strong silencing of the La target, and only La2 mediated a theophylline-dependent increase in La transcript levels (FIG. 9). The results demonstrate that ligand-responsive miRNAs can control endogenous genetic targets, providing a control strategy that does not physically disrupt the locus of the target gene.

Example 6

Ligand-Responsive miRNAs can Control Gene Expression in Cis

Figure 5:
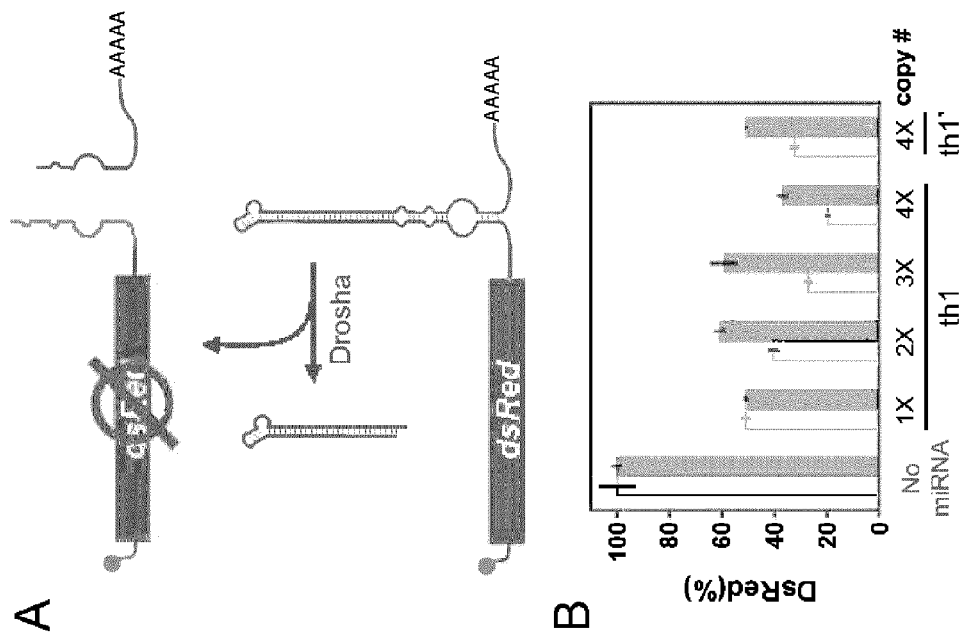
FIG. 5 shows ligand-responsive miRNAs can control transgene expression in cis. (A) Schematic of gene regulation in cis through miRNA cleavage. Drosha processing of the miRNA located in the 3' UTR of a transcript encoding DsRed Express separates the coding region from the poly(A) tail, thereby inactivating the transcript. (B) The impact of ligand-responsive miRNA copy number on expression of the transgene through regulation in cis in the presence (gray) or absence (white) of 5 mM theophylline. DsRed-Express levels of the constructs tested in FIG. 4C were characterized through identical cell culture assays. The population mean of DsRed-Express fluorescence from transiently transfected HEK 293 cells stably expressing GFP was normalized to that from a construct lacking any miRNAs (No miRNA) transfected under the same conditions. Error bars represent the standard deviation of two independent transfections.

Drosha cleavage is anticipated to separate the coding region from the poly(A) tail when the miRNA is located in the 3' UTR, resulting in the prevention of translation and facilitation of mRNA degradation (FIG. 5A). Drosha was recently shown to cleave a naturally-occurring pseudo-miRNA in the transcript of DGCR8 to regulate the activity of the Microprocessor (Han et al., 2009). In addition, introducing a 3' UTR-encoded miRNA was shown to down-regulate expression from the transcript harboring the miRNA (Stern et al., 2008).

Figure 10:
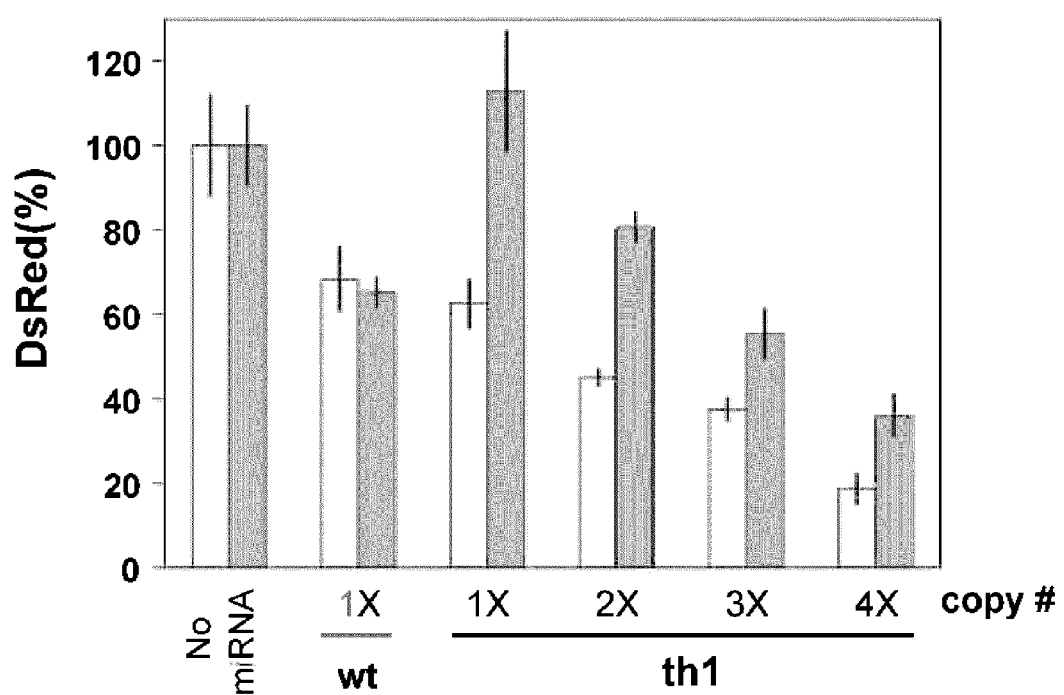
FIG. 10 shows ligand-responsive miRNAs control gene expression in cis through transcript destabilization. Multiple copies (#X) of the GFP-targeting theophylline-responsive miRNAs (th1) were cloned into the plasmid constructs described in FIG. 1D using the largest spacer length tested (112 nt). wt was used as a negative control to allow direct comparison to FIG. 4B. 293 cells stably expressing GFP were transiently transfected with the resulting constructs in the presence (gray) or absence (white) of 5 mM theophylline. DsRed transcript levels were measured through qRT-PCR and normalized to transcript levels of the Neomycin resistance gene expressed from the same transfected plasmid. Relative levels were normalized to that of cells transfected with the construct lacking a miRNA (No miRNA) grown under the same conditions. Error bars represent the calculated error of quadruplicate qRT-PCR wells for each sample.

To assess the capacity for ligand-responsive miRNAs to regulate gene expression in cis, we measured expression levels for the transcripts harboring the ligand-responsive miRNAs targeting GFP and La. DsRed-Express levels were quantified by flow cytometry under similar conditions as the trans-targeted gene silencing experiments. DsRed silencing increased with increasing copy number of the theophylline-responsive, GFP-targeting miRNA (th1), and two copies were sufficient to introduce ligand regulation (FIG. 5B). Similar effects were observed with four copies of the non-targeting miRNA (th1'), indicating that transcript silencing and ligand control are independent of downstream processing. Transcript analysis confirmed that the predominant regulatory mechanism of ligand-responsive miRNAs in cis is mRNA destabilization (FIG. 10). A similar analysis of the La-targeting miRNAs indicated that four copies of La1 or La2 resulted in substantial DsRed-Express down-regulation (FIG. 9). In addition, the miRNA containing the theophylline aptamer (La2) conferred an increase in DsRed levels in the presence of theophylline that was not observed for the construct lacking the theophylline aptamer (La1). These results suggest that ligand-responsive miRNAs can regulate transcripts in cis by modulating Drosha cleavage.

Example 7

Figure 6:
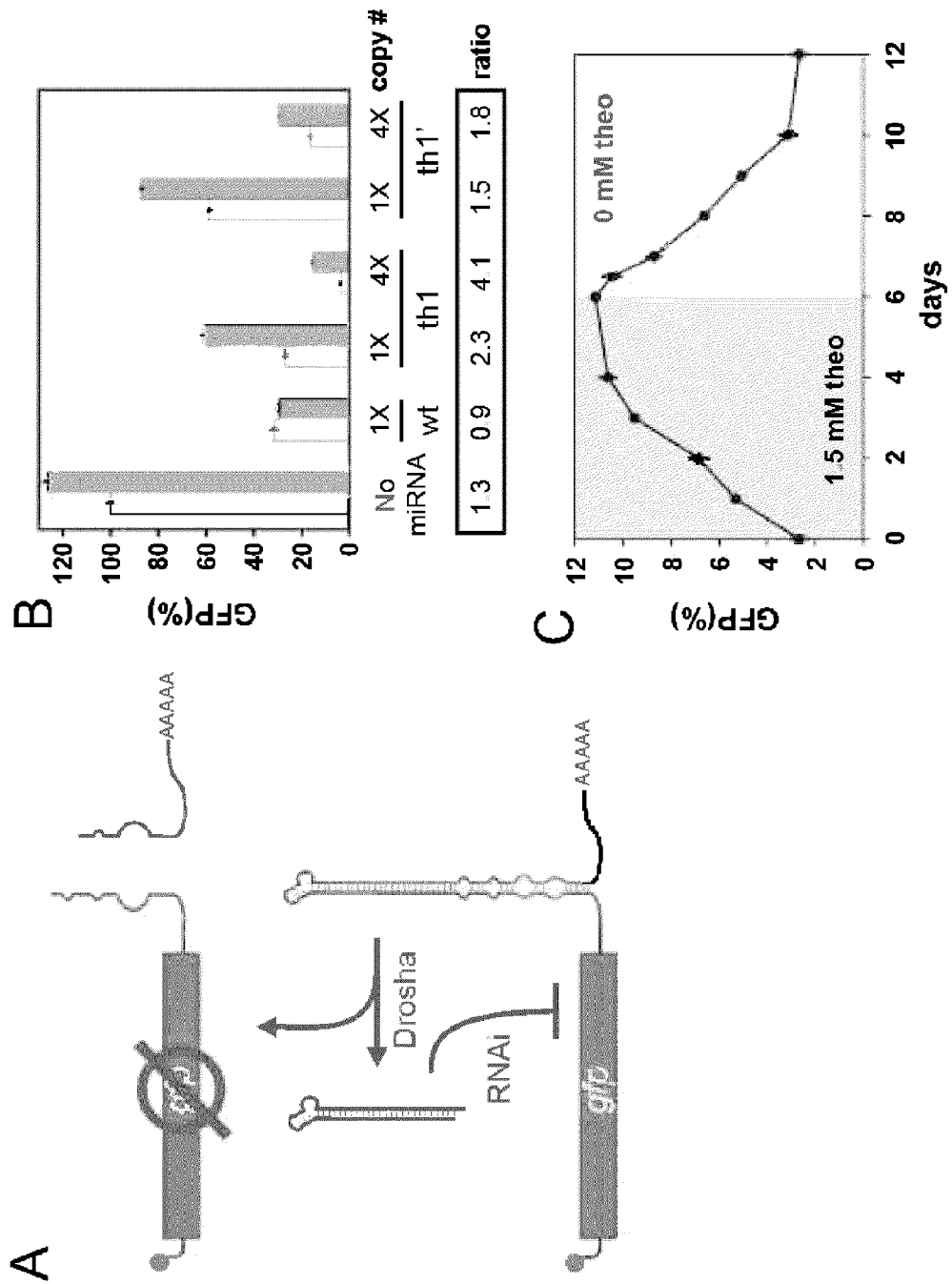
FIG. 6 shows that self-targeting miRNAs provide an enhanced regulatory response. (A) Schematic of the miRNA regulatory circuit associated with self-targeting miRNAs. Self-targeting miRNAs are located in the 3' UTR of the trans targeted transcript encoding GFP such that Drosha cleavage and RISC targeting down-regulate expression. Both events are inhibited by ligand binding to the aptamer contained in the miRNA basal segments. (B) Relative GFP levels for cells stably expressing the self-targeting miRNA constructs grown in the presence (gray) or absence (white) of 1.5 mM theophylline for over a week. Gene silencing from one (1X) or four (4X) copies of a theophylline-responsive self-targeting miRNA (th1) and one or four copies of a theophylline-responsive non-targeting miRNA (th1') were determined, where multiple copies were separated by the largest spacer length (112 nt). One copy of a self-targeting miRNA with basal segments similar to miR-30a (wt) was used as a negative control. The dynamic range is reported as the ratio of GFP levels in the presence and absence of theophylline. (C) Temporal response of the relative GFP levels to a change in ligand concentration for cell lines stably expressing ligand-responsive miRNAs. Representative time course data is shown for cells expressing the miRNA construct containing four copies of th1. Cells were grown in the presence of 1.5 mM theophylline for six days and then transferred to media without theophylline for six days. Error bars represent the standard deviation of cells grown in two separate culture wells.
Figure 11:
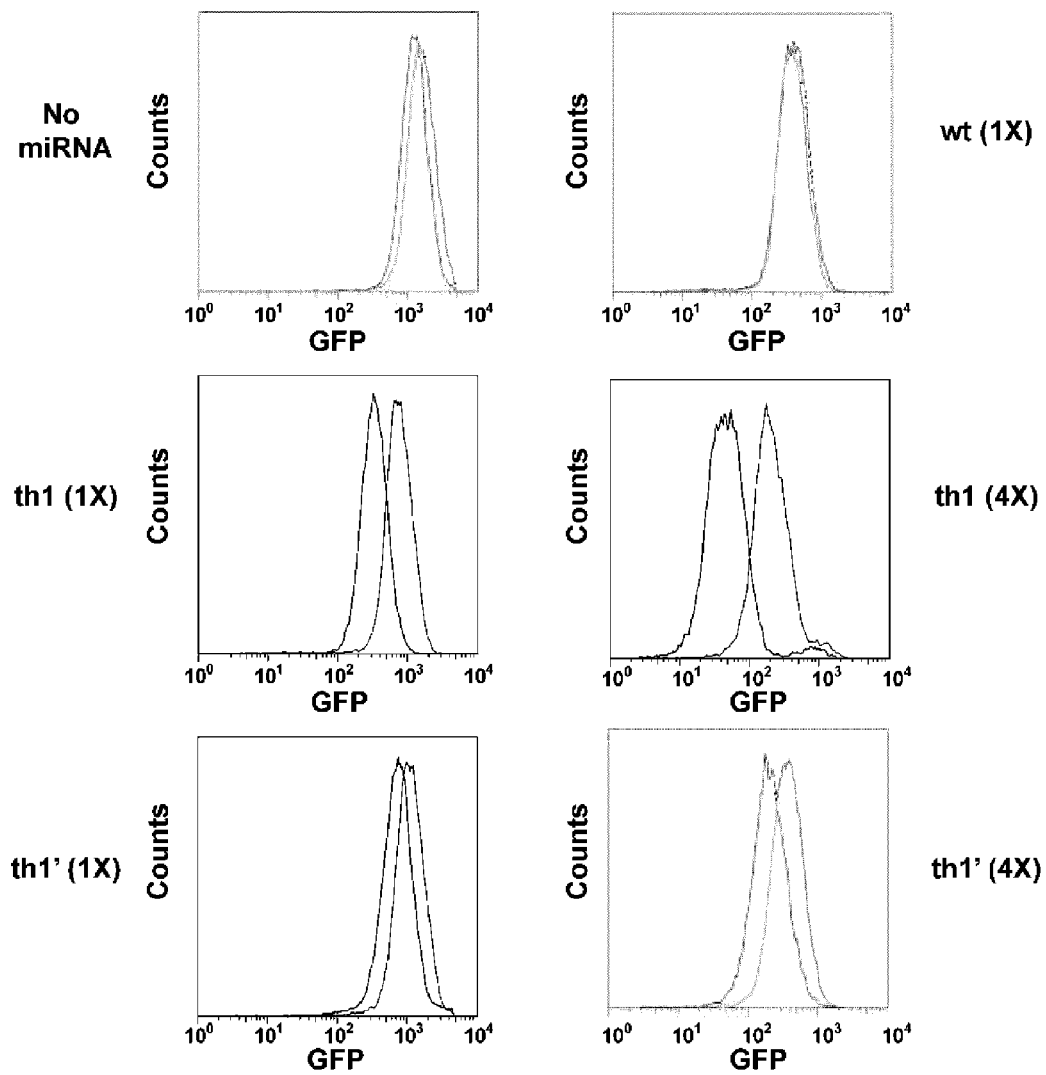
FIG. 11 shows flow cytometry histograms for 293-Flp-In cells stably expressing the self-targeting miRNA constructs. miRNAs were located in the 3' UTR of the trans-targeted transcript encoding GFP. Constructs lacking any miRNAs (No miRNA), one copy of a self-targeting miRNA with basal segments containing sequences similar to miR-30a (wt), one (1X) or four (4X) copies of a theophylline-responsive self-targeting miRNA (th1), and one or four copies of a theophylline-responsive non-targeting miRNA (th1') were characterized, where multiple copies were separated by the largest spacer length tested (112 nt). Stable cell lines were grown for over one week in the presence (lighter line) or absence (black) of 1.5 mM theophylline prior to flow cytometry analysis.

Self-Targeting miRNAs Combine Trans and Cis Regulation for a Tighter Control System Ligand-responsive miRNAs can regulate genes in trans through RISC targeting and in cis through Drosha cleavage. A control system based on combining both modes of regulation into 'self-targeting miRNAs' may offer tighter regulation while still operating within the 3' UTR of the transgene encoding transcript. We developed a dual-acting miRNA circuit based on the insertion of ligand-responsive miRNAs or miRNA clusters into the 3' UTR of a targeted GFP transcript (FIG. 6A), where ligand control of Drosha cleavage is expected to impact direct destabilization of the cleaved transcript and subsequent RISC-mediated inactivation of other target transcripts. The resulting constructs were stably integrated into 293-Flp-In cells to ensure consistent expression for all constructs. Cells were grown in the presence or absence of 1.5 mM theophylline for over a week and analyzed by flow cytometry. The self-targeting miRNAs (combined cis and trans mechanism; th1) improved both GFP silencing and the dynamic range as compared to their non-targeting counterparts (cis mechanism; th1') (FIGS. 6B, 11). Similar effects were observed for the self-targeting miRNA clusters. These results demonstrate the diverse tuning capabilities when encoding ligand-responsive miRNAs in a transcript 3' UTR by implementing self-targeting and non-targeting miRNAs at different copy numbers.

Figure 12:
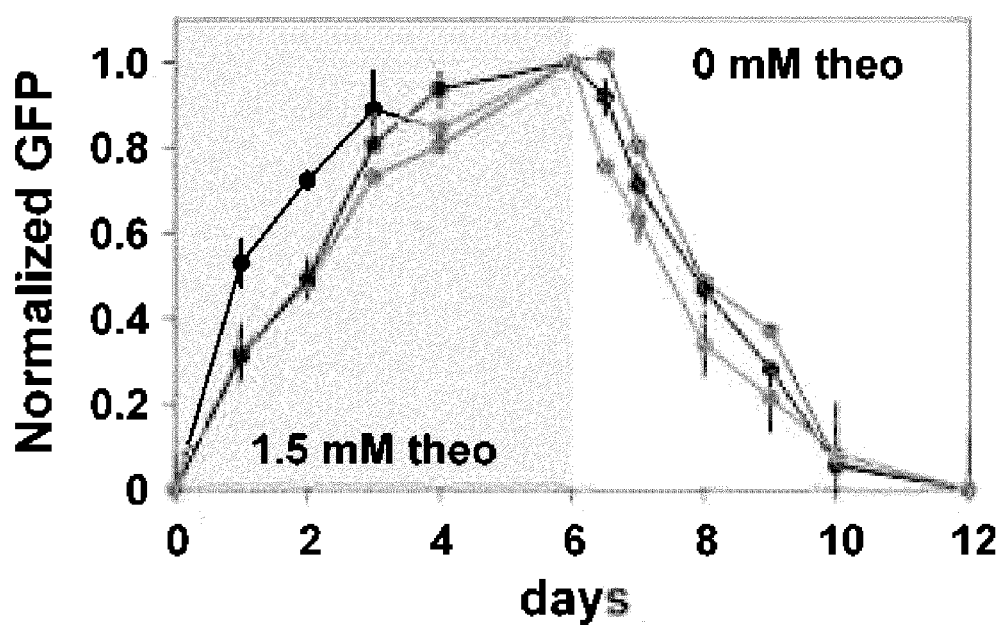
FIG. 12 shows dynamics of ligand-responsive miRNA regulation in response to a step-change in ligand concentration. Data are shown for cells expressing the miRNA constructs containing four copies of th1' (red), one copy of th1 (blue), or four copies of th1 (black). Cells were grown in the presence of 1.5 mM theophylline for six days then transferred to media without theophylline for six days. Time course data were normalized to zero when theophylline was added at the beginning of the time course and one when theophylline was removed in the middle of the time course to compare the dynamics of the approach to steady-state between ligand-responsive miRNAs acting through different regulatory mechanisms. Error bars represent the standard deviation of cells grown in two separate culture wells.

We performed time course studies on the dual-acting miRNA circuits to examine the dynamic properties of these regulatory systems. Cells lines were grown in the presence of theophylline for six days and then grown in media without theophylline for another six days. Cell lines harboring th1 or th1' in single or four copies exhibited increasing GFP levels when grown in the presence of theophylline and reached steady-state levels by day 6 (FIGS. 6C, 12). GFP levels decreased upon removal of theophylline and returned to original levels after 4-6 days of growth in the absence of theophylline, indicating that the genetic control exerted by ligand-responsive miRNAs is reversible. The rate of approach to steady-state was consistently slower for cis/trans regulation versus cis regulation after theophylline addition, likely due to the slow turnover of activated RISC molecules (Bartlett and Davis, 2006) (FIG. 12). The particular response dynamics associated with the cis and cis/trans regulatory mechanisms offer yet another design parameter when specifying the regulatory performance of ligand-responsive miRNAs.

Example 8

Use of 2 Aptamers within a Single miRNA

Figure 14:
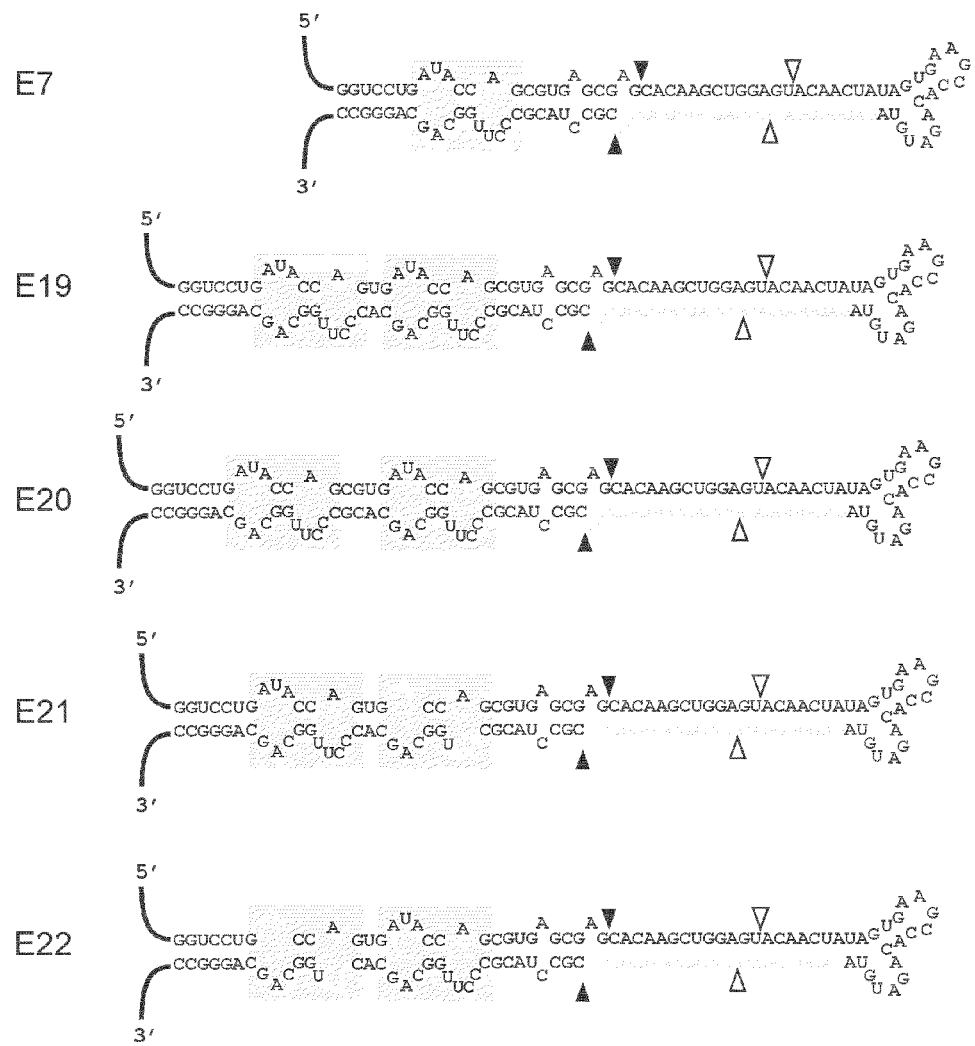
FIG. 14 shows the design of ligand-responsive miRNAs containing two aptamer domains. A second theophylline aptamer was introduced into the base miRNA containing one theophylline aptamer (E7) with either 3 (E19) or 5 (E20) base pairs separating the aptamer binding cores. Mutations that disrupt binding were used in the top aptamer (E21) and bottom aptamer (E22) of E19 to assess whether the two aptamers independently contribute to gene regulation. A theophylline response was generated for the different constructs.
Figure 14:
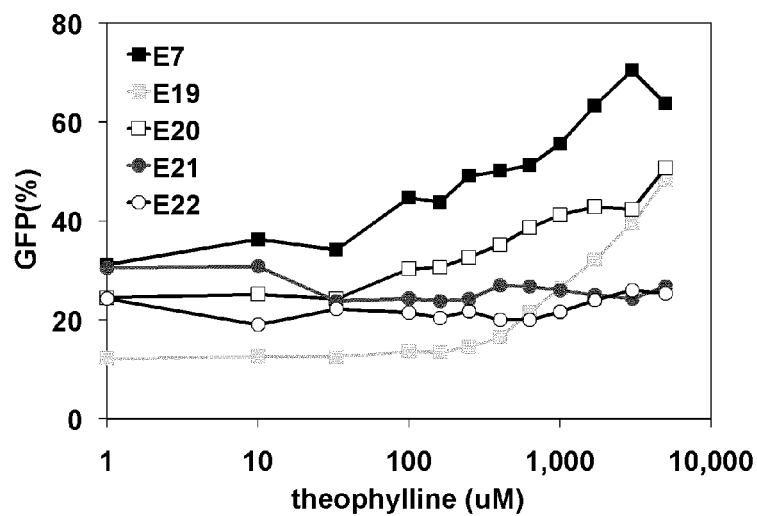

As shown in FIG. 14, an miRNA with 2 aptamer domains (separated by either). Modified miRNAs were constructed with one (E7), or two theophylline-binding aptamer sequences, separated by either 3 (E19) or 5 (E20) base pairs. Each of the constructs had in place a guide sequence targeting GFP. Measurement of GFP levels in the presence of various concentrations of theophylline showed that the miRNAs were responsive to theophylline in a dose-dependent fashion, where controls having mutations in the FIG. 14 shows the design of ligand-responsive miRNAs containing two aptamer domains. A second theophylline aptamer was introduced into the base miRNA containing one theophylline aptamer (E7) with either 3 (E19) or 5 (E20) base pairs separating the aptamer binding cores. Mutations that disrupt binding were used in the top aptamer (E21) and bottom aptamer (E22) of E19 to assess whether the two aptamers independently contribute to gene regulation. A theophylline response was generated for the different constructs.

Example 9

Methods

Experimental Procedures

Plasmid Construction.

Figure 13:
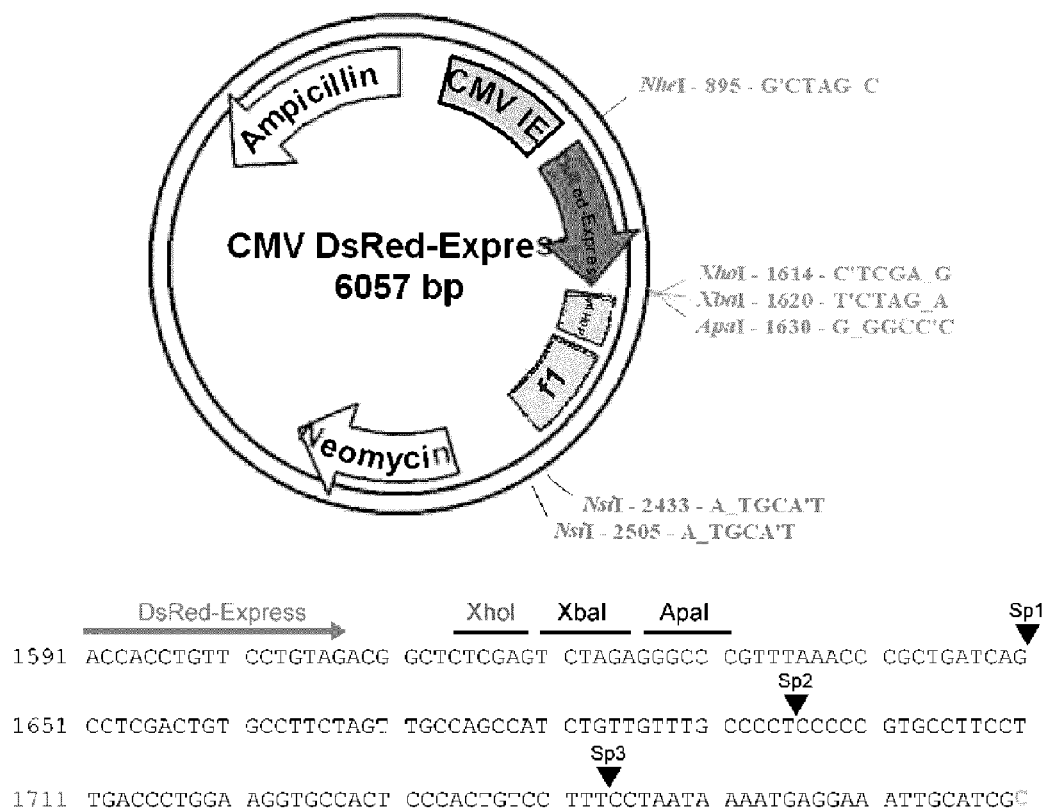
FIG. 13 shows a plasmid map of pcDNA3.1(+) expressing DsRed-Express and sequence of the miRNA insertion site. The gene encoding DsRed-Express was cloned into NheI/XhoI with a Kozak consensus sequence (SEQ ID NO. 2: CGCCACC) immediately upstream of the start codon. DsRed-Express is expressed from the constitutive and strong CMV IE promoter. MiRNAs were cloned into XbaI/ApaI located in the DsRed-Express 3' untranslated region, were the resulting miRNA sequences are listed in Table 1. Multiple copies of miRNAs were sequentially inserted by amplifying the miRNA with the PCR primers listed in Methods and cloned into XhoI/XbaI. Sp 1, Sp2, and Sp3 mark the 3' end of miRNAs with an intervening sequence of 20, 64, and 112 nt, respectively. The 3' end of the DsRed-Express coding region is designated in red. Numbering corresponds to the original pcDNA3.1(+) vector.

The coding region of DsRed-Express was initially cloned with the consensus Kozak sequence (CGCCACC) into the NheI/XhoI restriction sites of pcDNA3.1(+) (FIG. 13). pcDNA3.1(+) contains the constitutive CMV promoter upstream of a multicloning site. Ligand-responsive and control miRNAs reported in Table 7 were cloned into XbaI/ApaI downstream of each coding region. To construct synthetic miRNA clusters, additional miRNAs were digested with AvrII/XhoI and iteratively inserted into XhoI/XbaI within the miRNA-containing plasmid. For the 2-nt spacer, the second miRNA (th3) was separately prepared and inserted. For all other spacer lengths, the original miRNA was amplified with a common forward primer and a reverse primer that hybridizes different distances downstream of the miRNA:

```
SEQ ID NO. 3:
Sp.fwd:    5'-GTTCCTGTAGACGGCTCTC-3';

SEQ ID NO. 4:
Sp1.rev:   5'-AATACCTAGGCTGATCAGCGGGTTT-3';

SEQ ID NO. 5:
Sp2.rev:   5'-AATACCTAGGAGGGGCAAACAACAG-3';

SEQ ID NO. 6:
Sp3.rev,   5'-AATACCTAGGAAAGGACAGTGGGAGTG-3'.
```

To make stable cell lines, the coding region of DsRed-Express was replaced with EGFP and the entire transcript was excised with NheI/NsiI and cloned into the same sites in pcDNA5/FRT (Invitrogen). Prior to insertion, the NsiI site was introduced into this plasmid at position 1524 using site-directed mutagenesis. All restriction enzymes and T4 DNA ligase were purchased from New England Biolabs. All constructs were sequence-verified (Laragen).

RNA Preparation.

Internally radiolabeled RNAs were transcribed in vitro from an annealed template containing the T7 promoter (5'-TTCTAATACGACTCACTATAGGG-3', where G is the first transcribed nucleotide) using the Ampliscribe T7 transcription kit (Epicentre) according to the manufacturer's instructions with [α-32P]-GTP. Following transcription and DNase treatment, the transcription product was purified through a NucAway clean-up column (Ambion) according to the manufacturer's instructions and gel-purified by PAGE.

Drosha Cleavage Assays.

In vitro assays were conducted as described previously (Lee and Kim, 2007). Briefly, the Drosha complex was immunopurified from 293T cells transiently transfected with pCK-Drosha-FLAG and pCK-DGCR8-FLAG (9:1 mass ratio). Two days post-transfection, cells were lysed using M-PER (Pierce) according to the manufacturer's instructions and the resulting supernatant was incubated with Anti-FLAG M2 affinity beads (Sigma Aldrich) for at least 1 hr at 4° C. with rotation. The beads were then washed with the lysis buffer (20 mM Tris-HCl pH 8.0, 100 mM KCl, 0.2 mM EDTA) five times and evenly divided for the in vitro assays (two in vitro reactions from a 10 cm transfection dish). Radiolabeled RNAs (~105 cpm, 3 µl) were combined with 0.75 µl RNasin (Promega), 3 µl reaction buffer (64 mM MgCl2), 8.25 µl water, and 15 µl immunopurified Drosha complex. After an incubation of 90 min at 37° C., the reaction was terminated with the addition of 0.5 M sodium acetate and 0.02% sodium dodecyl sulfate (SDS), phenol:chloroform extracted, and ethanol precipitated. Samples were then resuspended in 15 µl RNA loading buffer (95% formamide, 0.02% SDS, 0.025% bromophenol blue, 0.025% xylene cyanol FF) and resolved on a 12.5% denaturing polyacrylamide gel. The RNA decades ladder (Ambion) was used as a size marker.

Cell Culture and Transfection.

293 and Flp-In-293 cells were maintained in DMEM supplemented with 10% FBS at 37° C. in a 5% CO2—humidified incubator. Transient transfections were conducted with Fugene 6 (Roche) according to the manufacturer's instructions one day after seeding. Immediately prior to transfection, the media was supplemented with the appropriate ligand at the specified concentration. Ligand concentrations were selected to maximize the regulatory response without severely compromising cell viability over the course of the transient assays. The media was replaced two days post-transfection. Three days post-transfection, the cells were trypsinized and subjected to flow cytometry analysis on a Cell Lab Quanta SC MPL (Beckman Coulter) and the resulting data was analyzed using the Flowjo software (Tree Star). Cells were initially gated for viability by electronic volume and side scatter. GFP and DsRed fluorescence of viable cells were measured through a 525 nm and 760 nm band pass filter, respectively, after excitation with a 488 nm laser. Moderate to high DsRed levels served as a transfection control to gate between transfected and untransfected cells. Transfected cells could be distinguished from untransfected cells with this method even when four miRNAs were present in the 3' UTR of the DsRed-Express encoding transcript (data not shown). GFP levels were calculated as the median fluorescence of the transfected population divided by that of the untransfected population (Beisel et al., 2008). This normalization approach corrected for the bias from pleiotropic effects associated with each small molecule. All ratios were normalized such that the value for DsRed-Express lacking a miRNA under the same conditions was set to 100%.

Reported DsRed measurements are the mean value of the transfected population normalized to the construct lacking a miRNA set to 100%, where the mean value was selected based on the high variability associated with transient plasmid-based expression of fluorescent proteins.

Stable transfection of 293-Flp-In cell lines was performed using the Flp-In recombinase system (Invitrogen) according to the manufacturer's instructions to generate isogenic stable cell lines. Integrants were selected using 200 µg/ml hygromycin B (Invitrogen), whereas stable cell lines were maintained in 50 µg/ml hygromycin B. The procedure described above for the fluorescence expression analysis of transiently transfected cell populations was used to analyze the stable cell lines with notable exceptions. Normalization of flow cytometry data to untransfected cells was not performed as all cells express the integrated construct, and all data was normalized to cells lacking a miRNA and grown in the absence of theophylline. Normalization to cells grown under the same conditions was not performed since theophylline differentially affected the two negative controls: no miRNA and a self-targeting miRNA lacking the theophylline aptamer. The different effects may be attributed to differences in perturbations induced by theophylline stress on unregulated genes and genes regulated by a self-targeting miRNA.

qRT-PCR. The following oligos were used for qRT-PCR.

```
La protein (Acc # X13697):
SEQ ID NO. 7:
La_fwd,        5'-GGTTGAACCGTCTAACAACAG-3';

SEQ ID NO. 8:
La_rev,        5'-ATGTCATCAAGAGTTGCATCAG-3';

GAPDH (Acc # NM_002046):
SEQ ID NO. 9:
GAPDH_fwd,     5'-GAAGGTGAAGGTCGGAGTC-3';

SEQ ID NO. 10:
GAPDH_rev,     5'-GAAGATGGTGATGGGATTTC-3';

DsRed-Express:
SEQ ID NO. 11:
DsRed.fwd,     5'-AAGAAGACTATGGGCTGGGA-3';

SEQ ID NO. 12:
DsRed.rev      5'-CGATGGTGTAGTCCTCGTTG-3';
and the Neomycin resistance gene:
SEQ ID NO. 13:
NeoR.fwd,      5'-ACCTTGCTCCTGCCGAGAAAGTAT-3';

SEQ ID NO. 14:
NeoR.rev,      5'-ATGTTTCGCTTGGTGGTCGAATGG-3'.
```

Transcript levels were measured by qRT-PCR under either transient or stable transfection conditions. For transient transfections 293 cells were washed with 1×PBS three days post-transfection and total RNA was extracted using the RNeasy Mini kit (Qiagen) according to the manufacturer's instructions. For stable transfections, cell lines were grown for over a week in the presence or absence of 1.5 mM theophylline prior to total RNA extraction. Total RNA samples were treated with DNase I at 37° C. for 20 minutes and purified using a NucAway column (Ambion). Up to 5 µg of purified RNA was reverse-transcribed using Superscript III reverse transcriptase (Invitrogen) according to the manufacturer's instructions using the reverse primers for each pair of gene target and loading control (DsRed/NeoR, La/GAPDH) followed by the recommended incubation with RNase H. qRT-PCR was conducted with the resulting cDNA on the iCycler iQ system (BioRAD) according to the manufacturer's instructions. Samples were prepared in quadruplicate using the iQ SYBR green supermix and data were analyzed using the iCycler iQ software. The mean of the resulting CT values for the target gene of each sample were subtracted from the mean CT value for the control gene. The resulting values were then converted from log 2 to linear scale and normalized to the value for the sample lacking any miRNA transfected with the same concentration of ligand. The reported sample error was calculated using the following expression:

$$\text{Sample error} = \frac{2^{AVE(Cont)-AVE(Target)-\frac{1}{2}[SD(Cont)-SD(Target)]}}{[2^{AVE(Cont)-AVE(Target)}]_{Neg}}$$

where AVE and SD are the respective average and standard deviation of each quadruplicate sample, Cont and Target are the loading control and target, respectively, and Neg is the sample lacking a miRNA transfected with the same ligand concentration as the sample in question.

Design of Mature miRNAs.

The mature miRNA sequences targeting GFP and La were selected to be completely complementary to a single site within each coding region. GFP was targeted at positions 416 (SEQ ID NO. 15: GGCACAAGCTGGAGTACAACTA) and 281 (SEQ ID NO. 16: TCCAGGAGCGCACCATCTTCTT), and La was targeted at position 310 (SEQ ID NO. 17: ATGGAAATCAGTGAAGATAAAA). The first GFP-targeting sequence (416) was derived from the OpenBiosystems shRNA eGFP Positive PSM2 vector control, whereas the second GFP-targeting sequence (281) and the La-targeting sequence (310) were generated using Dharmacon's online siRNA design software. Mature miRNA sequences were then introduced into the top or bottom of the upper stem of the base miRNA.

Sequences of Ligand-Responsive and Control miRNAs.

TABLE 1

Sequences for ligand-responsive and control miRNAs. Each sequence is written 5' to 3' and represents the final construct cloned into XbaI and ApaI within pcDNA3.1(+). th3, th1 Sp1, th1 Sp2, and th1 Sp3 represent a second copy of th1 cloned into XhoI and XbaI in pcDNA3.1(+) already containing th1 to test the efficacy of two miRNAs separated by different spacer sequences.

| Name | Sequence | Aptamer | Database # |
|---|---|---|---|
| Wt | SEQ ID NO. 18:<br>TCTAGAGTTTGACAGTGAGCGAGCACAAGCTGGAGTACAACTATAGTG<br>AAGCCACAGATGTATAGTTGTACTCCAGCTTGTGCCTGCCTACTGCCT<br>CGGACTGAATTCATAGGGCCC | | pCS351 |
| m1 | SEQ ID NO. 19:<br>TCTAGAACGGGAAGTAATTACAGTGAGCGAGCACAAGCTGGAGTACAA<br>CTATAGTGAAGCCACAGATGTATAGTTGTACTCCAGCTTGTGCCTGCC<br>TACTGCCACATAGGGCCC | | pCS1246 |
| m2 | SEQ ID NO. 20:<br>TCTAGAACGGGAAACACAGTGAGCGAGCACAAGCTGGAGTACAACTAT<br>AGTGAAGCCACAGATGTATAGTTGTACTCCAGCTTGTGCCTGCCTACT<br>GCCTCGGGCCC | None | pCS1215 |
| m3 | SEQ ID NO. 21:<br>TCTAGAACGGGAAACACAGTGAGCGAGCACAAGCTGGAGTACAACTAT<br>AGTGAAGCCACAGATGTATAGTTGTACTCCAGCTTGTGCCTGCCTACT<br>GCCGGGCCC | | pCS1241 |
| m4 | SEQ ID NO. 22:<br>TCTAGAACGGGAAACACAGTGAGCGAGCACAAGCTGGAGTACAACTAT<br>AGTGAAGCCACAGATGTATAGTTGTACTCCAGCTTGTGCCTGCCTACT<br>GGGGCCC | | pCS1242 |
| th1 | SEQ ID NO. 23:<br>TCTAGAACGGGTCCTGATACCAGCGTGAGCGAGCACAAGCTGGAGTAC<br>AACTATAGTGAAGCCACAGATGTATAGTTGTACTCCAGCTTGTGCCCG<br>CCTACGCCCTTGGCAGCAGGGCCC | | pCS1183 |
| th1' | SEQ ID NO. 24:<br>TCTAGAACGGGTCCTGATACCAGCGTGAGCGAGCACAAGCTATCAACA<br>TGAGGTAGTGAAGCCACAGATGTACCTCATGTTGATAGCTTGTGCCCG<br>CCTACGCCCTTGGCAGCAGGGCCC | | pCS1258 |
| th2 | SEQ ID NO. 25:<br>TCTAGAACGGGTCCTGATACCAGCGTGAGCGCCAAGAAGATGGTGCGC<br>TCCTGGAGTGAAGCCACAGATGTCCAGGAGCGCACCATCTTCTTGTCG<br>CCTACGCCCTTGGCAGCA*GGGCCC* | Theophylline | pCS1664 |
| th3 | SEQ ID NO. 26:<br>TCTAGACGCCAGAATGATACCAGCGTGAGCGAGCACAAGCTGGAGTAC<br>AACTATAGTGAAGCCACAGATGTATAGTTGTACTCCAGCTTGTGCCCG<br>CCTACGCCCTTGGCAGCATTCTGGCGCCTAGAACGGGTCCTGATACCA<br>GCGTGAGCGAGCACAAGCTGGAGTACAACTATAGTGAAGCCACAGATG<br>TATAGTTGTACTCCAGCTTGTGCCCGCCTACGCCCTTGGCAGCAGGGC<br>CC | | pCS1229 |

TABLE 1-continued

Sequences for ligand-responsive and control miRNAs. Each sequence is written 5' to 3' and represents the final construct cloned into XbaI and ApaI within pcDNA3.1(+). th3, th1 Sp1, th1 Sp2, and th1 Sp3 represent a second copy of th1 cloned into XhoI and XbaI in pcDNA3.1(+) already containing th1 to test the efficacy of two miRNAs separated by different spacer sequences.

| Name | Sequence | Aptamer | Database # |
|---|---|---|---|
| th1 Sp1 | SEQ ID NO. 27:<br>*TCTAGA*ACGGGTCCTGATACCAGCGTGAGCGAGCACAAGCTGGAGTAC AACTATAGTGAAGCCACAGATGTATAGTTGTACTCCAGCTTGTGCCCG CCTACGCCCTTGGCAGCA*GGGCCC*GTTTAAACCCGCTGATCAG*CCTAG* AACGGGTCCTGATACCAGCGTGAGCGAGCACAAGCTGGAGTACAACTA TAGTGAAGCCACAGATGTATAGTTGTACCCAGCTTGTGCCCGCCTAC GCCCTTGGCAGCA*GGGCCC* | Theophylline | pCS1321 |
| th1 Sp2 | SEQ ID NO. 28:<br>*TCTAGA*ACGGGTCCGTGTATTACCTGAGCGAGCACAAGCTGGAGTACA ACTATAGTGAAGCCACAGATGTAAGTTGTACTCCAGCTTGTGCCCGC CTAGGTCGAC*GGGCCC*GTTTAAACCCGCTGATCAGCCTCGACTGTGCC TTCTAGTTGCCAGCCATCTGTTGTTTGCCCCTCCTAGAACGGGTCCTG ATACCAGCGTGAGCGAGCACAAGCTGGAGTACAACTATAGTGAAGCCA CAGATGTATAGTTGTACTCCAGCTTGTGCCCGCCTACGCCCTTGGCAG CA*GGGCCC* | | pCS1322 |
| th1 Sp3 | SEQ ID NO. 29:<br>*TCTAGA*ACGGGTCCCGAGGTCGACGTGAGCGAGCACAAGCTGGAGTACA ACTATAGTGAAGCCACAGATGTAAGTTGTACTCCAGCTTGTGCCCGC CTACGTGTATTACCCA*GGGCCC*GTTTAAACCCGCTGATCAGCCTCGAC TGTGCCTTCTAGTTGCCAGCCATCTGTTGTTTGCCCCTCCCCCGTGCC TTCCTTGACCCTGGAAGGTGCCACTCCCACTGTCCTTTT*CCTAGA*ACGG GTCCTGATACCAGCGTGAGCGAGCACAAGCTGGAGTACAACTATAGTG AAGCCACAGATGTAAGTTGTACTCCAGCTTGTGCCCGCCTACGCCCT TGGCAGCA*GGGCCC* | | pCS1323 |
| tc1 | SEQ ID NO. 30:<br>*TCTAGA*ACGGGTCCCTAAAACATACCGTGAGCGAGCACAAGCTGGAGTA CAACTATAGTGAAGCCACAGATGTATAGTTGTACTCCAGCTTGTGCCT GCCTACGGAGAGGTGAAGAATACGACCACCTA*GGGCCC* | Tetracycline | pCS1217 |
| xa1 | SEQ ID NO. 31:<br>*TCTAGA*ACGGGTCCGTGTATTACCTGAGCGAGCACAAGCTGGAGTACA ACTATAGTGAAGCCACAGATGTAAGTTGTACTCCAGCTTGTGCCCGC CTAGGTCGAC*GGGCCC* | Xanthine | pCS1218 |
| xa2 | SEQ ID NO. 32:<br>*TCTAGA*ACGGGTCCCGAGGTCGACGTGAGCGAGCACAAGCTGGAGTACA ACTATAGTGAAGCCACAGATGTAAGTTGTACTCCAGCTTGTGCCCGC CTACGTGTATTACCCA*GGGCCC* | | pCS1244 |
| La1 | SEQ ID NO. 33:<br>*TCTAGA*GTTTGACAGTGAGCGCTGGAAATCAGTGAAGATAAAATAGTG AAGCCACAGATGTATTTTATCTTCACTGATTTCCATTGCCTACTGCCT CGGACTGAATTCATA*GGGCCC* | None | pCS1676 |
| La2 | SEQ ID NO. 34:<br>*TCTAGA*ACGGGTCCTGATACCAGCGTGAGCGCTGGAAATCAGTGAAGA TAAAATAGTGAAGCCACAGATGTATTTTATCTTCACTGATTTCCATCG CCTACGCCCTTGGCAGCA*GGGCCC* | Theophylline | pCS1677 |

Legent:
italics, restriction sites; bold, aptamer; bold and underline, designed guide strand sequence.

REFERENCES

Aagaard, L. A., Zhang, J., von Eije, K. J., Li, H., Saetrom, P., Amarzguioui, M., and Rossi, J. J. (2008). Engineering and optimization of the miR-106b cluster for ectopic expression of multiplexed anti-HIV RNAs. Gene Ther 15, 1536-1549.

An, C. I., Trinh, V. B., and Yokobayashi, Y. (2006). Artificial control of gene expression in mammalian cells by modulating RNA interference through aptamer-small molecule interaction. RNA 12, 710-716.

Bartlett, D. W., and Davis, M. E. (2006). Insights into the kinetics of siRNA-mediated gene silencing from live-cell and live-animal bioluminescent imaging. Nucleic Acids Res 34, 322-333.

Bauer, M., Kinkl, N., Meixner, A., Kremmer, E., Riemenschneider, M., Forstl, H., Gasser, T., and Ueffing, M. (2009). Prevention of interferon-stimulated gene expression using microRNA-designed hairpins. Gene Ther 16, 142-147.

Bayer, T. S., and Smolke, C. D. (2005). Programmable ligand-controlled riboregulators of eukaryotic gene expression. Nat Biotechnol 23, 337-343.

Beisel, C. L., Bayer, T. S., Hoff, K. G., and Smolke, C. D. (2008). Model-guided design of ligand-regulated RNAi for programmable control of gene expression. Mol Syst Biol 4, 224.

Beisel, C. L., and Smolke, C. D. (2009). Design principles for riboswitch function. PLoS Comput Biol 5, e1000363.

Berens, C., Thain, A., and Schroeder, R. (2001). A tetracycline-binding RNA aptamer. Bioorg Med Chem 9, 2549-2556.

Boudreau, R. L., Martins, I., and Davidson, B. L. (2009). Artificial microRNAs as siRNA shuttles: improved safety as compared to shRNAs in vitro and in vivo. Mol Ther 17, 169-175.

Cai, X., Hagedorn, C. H., and Cullen, B. R. (2004). Human microRNAs are processed from capped, polyadenylated transcripts that can also function as mRNAs. RNA 10, 1957-1966.

Friedman, R. C., Farh, K. K., Burge, C. B., and Bartel, D. P. (2009). Most mammalian mRNAs are conserved targets of microRNAs. Genome Res 19, 92-105.

Gregory, R. I., Yan, K. P., Amuthan, G., Chendrimada, T., Doratotaj, B., Cooch, N., and Shiekhattar, R. (2004). The Microprocessor complex mediates the genesis of microRNAs. Nature 432, 235-240.

Grimm, D., Streetz, K. L., Jopling, C. L., Storm, T. A., Pandey, K., Davis, C. R., Marion, P., Salazar, F., and Kay, M. A. (2006). Fatality in mice due to oversaturation of cellular microRNA/short hairpin RNA pathways. Nature 441, 537-541.

Guil, S., and Caceres, J. F. (2007). The multifunctional RNA-binding protein hnRNP A1 is required for processing of miR-18a. Nat Struct Mol Biol 14, 591-596.

Han, J., Lee, Y., Yeom, K. H., Kim, Y. K., Jin, H., and Kim, V. N. (2004). The Drosha-DGCR8 complex in primary microRNA processing. Genes Dev 18, 3016-3027.

Han, J., Lee, Y., Yeom, K. H., Nam, J. W., Heo, I., Rhee, J. K., Sohn, S. Y., Cho, Y., Zhang, B. T., and Kim, V. N. (2006). Molecular basis for the recognition of primary microRNAs by the Drosha-DGCR8 complex. Cell 125, 887-901.

Han, J., Pedersen, J. S., Kwon, S. C., Belair, C. D., Kim, Y. K., Yeom, K. H., Yang, W. Y., Haussler, D., Blelloch, R., and Kim, V. N. (2009). Posttranscriptional crossregulation between Drosha and DGCR8. Cell 136, 75-84.

Hermann, T., and Patel, D. J. (2000). Adaptive recognition by nucleic acid aptamers. Science 287, 820-825.

Jenison, R. D., Gill, S. C., Pardi, A., and Polisky, B. (1994). High-resolution molecular discrimination by RNA. Science 263, 1425-1429.

Kedde, M., Strasser, M. J., Boldajipour, B., Oude Vrielink, J. A., Slanchev, K., le Sage, C., Nagel, R., Voorhoeve, P. M., van Duijse, J., Orom, U. A., et al. (2007). RNA-binding protein Dnd1 inhibits microRNA access to target mRNA. Cell 131, 1273-1286.

Kiga, D., Futamura, Y., Sakamoto, K., and Yokoyama, S. (1998). An RNA aptamer to the xanthine/guanine base with a distinctive mode of purine recognition. Nucleic Acids Res 26, 1755-1760.

Koizumi, M., and Breaker, R. R. (2000). Molecular recognition of cAMP by an RNA aptamer. Biochemistry 39, 8983-8992.

Lee, Y., Ahn, C., Han, J., Choi, H., Kim, J., Yim, J., Lee, J., Provost, P., Radmark, O., Kim, S., et al. (2003). The nuclear RNase III Drosha initiates microRNA processing. Nature 425, 415-419.

Lee, Y., Jeon, K., Lee, J. T., Kim, S., and Kim, V. N. (2002). MicroRNA maturation: stepwise processing and subcellular localization. EMBO J. 21, 4663-4670.

Lee, Y., and Kim, V. N. (2007). In vitro and in vivo assays for the activity of Drosha complex. Methods Enzymol 427, 89-106.

McBride, J. L., Boudreau, R. L., Harper, S. Q., Staber, P. D., Monteys, A. M., Martins, I., Gilmore, B. L., Burstein, H., Peluso, R. W., Polisky, B., et al. (2008). Artificial miRNAs mitigate shRNA-mediated toxicity in the brain: implications for the therapeutic development of RNAi. Proc Natl Acad Sci USA 105, 5868-5873.

Muller, M., Weigand, J. E., Weichenrieder, O., and Suess, B. (2006). Thermodynamic characterization of an engineered tetracycline-binding riboswitch. Nucleic Acids Res 34, 2607-2617.

Osborne, S. E., and Ellington, A. D. (1997). Nucleic Acid Selection and the Challenge of Combinatorial Chemistry. Chem. Rev 97, 349-370.

Stern, P., Astrof, S., Erkeland, S. J., Schustak, J., Sharp, P. A., and Hynes, R. O. (2008). A system for Cre-regulated RNA interference in vivo. Proc Natl Acad Sci USA 105, 13895-13900.

Suess, B., and Weigand, J. E. (2008). Engineered riboswitches: overview, problems and trends. RNA Biol 5, 24-29.

Sun, D., Melegari, M., Sridhar, S., Rogler, C. E., and Zhu, L. (2006). Multi-miRNA hairpin method that improves gene knockdown efficiency and provides linked multi-gene knockdown. Biotechniques 41, 59-63.

Tuerk, C., MacDougal, S., and Gold, L. (1992). RNA pseudoknots that inhibit human immunodeficiency virus type 1 reverse transcriptase. Proc Natl Acad Sci USA 89, 6988-6992.

Tuleuova, N., An, C. I., Ramanculov, E., Revzin, A., and Yokobayashi, Y. (2008).

Modulating endogenous gene expression of mammalian cells via RNA-small molecule interaction. Biochem Biophys Res Commun 376, 169-173.

Wang, M., Xie, H., Mi, S., and Chen, J. (2007). Recent patents on the identification and clinical application of microRNAs and target genes. Recent Pat DNA Gene Seq 1, 116-124.

Wang, V., and Wu, W. (2009). MicroRNA-based therapeutics for cancer. BioDrugs 23, 15-23.

Weigand, J. E., Sanchez, M., Gunnesch, E. B., Zeiher, S., Schroeder, R., and Suess, B. (2008). Screening for engineered neomycin riboswitches that control translation initiation. RNA 14, 89-97.

Wieland, M., Benz, A., Klauser, B., and Hartig, J. S. (2009). Artificial ribozyme switches containing natural riboswitch aptamer domains. Angew Chem Int Ed Engl 48, 2715-2718.

Wilson, C., Nix, J., and Szostak, J. (1998). Functional requirements for specific ligand recognition by a biotin-binding RNA pseudoknot. Biochemistry 37, 14410-14419.

Win, M. N., and Smolke, C. D. (2007). A modular and extensible RNA-based gene regulatory platform for engineering cellular function. Proc Natl Acad Sci USA 104, 14283-14288.

Xia, X. G., Zhou, H., and Xu, Z. (2006). Multiple shRNAs expressed by an inducible pol II promoter can knock down the expression of multiple target genes. Biotechniques 41, 64-68.

Zeng, Y., and Cullen, B. R. (2003). Sequence requirements for micro RNA processing and function in human cells. RNA 9, 112-123.

Zeng, Y., and Cullen, B. R. (2005). Efficient processing of primary microRNA hairpins by Drosha requires flanking nonstructured RNA sequences. J Biol Chem 280, 27595-27603.

Zeng, Y., Wagner, E. J., and Cullen, B. R. (2002). Both natural and designed micro RNAs can inhibit the expression of cognate mRNAs when expressed in human cells. Mol Cell 9, 1327-1333.

Zeng, Y., Yi, R., and Cullen, B. R. (2005). Recognition and cleavage of primary microRNA precursors by the nuclear processing enzyme Drosha. EMBO J. 24, 138-148.

Zhang, Y., Zhang, R., and Su, B. (2009). Diversity and evolution of MicroRNA gene clusters. Sci China C Life Sci 52, 261-266.

What is claimed is:

1. A system comprising a nucleic acid comprising:
   (a) an miRNA nucleic acid domain, wherein the miRNA nucleic acid domain has a basal segment region; and
   (b) an RNA sensor domain that binds to a ligand, wherein the RNA sensor domain is in the basal segment region;
   wherein the basal segment region is formed by:
   (1) a first region that, at the 5' end is defined by the 5'-end of the miRNA, and, at the 3' end is defined by
      (i) in a first configuration, a 5' Drosha cleavage site, or,
      (ii) in a second configuration, a 5' of a guide sequence region, or,
      (iii) in a third configuration, a 5' of a complement of a guide sequence region; and,
   (2) a second region that, at the 3' end is defined by the 3'-end of the miRNA, and, at the 5' end is defined by
      (i) in the first configuration, a 3' Drosha cleavage site, or,
      (ii) in the second configuration, a 3' of the complement of the guide sequence region, or,
      (iii) in the third configuration, a 3' of the guide sequence region;
   wherein said first region base pairs with said second region to form a stem.

2. The system of claim 1, wherein binding of the ligand to the sensor domain modulates processing of the miRNA nucleic acid domain by an RNA binding protein or RNA processing enzyme.

3. The system of claim 1, wherein a portion of the miRNA nucleic acid domain is complementary to a target RNA transcript.

4. The system of claim 1, wherein the nucleic acid comprises more than one RNA sensor domain, and wherein the sensor domains bind to the ligand.

5. The system of claim 1, wherein the nucleic acid further comprises a second miRNA nucleic acid domain and a second RNA sensor domain, configured to bind to a ligand, wherein the RNA sensor domain is located within the basal segment region of the second miRNA nucleic acid domain.

6. The system of claim 1, wherein the nucleic acid has more than one RNA sensor domain, and wherein at least one sensor domain binds to the ligand, and further comprising at least one additional ligand, wherein at least one sensor domain binds to the additional ligand.

7. The system of claim 2, wherein binding of the ligand to the sensor domain inhibits processing by the RNA processing enzyme or RNA binding protein.

8. The system of claim 2, wherein binding of the ligand to the sensor domain enhances processing by the RNA processing enzyme or RNA binding protein.

9. The system of claim 2, wherein the RNA processing enzyme or RNA binding protein is Drosha.

10. The system of claim 2, wherein the RNA processing enzyme or RNA binding protein is DGCR8.

11. The system of claim 1, wherein the ligand is endogenous to a cell.

12. The system of claim 1, wherein the ligand is exogenous to a cell.

13. The system of claim 12, wherein the ligand is cell permeable.

14. The system of claim 1, wherein the ligand is selected from the group consisting of polypeptides, peptides, nucleic acids, carbohydrates, fatty acids, lipids, non-peptide hormones, and metabolic precursors or products thereof.

15. The system of claim 1, wherein the ligand has a molecular weight less than about 2.5 kDa.

16. The system of claim 1, wherein the ligand has a molecular weight of less than about 1 kDa.

17. The system of claim 1, wherein the ligand is theophylline, tetracycline, phenobarbital, tamoxifen, folinic acid, vitamin B12, biotin, Rev, Tat, dopamine, p50, p65, B-catenin, SAM, SAH, TPP, vitamin B1, adenine, or guanosine.

18. The system of claim 1, wherein the miRNA down regulates expression of a target RNA.

19. The system of claim 1, wherein the miRNA activates expression of a target RNA.

20. A cell comprising one or more nucleic acids of claim 1.

21. The cell of claim 20, wherein the cell is a prokaryotic cell or a eukaryotic cell.

22. The system of claim 20, wherein the cell is a mammalian cell.

23. The cell of claim 20, wherein the cell is a plant cell.

24. A method of processing an miRNA, the method comprising:
   (a) providing to a cell, the system of claim 1; and,
   (b) contacting the cell with the ligand, thereby processing the miRNA.

25. The system of claim 1, wherein the stem comprises mismatched base pairs or a bulge.

26. The system of claim 1, wherein said first region comprises a first part of the RNA sensor domain, and said second region comprises a second part of the RNA sensor domain.

27. The system of claim 3, wherein the guide sequence region is at least about 50%, 60%, 70%, 80%, 90%, or 95% complementary to the target RNA transcript.

28. The system of claim 1, wherein said 5'-end of the miRNA base pairs with said 3'-end of the miRNA in said stem.

* * * * *